(12) United States Patent
Bhatia et al.

(10) Patent No.: US 11,519,905 B2
(45) Date of Patent: Dec. 6, 2022

(54) METHODS TO SPATIALLY PROFILE PROTEASE ACTIVITY IN TISSUE AND SECTIONS

(71) Applicant: Massachusetts Institute of Technology, Cambridge, MA (US)

(72) Inventors: Sangeeta N. Bhatia, Lexington, MA (US); Jaideep S. Dudani, Cambridge, MA (US); Ester J. Kwon, Cambridge, MA (US); Andrew David Warren, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 15/947,644

(22) Filed: Apr. 6, 2018

(65) Prior Publication Data
US 2018/0335429 A1    Nov. 22, 2018

Related U.S. Application Data

(60) Provisional application No. 62/483,245, filed on Apr. 7, 2017.

(51) Int. Cl.

| | | |
|---|---|---|
| *C12Q 1/68* | (2018.01) | |
| *C12Q 1/00* | (2006.01) | |
| *G01N 33/574* | (2006.01) | |
| *G01N 33/53* | (2006.01) | |
| *G01N 33/543* | (2006.01) | |
| *A61K 49/00* | (2006.01) | |
| *G01N 33/542* | (2006.01) | |
| *C07K 19/00* | (2006.01) | |
| *C12Q 1/37* | (2006.01) | |
| *G01N 33/58* | (2006.01) | |
| *A61K 47/68* | (2017.01) | |
| *A61K 49/18* | (2006.01) | |
| *C07K 14/705* | (2006.01) | |
| *C12N 9/74* | (2006.01) | |
| *C12N 9/64* | (2006.01) | |
| *G01N 33/553* | (2006.01) | |
| *C07K 14/47* | (2006.01) | |

(52) U.S. Cl.
CPC ... *G01N 33/54346* (2013.01); *A61K 47/6815* (2017.08); *A61K 47/6889* (2017.08); *A61K 49/0043* (2013.01); *A61K 49/0056* (2013.01); *A61K 49/186* (2013.01); *C07K 14/705* (2013.01); *C07K 19/00* (2013.01); *C12N 9/6429* (2013.01); *C12N 9/6445* (2013.01); *C12N 9/6454* (2013.01); *C12N 9/6491* (2013.01); *C12Q 1/37* (2013.01); *G01N 33/542* (2013.01); *G01N 33/553* (2013.01); *G01N 33/574* (2013.01); *G01N 33/582* (2013.01); *C07K 14/47* (2013.01); *C07K 2319/02* (2013.01); *C07K 2319/33* (2013.01); *C07K 2319/50* (2013.01); *C07K 2319/60* (2013.01); *C07K 2319/75* (2013.01)

(58) Field of Classification Search
CPC ................ A61K 49/00; A61K 49/0063; A61K 49/0056; C07K 14/4748; C07K 14/705
USPC ........................................ 424/9.1, 9.2; 435/4
See application file for complete search history.

(56) References Cited

U.S. PATENT DOCUMENTS

| | | | |
|---|---|---|---|
| 5,500,161 | A | 3/1996 | Andrianov et al. |
| 5,811,252 | A | 9/1998 | Verheijen |
| 5,885,775 | A | 3/1999 | Haff et al. |
| 6,312,390 | B1 | 11/2001 | Phillips |
| 6,335,429 | B1 | 1/2002 | Cai et al. |
| 6,592,847 | B1 | 7/2003 | Weissleder et al. |
| 6,597,996 | B1 | 7/2003 | Venkataraman et al. |
| 6,629,040 | B1 | 9/2003 | Goodlett et al. |
| 6,824,981 | B2 | 11/2004 | Chait et al. |
| 7,041,453 | B2 | 5/2006 | Yang |
| 7,169,892 | B2 | 1/2007 | Atsushi et al. |
| 7,179,655 | B2 | 2/2007 | Patricelli |
| 7,329,506 | B2 | 2/2008 | William |
| 7,412,332 | B1 | 8/2008 | Venkataraman et al. |
| 7,456,269 | B2 | 11/2008 | Gurney et al. |
| 7,468,258 | B2 | 12/2008 | Owen |
| 7,544,518 | B2 | 6/2009 | Aebersold et al. |
| 7,595,155 | B2 | 9/2009 | Murakami |
| 7,879,574 | B2 | 2/2011 | Packard et al. |
| 7,985,401 | B2 | 7/2011 | Jiang et al. |

(Continued)

FOREIGN PATENT DOCUMENTS

| | | | |
|---|---|---|---|
| CN | 102558362 A | | 7/2012 |
| CN | 103012595 A | | 4/2013 |

(Continued)

OTHER PUBLICATIONS

Parker et al., Analytical Biochemistry 338: 284-293, 2005.*

(Continued)

*Primary Examiner* — Gary B Nickol
*Assistant Examiner* — Lakia J Jackson-Tongue
(74) *Attorney, Agent, or Firm* — Wolf, Greenfield & Sacks, P.C.

(57) ABSTRACT

Aspects of the disclosure relate to methods and compositions useful for in vivo and/or in vitro enzyme profiling. In some embodiments, the disclosure provides methods of in vivo enzymatic processing of exogenous molecules followed by detection of signature molecules as representative of the presence of active enzymes associated with diseases or conditions. In some embodiments, the disclosure provides compositions and in vitro methods for localization of enzymatic activity in a tissue sample.

21 Claims, 39 Drawing Sheets
Specification includes a Sequence Listing.

(56) References Cited

U.S. PATENT DOCUMENTS

| | | |
|---|---|---|
| 8,673,267 B2 * | 3/2014 | Bhatia ............... G01N 33/6842 |
| | | 424/9.1 |
| 8,841,085 B2 | 9/2014 | Kwon et al. |
| 8,969,027 B2 | 3/2015 | Bossmann et al. |
| 9,006,415 B2 | 4/2015 | Ren et al. |
| 9,072,792 B2 | 7/2015 | Jiang et al. |
| 9,155,471 B2 | 10/2015 | Lee et al. |
| 9,657,326 B2 | 5/2017 | Ruether et al. |
| 9,695,251 B2 | 7/2017 | Tsien et al. |
| 9,808,532 B2 | 11/2017 | Tsien et al. |
| 9,913,917 B2 | 3/2018 | Groves et al. |
| 9,970,941 B2 | 5/2018 | Bhatia et al. |
| 10,006,916 B2 | 6/2018 | Kwong et al. |
| 10,527,619 B2 | 1/2020 | Bhatia et al. |
| 10,883,998 B2 | 1/2021 | Bhatia et al. |
| 11,054,428 B2 | 7/2021 | Bhatia et al. |
| 2002/0119490 A1 | 8/2002 | Aebersold et al. |
| 2003/0059952 A1 | 3/2003 | Chait et al. |
| 2004/0014652 A1 | 1/2004 | Dubois et al. |
| 2004/0091943 A1 | 5/2004 | Schneider |
| 2005/0107583 A1 | 5/2005 | Jiang et al. |
| 2005/0260695 A1 | 11/2005 | Fleming et al. |
| 2006/0008856 A1 | 1/2006 | Singh et al. |
| 2006/0257883 A1 | 11/2006 | Bjoraker et al. |
| 2006/0292631 A1 | 12/2006 | Broberg et al. |
| 2007/0010433 A1 | 1/2007 | Albrechtsen et al. |
| 2007/0048752 A1 | 3/2007 | Yan et al. |
| 2007/0207555 A1 | 9/2007 | Guerra et al. |
| 2008/0026480 A1 | 1/2008 | Guerra |
| 2008/0064607 A1 | 3/2008 | Yang |
| 2008/0095758 A1 | 4/2008 | Lee et al. |
| 2008/0113875 A1 | 5/2008 | Chaurand et al. |
| 2008/0213377 A1 | 9/2008 | Bhatia et al. |
| 2008/0226562 A1 | 9/2008 | Groves et al. |
| 2008/0241955 A1 | 10/2008 | Purkayastha et al. |
| 2008/0253960 A1 | 10/2008 | Zheng et al. |
| 2009/0016988 A1 | 1/2009 | Buckley |
| 2009/0088332 A1 | 4/2009 | Ju et al. |
| 2009/0156424 A1 | 6/2009 | Thompson |
| 2009/0230300 A1 | 9/2009 | Trevejo et al. |
| 2009/0246142 A1 | 10/2009 | Bhatia et al. |
| 2009/0252677 A1 | 10/2009 | Bogyo et al. |
| 2010/0022408 A1 | 1/2010 | Singh et al. |
| 2010/0124757 A1 | 5/2010 | Kwon et al. |
| 2010/0190193 A1 | 7/2010 | Calatzis et al. |
| 2010/0240050 A1 * | 9/2010 | Bhatia ............... G01N 33/6842 |
| | | 435/6.14 |
| 2010/0317542 A1 | 12/2010 | Lim et al. |
| 2011/0014125 A1 | 1/2011 | Bossmann et al. |
| 2011/0021908 A1 | 1/2011 | Lee et al. |
| 2011/0104052 A1 | 5/2011 | Barnett et al. |
| 2011/0104071 A1 | 5/2011 | Lee et al. |
| 2012/0039990 A1 | 2/2012 | Reshetnyak et al. |
| 2012/0150164 A1 | 6/2012 | Lee et al. |
| 2013/0078188 A1 | 3/2013 | Tsien et al. |
| 2013/0295129 A1 | 11/2013 | Irvine et al. |
| 2013/0315906 A1 | 11/2013 | Lowman et al. |
| 2014/0207129 A1 | 7/2014 | Lee |
| 2014/0234431 A1 | 8/2014 | Bhatia et al. |
| 2014/0255313 A1 | 9/2014 | Vasiljeva et al. |
| 2014/0276102 A1 | 9/2014 | Lee et al. |
| 2014/0276103 A1 | 9/2014 | Lee et al. |
| 2014/0301950 A1 | 10/2014 | Lee et al. |
| 2014/0303014 A1 | 10/2014 | Kwong et al. |
| 2014/0363833 A1 * | 12/2014 | Bhatia ............... G01N 33/573 |
| | | 435/7.94 |
| 2014/0364368 A1 | 12/2014 | Lin et al. |
| 2015/0051153 A1 | 2/2015 | Reshetnyak et al. |
| 2015/0080721 A1 | 3/2015 | Novak et al. |
| 2015/0104381 A1 | 4/2015 | Maina-Nock et al. |
| 2015/0165062 A1 | 6/2015 | Liao et al. |
| 2015/0344523 A1 * | 12/2015 | Deyle ................. G01N 33/573 |
| | | 514/19.3 |
| 2016/0025632 A1 | 1/2016 | Lee et al. |
| 2016/0096869 A1 | 4/2016 | Hansen et al. |
| 2016/0184459 A1 | 6/2016 | Ueki et al. |
| 2016/0289324 A1 | 10/2016 | Moore et al. |
| 2016/0317037 A1 | 11/2016 | Lee et al. |
| 2017/0267727 A1 | 9/2017 | Thevenin et al. |
| 2017/0305968 A1 | 10/2017 | Tsien et al. |
| 2018/0021090 A1 | 1/2018 | Lee et al. |
| 2018/0196058 A1 | 7/2018 | Kwong et al. |
| 2018/0328941 A1 | 11/2018 | Bhatia et al. |
| 2019/0076081 A1 | 3/2019 | Hyde et al. |
| 2019/0128873 A1 | 5/2019 | Bhatia et al. |
| 2019/0144917 A1 | 5/2019 | Bhatia et al. |
| 2019/0212291 A1 | 7/2019 | Dudani et al. |
| 2019/0271704 A1 | 9/2019 | Bhatia et al. |
| 2019/0345534 A1 | 11/2019 | Kwong et al. |
| 2019/0376113 A1 | 12/2019 | Bhatia et al. |
| 2020/0096514 A1 | 3/2020 | Bhatia et al. |
| 2020/0116725 A1 | 4/2020 | Bhatia et al. |
| 2020/0225231 A1 | 7/2020 | Bhatia et al. |
| 2020/0232986 A1 | 7/2020 | Bhatia et al. |
| 2020/0249194 A9 | 8/2020 | Dudani et al. |
| 2021/0148926 A1 | 5/2021 | Bhatia et al. |
| 2021/0262025 A1 | 8/2021 | Bhatia et al. |

FOREIGN PATENT DOCUMENTS

| | | |
|---|---|---|
| CN | 108484847 A | 9/2018 |
| JP | 2004-506900 | 3/2004 |
| JP | 2004-129651 | 4/2004 |
| JP | 2007-024631 A2 | 2/2007 |
| JP | 2007-206054 A | 8/2007 |
| JP | 2009-108037 | 5/2009 |
| JP | 2009-524688 | 7/2009 |
| JP | 2009-538430 A | 11/2009 |
| JP | 2013-060452 | 4/2013 |
| JP | 2016-520327 | 7/2016 |
| WO | WO 2002/014867 A2 | 2/2002 |
| WO | 2006/034370 A2 | 3/2006 |
| WO | WO 2007/060921 A2 | 5/2007 |
| WO | WO 2007/072070 A1 | 6/2007 |
| WO | WO 2008/072676 A1 | 6/2008 |
| WO | WO 2008/093513 A1 | 8/2008 |
| WO | WO 2008/127019 A1 | 10/2008 |
| WO | WO 2009/124265 A1 | 10/2009 |
| WO | WO 2010/101628 A2 | 9/2010 |
| WO | WO 2011/008996 A2 | 1/2011 |
| WO | WO 2012/031250 A2 | 3/2012 |
| WO | WO 2012/085080 A1 | 6/2012 |
| WO | WO 2012/125808 A1 | 9/2012 |
| WO | WO 2014/107599 A2 | 7/2014 |
| WO | WO 2014/120619 A2 | 8/2014 |
| WO | WO 2014/120974 A1 | 8/2014 |
| WO | WO 2014/176284 A1 | 10/2014 |
| WO | WO 2014/197816 | 12/2014 |
| WO | WO 2014/197840 A1 | 12/2014 |
| WO | WO 2015/042202 A1 | 3/2015 |
| WO | WO 2017/044894 A2 | 3/2017 |
| WO | WO 2017/120410 A1 | 7/2017 |
| WO | WO 2017/177115 A1 | 10/2017 |
| WO | WO 2017/180789 A2 | 10/2017 |
| WO | WO 2017/181149 A1 | 10/2017 |
| WO | WO 2018/049285 A1 | 3/2018 |
| WO | WO 2018/064383 A1 | 4/2018 |
| WO | WO 2018/187688 A1 | 10/2018 |
| WO | WO 2018/227132 A1 | 12/2018 |
| WO | WO 2019/071051 A1 | 4/2019 |
| WO | WO 2019/075292 A1 | 4/2019 |
| WO | WO 2019/089804 A1 | 5/2019 |
| WO | WO 2019/089820 A1 | 5/2019 |
| WO | WO 2019/126577 A2 | 6/2019 |
| WO | WO 2019/126716 A2 | 6/2019 |
| WO | WO 2019/126762 A2 | 6/2019 |
| WO | WO 2019/148206 A1 | 8/2019 |

OTHER PUBLICATIONS

Gatter et al., Journal of Clinical Pathology, 36(5):539-545, 1983.*
Jiang et al., PNAS, 2004; 101(51):17867-17872 (Year: 2004).*

(56) References Cited

OTHER PUBLICATIONS

International Preliminary Report on Patentability dated Oct. 17, 2019 for Application No. PCT/US2018/026458.
Böhm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.
Dennis et al., Albumin binding as a general strategy for improving the pharmacokinetics ofproteins. J Biol Chem. Sep. 20, 2002;277(38):35035-43. Epub Jul. 15, 2002.
Deshpande et al., Current trends in the use of liposomes for tumor targeting. Nanomedicine (Lond). Sep. 2013;8(9):1509-28. doi:10.2217/nnm.13.118.
Dudani et al., Classification of prostate cancer using a protease activity nanosensor library. Proc Natl Acad Sci U S A. Sep. 4, 2018;115(36):8954-8959. doi: 10.1073/pnas.1805337115. Epub Aug. 20, 2018.
Dudani et al., Harnessing Protease Activity to Improve Cancer Care. Ann Rev Cancer Biol. Mar. 2018;2:353-376.
Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.
Dudani et al., Sustained-release synthetic biomarkers for monitoring thrombosis and inflammation using point-of-care compatible readouts. Adv Funct Mater. May 3, 2016;26(17):2919-2928. doi: 10.1002/adfm.201505142. Epub Mar. 22, 2016.
Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015;12(1). doi:10.1038/nrclinonc.2014.70.
Kaminskas et al., Methotrexate-conjugated PEGylated dendrimers show differential patterns of deposition and activity in tumor-burdened lymph nodes after intravenous and subcutaneous administration in rats. Mol Pharm. Feb. 2, 2015;12(2):432-43. doi: 10.1021/mp500531e. Epub Jan. 20, 2015.
Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.
Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.
Lebeau et al., Imaging active urokinase plasminogen activator in prostate cancer. Cancer Res. Apr. 1, 2015;75(7):1225-35. doi:10.1158/0008-5472.CAN-14-2185. Epub Feb. 11, 2015.
McLennan et al., Subcutaneous drug delivery and the role of the lymphatics. Drug Discov Today Technol. 2005 Spring;2(1):89-96. doi:10.1016/j.ddtec.2005.05.006.
Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.
Prensner et al., Beyond PSA: the next generation of prostate cancer biomarkers. Sci Transl Med. Mar. 28, 2012;4(127):127rv3. doi:10.1126/scitranslmed.3003180.
Sawyers, The cancer biomarker problem. Nature. Apr. 3, 2008;452(7187):548-52. doi: 10.1038/nature06913.
Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.
Sugahara et al., Coadministration of a tumor-penetrating peptide enhances the efficacy of cancer drugs. Science. May 21, 2010;328(5981):1031-5. doi:10.1126/science.1183057. Epub Apr. 8, 2010.
Sutherland et al., RGD-Binding Integrins in Prostate Cancer: Expression Patterns and Therapeutic Prospects against Bone Metastasis. Cancers (Basel). Oct. 26, 2012;4(4):1106-45. doi:10.3390/cancers4041106.
Taylor et al., Integrative genomic profiling of human prostate cancer. Cancer Cell. Jul. 13, 2010;18(1):11-22. doi:10.1016/j.ccr.2010.05.026. Epub Jun. 24, 2010.
Thorek et al., Internalization of secreted antigen-targeted antibodies by the neonatal Fc receptor for precision imaging of the androgen receptor axis. Sci Transl Med. Nov. 30, 2016;8(367):367ra167.
Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.
Withana et al., Labeling of active proteases in fresh-frozen tissues by topical application of quenched activity-based probes. Nat Protoc. Jan. 2016;11(1):184-91. doi: 10.1038/nprot.2016.004. Epub Dec. 30, 2015.
Xia et al., Multiplex detection of protease activity with quantum dot nanosenors prepared by Intein-Mediated specific bioconjugation. Analytical Chemistry. Nov. 15, 2008; 22(80) 8649-8655.
U.S. Appl. No. 15/842,162, filed Dec. 14, 2017, Kwong et al.
U.S. Appl. No. 14/298,662, filed Jun. 6, 2014, Bhatia et al.
U.S. Appl. No. 16/099,147, filed Nov. 5, 2018, Bhatia et al.
U.S. Appl. No. 16/091,145, filed Oct. 4, 2018, Bhatia et al.
U.S. Appl. No. 16/159,340, filed Oct. 12, 2018, Dudani et al.
PCT/US2018/026458, Oct. 17, 2019, International Preliminary Report on Patentability.
Abudayyeh, Nanoparticle-Chaperoned Urinary "Synthetic Biomarkers" for Profiling Proteases in Cancer. Thesis. Department of Mechanical Engineering. Jun. 2012.
Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.
Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.
Asai et al., A colorimetric assay for plasma antithrombin III using a new synthetic peptide substrate (PS-915). Clin Chim Acta. Dec. 29, 1984;144(2-3):163-71.
Baruch et al., Enzyme activity—it's all about image. Trends Cell Biol. Jan. 2004;14(1):29-35.
Becker et al., Thrombin: Structure, Biochemistry, Measurement, and Status in Clinical Medicine. J Thromb Thrombolysis. Jul. 1998;5(3):215-229.
Blum et al., Noninvasive optical imaging of cysteine protease activity using fluorescently quenched activity-based probes. Nat Chem Biol. Oct. 2007;3(10):668-77. Epub Sep. 9, 2007.
Bounameaux et al., Plasma measurement of D-dimer as diagnostic aid in suspected venous thromboembolism: an overview. Thromb Haemost. Jan. 1994;71(1):1-6.
Chen et al., A unique substrate recognition profile for matrix metalloproteinase-2. J Biol Chem. Feb. 8, 2002;277(6):4485-91.
Daniel et al., Implantable diagnostic device for cancer monitoring. Biosens Bioelectron. Jul. 15, 2009;24(11):3252-7. Epub Apr. 16, 2009.
De La Rica et al., Enzyme-responsive nanoparticles for drug release and diagnostics. Adv Drug Deliv Rev. Aug. 2012;64(11):967-78. doi: 10.1016/j.addr.2012.01.002. Epub Jan. 14, 2012.
Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05.018. Epub May 25, 2013.
Dranoff, Cytokines in cancer pathogenesis and cancer therapy. Nat Rev Cancer. Jan. 2004;4(1):11-22.
D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.
Farrell et al., Non-motor parkinsonian pathology in aging A53T α-synuclein mice is associated with progressive synucleinopathy and altered enzymatic function. J Neurochem. Feb. 2014;128(4):536-46. doi: 10.1111/jnc.12481. Epub Nov. 20, 2013.
Fowlkes et al., Proteolysis of insulin-like growth factor binding protein-3 during rat pregnancy: a role for matrix metalloproteinases. Endocrinology. Dec. 1994;135(6):2810-3.

(56) References Cited

OTHER PUBLICATIONS

Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.
Genbank Submission; NIH/NCBI, Accession No. 2WV1_A; Kovalevskiy et al.; Mar. 24, 2010.
Genbank Submission; NIH/NCBI, Accession No. CAG01641; Mar. 17, 2004.
Genbank Submission; NIH/NCBI, Accession No. NP_938673; Cerdeno-Tarraga et al.; Jun. 3, 2010.
Genbank Submission; NIH/NCBI, Accession No. NP731669; Hoskins et al.; Dec. 18, 2009.
Genbank Submission; NIH/NCBI, Accession No. XP_001385378; Jeffries et al.; Apr. 11, 2008.
Genbank Submission; NIH/NCBI, Accession No. XP_002097000; Clark et al.; Aug. 12, 2009.
Genbank Submission; NIH/NCBI, Accession No. XP_00234527.; Jul. 7, 2006.
Genbank Submission; NIH/NCBI, Accession No. ZP_03507634; Gonzalez et al.; Dec. 19, 2008.
Genbank Submission; NIH/NCBI, Accession No. ZP_06431346; Small et al.; Jun. 9, 2010.
Ghadiali, James E. et al., "Enzyme-Responsive Nanoparticle Systems," Advanced Materials, vol. 20(22):4359-4363 (2008).
Giljohann, et al., Drivers of biodiagnostic development. Nature. Nov. 26, 2009;462(7272):461-4. doi: 10.1038/nature08605.
Ginsberg et al., Sensitivity and specificity of a rapid whole-blood assay for D-dimer in the diagnosis of pulmonary embolism. Ann Intern Med. Dec. 15, 1998;129(12):1006-11.
Grayson et al., Multi-pulse drug delivery from a resorbable polymeric microchip device. Nat Mater. Nov. 2003;2(11):767-72.
Gross, Mass Spectrometry: A Textbook. Springer. $2^{nd}$ ed. Mar. 1, 2011. Chapter 9. 415-452.
Haro et al., Matrix metalloproteinase-7-dependent release of tumor necrosis factor-alpha in a model of herniated disc resorption. J Clin Invest. Jan. 2000;105(2):143-50.
Haun et al., Micro-NMR for rapid molecular analysis of human tumor samples. Sci Transl Med. Feb. 23, 2011;3(71):71ra16. doi: 10.1126/scitranslmed.3002048.
Imai et al., Degradation of decorin by matrix metalloproteinases: identification of the cleavage sites, kinetic analyses and transforming growth factor-betal release. Biochem J. Mar. 15, 1997;322 (Pt 3):809-14.
Ito et al., Degradation of interleukin Ibeta by matrix metalloproteinases. J Biol Chem. Jun. 21, 1996;271(25):14657-60.
Jaffer et al., In vivo imaging of thrombin activity in experimental thrombi with thrombinsensitive near-infrared molecular probe. Arterioscler Thromb Vase Biol. Nov. 1, 2002;22(11):1929-35.
Johnson et al., Computer program (SEQPEP) to aid in the interpretation of high-energy collision tandem mass spectra of peptides. Biomed Environ Mass Spectrom. Nov. 1989;18(11):945-57.
Kastelic et al., Stefin B, the major low molecular weight inhibitor in ovarian carcinoma. Cancer Lett. Jul. 15, 1994;82(1):81-8.
Kircher et al., A dual fluorochrome probe for imaging proteases. Bioconjug Chem. Mar.-Apr. 2004;15(2):242-8.
Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.
Kwon et al., Ultrasensitive tumour-penetrating nanosensors of protease activity. Nat Biomed Eng. 2017;1. pii: 0054. doi:10.1038/s41551-017-0054. Epub Apr. 10, 2017.
Kwong et al., Mass-encoded synthetic biomarkers for multiplexed urinary monitoring of disease. Nat Biotechnol. Jan. 2013;31(1):63-70. doi: 10.1038/nbt.2464. Epub Dec. 16, 2012.
Kwong et al., Mathematical framework for activity-based cancer biomarkers. Proc Natl Acad Sci U S A. Oct. 13, 2015;112(41):12627-32. doi: 10.1073/pnas.1506925112. Epub Sep. 28, 2015.

Lange et al., Selected reaction monitoring for quantitative proteomics: a tutorial. Mol Syst Biol. 2008;4:222. doi: 10.1038/msb.2008.61. Epub Oct. 14, 2008.
Larsen et al., Assay of plasma heparin using thrombin and the chromogenic substrate H-D-Phe-Pip-Arg-pNA (S-2238). Thromb Res. Aug. 1978;13(2):285-8.
Levi et al., Matrix metalloproteinase 2 releases active soluble ectodomain of fibroblast growth factor receptor 1. Proc Natl Acad Sci U S A. Jul. 9, 1996;93(14):7069-74.
Lin et al., Drug-induced amplification of nanoparticle targeting to tumors. Nano Today. Oct. 2014;9(5):550-559. doi:10.1016/j.nantod. 2014.09.001. Epub Sep. 23, 2014.
Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.
Mallick et al., Computational prediction of proteotypic peptides for quantitative proteomics. Nat Biotechnol. Jan. 2007;25(1):125-31. Epub Dec. 31, 2006.
Manes et al., The matrix metalloproteinase-9 regulates the insulin-like growth factor-triggered autocrine response in DU-145 carcinoma cells. J Biol Chem. Mar. 12, 1999;274(11):6935-45.
Martinez et al., Diagnostics for the developing world: microfluidic paper-based analytical devices. Anal Chem. Jan. 1, 2010;82(1):3-10. doi: 10.1021/ac9013989.
Mira et al., Insulin-like growth factor I-triggered cell migration and invasion are mediated by matrix metalloproteinase-9. Endocrinology. Apr. 1999;140(4):1657-64.
Mirtti et al., Expression of cystatins, high molecular weight cytokeratin, and proliferation markers in prostatic adenocarcinoma and hyperplasia. Prostate. Mar. 1, 2003;54(4):290-8.
Mitchell et al., Assay for plasma heparin using a synthetic peptide substrate for thrombin: introduction of the fluorophore aminoisophthalic acid, dimethyl ester. Thromb Res. Jul. 1978;13(1):47-52.
Morris et al., Urine and plasma levels of fibrinopeptide B in patients with deep vein thrombosis and pulmonary embolism. Thromb Res. May 1, 2003;110(2-3):159-65.
Nagase et al., Matrix metalloproteinases. J Biol Chem. Jul. 30, 1999;274(31):21491-4.
Nahrendorf et al., Hybrid in vivo FMT-CT imaging of protease activity in atherosclerosis with customized nanosensors. Arterioscler Thromb Vase Biol. Oct. 2009;29(10):1444-51. doi:10.1161/ATVBAHA. 109.193086. Epub Jul. 16, 2009. Supplemental Material.
Nomura et al., Activity-based protein profiling for biochemical pathway discovery in cancer. Nat Rev Cancer. Sep. 2010;10(9):630-8. doi: 10.1038/nrc2901. Epub Aug. 12, 2010.
Olson et al., In vivo fluorescence imaging of atherosclerotic plaques with activatable cell-penetrating peptides targeting thrombin activity. Integr Biol (Camb). Jun. 2012;4(6):595-605. doi: 10.1039/c2ib00161f. Epub Apr. 26, 2012.
Park et al., Magnetic Iron Oxide Nanoworms for Tumor Targeting and Imaging. Adv Mater. May 5, 2008;20(9): 1630-1635.
Park et al., Systematic surface engineering of magnetic nanoworms for in vivo tumor targeting. Small. Mar. 2009;5(6):694-700. doi: 10.1002/smll.200801789.
Peer et al., Nanocarriers as an emerging platform for cancer therapy. Nat Nanotechnol. Dec. 2007;2(12):751-60.
Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.
Posthuma-Trumpie et al., Lateral flow (immuno)assay: its strengths, weaknesses, opportunities and threats. A literature survey. Anal Bioanal Chem. Jan. 2009;393(2):569-82. doi: 10.1007/s00216-008-2287-2. Epub Aug. 13, 2008.
Powell et al., The metalloproteinase matrilysin proteolytically generates active soluble Fas ligand and potentiates epithelial cell apoptosis. Curr Biol. Dec. 16-30, 1999;9(24):1441-7.
Rajah et al., Elevated levels of the IGF-binding protein protease MMP-1 in asthmatic airway smooth muscle. Am J Respir Cell Mol Biol. Feb. 1999;20(2):199-208.
Rennke, How does glomerular epithelial cell injury contribute to progressive glomerular damage? Kidney Int Suppl. Feb. 1994;45:S58-63.

(56) References Cited

OTHER PUBLICATIONS

Rijkers et al., Design and synthesis of thrombin substrates with modified kinetic parameters. Thromb Res. Sep. 15, 1995;79(5-6):491-9.
Roepstorff et al., Proposal for a common nomenclature for sequence ions in mass spectra of peptides. Biomed Mass Spectrom. Nov. 1984;11(11):601.
Ross et al., Multiplexed protein quantitation in Saccharomyces cerevisiae using amine-reactive isobaric tagging reagents. Mol Cell Proteomics. Dec. 2004;3(12):1154-69. Epub Sep. 22, 2004.
Ruoslahti et al., Targeting of drugs and nanoparticles to tumors. J Cell Biol. Mar. 22, 2010;188(6):759-68. doi: 10.1083/jcb. 200910104. Epub Mar. 15, 2010.
Santini et al., A controlled-release microchip. Nature. Jan. 28, 1999;397(6717):335-8.
Schonbeck et al., Generation of biologically active IL-1 beta by matrix metalloproteinases: a novel caspase-1-independent pathway of IL-1 beta processing. J Immunol. Oct. 1, 1998;161(7):3340-6.
Schuerle et al., Magnetically Actuated Protease Sensors for in Vivo Tumor Profiling. Nano Lett. Oct. 12, 2016;16(10):6303-6310. Epub Sep. 13, 2016.
Shariat et al., Urine detection of survivin is a sensitive marker for the noninvasive diagnosis of bladder cancer. J Urol. Feb. 2004;171(2 Pt 1):626-30.
Smith et al., Rapid identification of highly active and selective substrates for stromelysin and matrilysin using bacteriophage peptide display libraries. J Biol Chem. Mar. 24, 1995;270(12):6440-9.
Suzuki et al., Matrix metalloproteinase-3 releases active heparin-binding EGF-like growth factor by cleavage at a specific juxtamembrane site. J Biol Chem. Dec. 12, 1997;272(50):31730-7.
Tascilar et al., Role of tumor markers and mutations in cells and pancreatic juice in the diagnosis of pancreatic cancer. Ann Oncol. 1999;10 Suppl 4:107-10.
Thompson et al., Tandem mass tags: a novel quantification strategy for comparative analysis of complex protein mixtures by MS/MS. Anal Chem. Apr. 15, 2003;75(8):1895-904. Erratum in: Anal Chem. Sep. 15, 2003;75(18):4942. Johnstone, R [added]. Anal Chem. Jun. 15, 2006;78(12):4235. Mohammed, A Karim A [added].
Tockman et al., Considerations in bringing a cancer biomarker to clinical application. Cancer Res. May 1, 1992;52(9 Suppl):2711s-2718s.
Truong et al., Isotope-coded chemical reporter and acid-cleavable affinity reagents for monitoring protein sulfenic acids. Bioorg Med Chem Lett. Sep. 1, 2011;21(17):5015-20. doi: 10.1016/j.bmcl.2011. 04.115. Epub May 3, 2011.
Tung et al., A novel near-infrared fluorescence sensor for detection of thrombin activation in blood. Chembiochem. Mar. 1, 2002;3(2-3):207-11.
Warren et al., Point-of-care diagnostics for noncommunicable diseases using synthetic urinary biomarkers and paper micro fluidics. Proc Natl Acad Sci U S A. Mar. 11, 2014;111(10):3671-6. doi:10. 1073/pnas.1314651111. Epub Feb. 24, 2014.
Weissleder et al., In vivo imaging of tumors with protease-activated near-infrared fluorescent probes. Nat Biotechnol. Apr. 1999;17(4):375-8.
Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.
Welser et al., Protease sensing with nanoparticle based platforms. Analyst. Jan. 7, 2011;136(1):29-41. doi: 10.1039/c0an00429d. Epub Sep. 28, 2010.
Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi: 10.1074/ mcp.M900254-MCP200. Epub Oct. 20, 2009.
Whiteaker et al., Antibody-based enrichment of peptides on magnetic beads for mass-spectrometry-based quantification of serum biomarkers. Anal Biochem. Mar. 1, 2007;362(1):44-54. Epub Dec. 20, 2006.
Whitney et al., Ratiometric activatable cell-penetrating peptides provide rapid in vivo readout of thrombin activation. Angew Chem Int Ed Engl. Jan. 2, 2013;52(1):325-30. doi: 10.1002/anie. 201205721. Epub Oct. 18, 2012.
Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.
Yager et al., Point-of-care diagnostics for global health. Annu Rev Biomed Eng. 2008;10:107-44. doi: 10.1146/annurev.bioeng.10. 061807.160524.
Yu et al., Cell surface-localized matrix metalloproteinase-9 proteolytically activates TGF-beta and promotes tumor invasion and angiogenesis. Genes Dev. Jan. 15, 2000;14(2):163-76.
Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.
Zieske, A perspective on the use of iTRAQ reagent technology for protein complex and profiling studies. J Exp Bot. 2006;57(7):1501-8. Epub Mar. 30, 2006.
U.S. Appl. No. 15/966,385, filed Apr. 30, 2018, Bhatia et al.
PCT/US2018/026458, Jun. 26, 2018, International Search Report and Written Opinion.
Aalipour et al., Engineered immune cells as highly sensitive cancer diagnostics. Nat Biotechnol. 2019;37:531-9.
Acharige et al., Breath-based diagnosis of fungal infections. J Breath Res. Feb. 6, 2018;12(2):027108. doi: 10.1088/1752-7163/ aa98al.
Amstad et al., Photo- and thermoresponsive polymersomes for triggered release. Angew Chem Int Ed. 2012;51:1-6.
Baeuchamp et al., Real-time breath gas analysis for pharmacokinetics: monitoring exhaled breath by on-line proton-transfer-reaction mass spectrometry after ingestion of eucalyptol-containing capsules. J Breath Res. Jun. 2010;4(2):026006. doi: 10.1088/1752-7155/4/2/026006. Epub Apr. 22, 2010.
Bartlett, Diagnostic tests for agents of community-acquired pneumonia. Clin Infect Dis. May 2011. 52(Suppl 4):S296-304. doi: 10.1093/cid/cir045.
Bascom et al., Use of Enzyme Tests in Characterization and Identification of Aerobic and Facultatively Anaerobic Gram-Positive Cocci. Clin Microbiol Rev. Apr. 1998; 11(2): 318-340.
Berger, Helicobacter pylori breath tests. BMJ. 2002;324:1263.
Bonomi et al., Detection of enzyme activity through catalytic signal amplification with functionalized gold nanoparticles. Angew Chem Int Ed. 2011;50:2307-12.
Buss et al., Protease activity sensors noninvasively classify bacterial infections and antibiotic responses. EBioMedicine. Dec. 2018;38:248-56. doi:10.1016/j.ebiom.2018.11.031.
Caliendo et al., Better Tests, Better Care: Improved Diagnostics for Infectious Diseases. Clin Infect Dis. Dec. 2013;57(3):S139-S170.
Castillo et al., Sensitive substrates for human leukocyte and porcine pancreatic elastase: A study of the merits of various chromophoric and fluorogenic leaving groups in assays for serine proteases. Anal Biochem. Oct. 1979;99(1):53-64.
Chan et al., Inhalable Nanosensors for Rapid Breath-Based Pathogen Identification in Respiratory Infection. Revolutions in Biotechnology. MIT. Presented Mar. 5-6, 2018 at Tang Center, MIT Campus. 1 page.
Cheng et al., Ultrasensitive scanometric strategy for detection of matrix metalloproteinases using a histidine tagged peptide—Au nanoparticle probe. Chem Commun. 2011;47:2877-9.
Coelho et al., Usefulness of C-reactive protein in monitoring the severe community-acquired pneumonia clinical course. Crit Care. Aug. 2007; 11(4):R92.
Cohen et al., Detection and localization of surgically resectable cancers with a multi-analyte blood test. Science. 2018;3247(80):1-10.
El Badrawy et al., Matrix Metalloproteinase-9 Expression in Lung Cancer Patients and Its Relation to Serum MMP-9 Activity, Pathologic Type, and Prognosis. J Bronchol Interven Pulmonol. Oct. 2014; 21(4):327-34. doi: 10.1097/LBR.0000000000000094.

(56) References Cited

OTHER PUBLICATIONS

Elegbede et al., Mechanistic studies of the triggered release of liposomal contents by matrix metalloproteinase-9. J Am Chem Soc. Aug. 13, 2008;130(32):10633-42. doi: 10.1021/ja801548g. Epub Jul. 22, 2008.
Elston et al., New continuous and specific fluorometric assays for Pseudomonas aeruginosa elastase and LasA protease. Anal Biochem. Sep. 2007;368(1):87-94.
Fernandez et al., Volatile Biomarkers in Breath Associated With Liver Cirrhosis—Comparisons of Pre- and Post-liver Transplant Breath Samples. EBIOM. 2015;2:1243-50.
Figueiredo et al., Near infrared thoracoscopy of tumoral protease activity for improved detection of peripheral lung cancer. Int J Cancer. Jun. 2006;118(11):2672-7. doi: 10.1002/ijc.21713.
Gaieska et al., Impact of time to antibiotics on survival in patients with severe sepsis or septic shock in whom early goal-directed therapy was initiated in the emergency department. Crit Care Med. Apr. 2010;38(4):1045-53. doi: 10.1097/CCM.0b013e3181cc4824.
Ghoshal et al., How to Interpret Hydrogen Breath Tests. J Neurogastroenterol Motil. 2011;17:312-7.
Haiko et al., The omptins of Yersinia pestis and *Salmonella enterica* cleave the reactive center loop of plasminogen activator inhibitor 1. J Bacteriol. Sep. 2010;192(18):4553-61. doi: 10.1128/JB.00458-10. Epub Jul. 16, 2010.
Harris et al., Protease-triggered unveiling of bioactive nanoparticles. Small. 2008;4(9):1307-12. doi: 10.1002/smll.200701319. Epub Aug. 8, 2008.
Haskins, The application of stable isotopes in biomedical research. Biomed Mass Spectrom. Jul. 1982;9(7):269-77.
Heaney et al., Real-time monitoring of exhaled volatiles using atmospheric pressure chemical ionization on a compact mass spectrometer. Bioanalysis. Jul. 2016;8(13):1325-36. doi: 10.4155/bio-2016-0045. Epub Jun. 9, 2016.
Herbig et al., Towards standardization in the analysis of breath gas volatiles. J Breath Res. 2014;8:1-11.
Holliday et al., Rapid Identification of *Staphylococcus aureus* by Using Fluorescent Staphylocoagulase Assays. J Clin Microbiol. Apr. 1999;37(4):1190-2.
Iwasaki et al., Control of adaptive immunity by the innate immune system. Nat Immunol. Mar. 19, 2015;16(4):343-53.
Janzen et al., Colorimetric sensor arrays for volatile organic compounds. Anal Chem. Jun. 1, 2006;78(11):3591-600.
Johnson et al., Active-site gating regulates substrate selectivity in a chymotrypsin-like serine protease the structure of haemophilus influenzae immunoglobulin A1 protease. J Mol Biol. Jun. 12, 2009;389(3):559-74. doi: 10.1016/j.jmb.2009.04.041. Epub Apr. 23, 2009.
Kalinska et al., Substrate specificity of *Staphylococcus aureus* cysteine proteases—Staphopains A, B and C. Biochimie. Feb. 2012;94(2):318-27. doi: 10.1016/j.biochi.2011.07.020. Epub Jul. 23, 2011.
Kaman et al., Evaluation of a FRET-Peptide Substrate to Predict Virulence in Pseudomonas aeruginosa. PLoS One; Nov. 2013;8(11):e81428.
Kasperkiewicz et al., Design of ultrasensitive probes for human neutrophil elastase through hybrid combinatorial substrate library profiling. PNAS. 2014;111:2518-23.
Kim et al., Applications of stable, nonradioactive isotope tracers in in vivo human metabolic research. Exp Mol Med. Jan. 2016; 48(1): e203. Epub Jan. 15, 2016. doi: 10.1038/emm.2015.97.
Kirkpatrick et al., Noninvasive lung cancer detection via pulmonary protease profiling. bioRxiv. 36 pages, doi: https://doi.org/10.1101/495259.
Krebs et al., Molecular analysis of circulating tumour cells-biology and biomarkers. Nat Rev Clin Oncol. 2014;11:129-44.
Krilaviciute et al., Detection of cancer through exhaled breath?: a systematic review Literature search. Oncotarget. 2015;6:38643-57.
Kulkarni et al., MMP-9 Responsive PEG Cleavable Nano vesicles for Efficient Delivery of Chemotherapeutics to Pancreatic Cancer. Mol Pharm. Jul. 7, 2014; 11(7): 2390-2399. doi: 10.1021/mp500108p.
Kwak et al., Volatile disease biomarkers in breath: a critique. Curr Pharm Biotechnol; 2011;12:1067-74.
Kwon et al., Porous Silicon Nanoparticle Delivery of Tandem Peptide Anti?Infectives for the Treatment of Pseudomonas aeruginosa Lung Infections. Adv Mat. Sep. 20, 2017;29(35). 21pages.
Laupland et al., The changing culture of the microbiology laboratory. Can J Infect Dis Med Microbiol. 2013 Autumn; 24(3):125-128. doi: 10.1155/2013/101630.
Liou et al., Nonisotropic Enzyme-Inhibitor Interactions: A Novel Nonoxidative Mechanism for Quantum Proteolysis by Human Neutrophils. Biochem. 1995;34(49):16171-7.
Loynachan et al., ANYL 234: Catalytic nanomaterials for amplified biosensing. Abstract of Papers, 256th National Meeting & Exposition of the ACS. ACS National Meeting & Exposition. Aug. 19, 2018. 1 page.
Matsumoto et al., Role of bacterial proteases in pseudomonal and serratial keratitis. Biol Chem. Jan. 2004;385(11):1007-16.
McCarter et al., Substrate Specificity of the *Escherichia coli* Outer Membrane Protease OmpT. J Bacteriol. Sep. 2004; 186(17): 5919-5925. doi: 10.1128/JB.186.17.5919-5925.2004.
Meyer et al., Respiratory protease / antiprotease balance determines susceptibility to viral infection and can be modified by nutritional antioxidants. Am J Physiol Lung Cell Mol Physiol. 2015;308:L1189-L1201.
Morihara, Pseudolysin and other pathogen endopeptidases of thermolysin family. Methods in Enzymol. 1995;248:242-53.
Murray, What is New in Clinical Microbiology—Microbial Identification by MALDI-TOF Mass Spectrometry. JMDI. 2012;14:419-23.
Nizio et al., In vitro volatile organic compound profiling using GCxGC-TOFMS to differentiate bacteria associated with lung infections: a proof-of-concept study. J Breath Res. Apr. 27, 2016;10:026008, 12 pages.
Ong et al., Inhalable nanosensors for rapid breath-based pathogen identification in respiratory infection. Adv Res Technol Symp. Mar. 5, 2018. 2 pages.
Ong et al., Use of Mass Spectrometric Vapor Analysis to Improve Canine Explosive Detection Efficiency. Anal Chem. 2017;89:6482-90.
Parks et al., Matrix metalloproteinases as modulators of inflammation and innate immunity. Nat Rev Immunol. Aug. 2004;4(8):617-29.
Patton et al., Inhaling medicines: delivering drugs to the body through the lungs. Nat Rev Drug Discov. Jan. 2007;6(1):67-74.
Patton et al., The lungs as a portal of entry for systemic drug delivery. Proc Am Thorac Soc. 2004;1(4):338-44.
Phillips et al., Variation in volatile organic compounds in the breath of normal humans. J Chromatogr B. 1999;729:75-88.
Potempa et al., Corruption of innate immunity by bacterial proteases. J Innate Immun. 2009;1(2):70-87.
Ross et al., Volatile compounds in blood headspace and nasal breath. J Breath Res. Sep. 13, 2017;11(4):046001. doi: 10.1088/1752-7163/aa7d10.
Roy et al., Matrix metalloproteinases as novel biomarkers and potential therapeutic targets in human cancer. J Clin Oncol. 2009;27:5287-97.
Ruoslahti, Tumor-penetrating peptides for improved drug delivery. Adv Drug Deliv Rev. Feb. 2017;110-111:3-12. doi: 10.1016/j.addr.2016.03.008. Epub Apr. 1, 2016.
Sethi et al., Clinical application of volatile organic compound analysis for detecting infectious diseases. Clin Microbiol Rev. Jul. 2013;26(3):462-75. doi: 10.1128/CMR.00020-13.
Shaw et al., The role and regulation of the extracellular proteases of *Staphylococcus aureus*. Microbiol. Jan. 2004; 150:217-28. doi: 10.1099/mic.0.26634-0.
Shibuya et al., Pseudomonas aeruginosa alkaline proteinase might share a biological function with plasmin. Biochim Biophys Acta. Apr. 29, 1991; 1077(3):316-24.

(56) References Cited

OTHER PUBLICATIONS

Stach et al., Unique Substrate Specificity of SplE Serine Protease from *Staphylococcus aureus*. Structure. Apr. 3, 2018;26(4):572-579.e4. doi: 10.1016/j.str.2018.02.008. Epub Mar. 8, 2018.
Sweeney et al., Robust classification of bacterial and viral infections via integrated host gene expression diagnostics. Sci Transl Med. Jul. 2016;8(346):346ra91.
Teesalu et al., Tumor-penetrating peptides. Frontiers in Oncol. Aug. 27, 2013;3(216):1-8. doi: 10.3389/fonc.2013.00216.
Thomassin et al., OmpT Outer Membrane Proteases of Enterohemorrhagic and Enteropathogenic *Escherichia coli* Contribute Differently to the Degradation of Human LL-37. Infect Immun. Feb. 2012; 80(2): 483-492. doi: 10.1128/IAI.05674-11.
Van Der Schee et al., Breathomics in lung disease. Chest. 2015;147:224-31.
Vessillier et al., Hydrolysis of glycine-containing elastin pentapeptides by LasA, a metalloelastase from Pseudomonas aeruginosa. Eur J Biochem. Feb. 2001;268(4):1049-57.
Wang et al., Intrinsic enzyme mimicking activity of gold nanoclusters upon visible light triggering and its application for colorimetric trypsin detection. Biosens Bioelectronics. 2015;64:523-9. Epub Sep. 30, 2014.
Warren et al., Disease detection by ultrasensitive quantification of microdosed synthetic urinary biomarkers. J Am Chem Soc. 2014;136:13709-14.
Warren et al., Harnessing protease activity to improve cancer care. Annual Rev Cancer Biol. 2018;2:353-76.
Wildeboer et al., Characterization of bacterial proteases with a panel of fluorescent peptide substrates. Anal Biochem. Jan. 15, 2009;384(2):321-8. doi: 10.1016/j.ab.2008.10.004. Epub Oct. 11, 2008.
Wilkinson et al., Ventilator-Associated Pneumonia is Characterized by Excessive Release of Neutrophil Proteases in the Lung. Chest. Dec. 2012; 142(6):1425-32.
Wilson et al., Applications and Advances in Electronic-Nose Technologies. Sensors (Basel). 2009;9(7):5099-148. doi: 10.3390/s90705099. Epub Jun. 29, 2009.
Zheng et al., Dual-reaction triggered sensitivity amplification for ultrasensitive peptide-cleavage based electrochemical detection of matrix metalloproteinase-7. Biosens Bioelectronics. 2018;103:46-52. Epub Feb. 21, 2018.
Zhou et al., Thermo-sensitive microgels supported gold nanoparticles as temperature-mediated catalyst. Chinese J Polym Sci. 2019;37:235-42. Epub Aug. 30, 2018.
Zhu et al., Detecting bacterial lung infections: in vivo evaluation of in vitro volatile fingerprints. J Breath Res. Jan. 10, 2013;7(1):016003, 7 pages.
Zumla et al., Rapid point of care diagnostic tests for viral and bacterial respiratory tract infections-needs, advances, and future prospects. Lancet Infect Dis. 2014;14(11):1123-35.
U.S. Appl. No. 16/691,788, filed Nov. 22, 2019, Bhatia et al.
U.S. Appl. No. 16/293,390, filed Mar. 5, 2019, Bhatia et al.
U.S. Appl. No. 16/582,053, filed Sep. 25, 2019, Bhatia et al.
U.S. Appl. No. 16/745,748, filed Jan. 17, 2020, Bhatia et al.
U.S. Appl. No. 16/654,572, filed Oct. 16, 2019, Bhatia et al.
[No Author Listed] Summary for peptidase S01.135: granzyme A. MEROPS. Retrieved from <https://www.ebi.ac.uk/merops/cgi-bin/pepsum?id=S01.135;type=P>. Apr. 26, 2019. 2 pages.
[No Author Listed] Summary for peptidase S01.010: granzyme B. MEROPS. Retrieved from <https://www.ebi.ac.uk/merops/cgi-bin/pepsum?id=S01.010;type=P>. Apr. 26, 2016. 2 pages.
[No Author Listed] Summary for peptidase S01.146: granzyme K. MEROPS. Retrieved from <https://www.ebi.ac.uk/merops/cgi-bin/pepsum?id=S01.146;type=P>. Apr. 26, 2019. 2 pages.
[No Author Listed], DQ™ Gelatin From Pig Skin, Fluorescein Conjugate—Special Packaging. ThermoFisher Scientific. ENZCHEK® Gelatinase/Collagenase Assay Kit Product Information Sheet. Accessed on Jul. 14, 2020. Retrieved from: <https://www.thermofisher.com/order/catalog/product/D12054#/D12054>. 4 pages.

Chan et al., Engineering synthetic breath biomarkers for respiratory disease. Nature Nanotechnol. Jul. 20, 2020;15:792-800.
Cheng et al., Multifunctional nanoparticles: Cost versus benefit of adding targeting and imaging capabilities. Sci. Nov. 16, 2012;338(6109):903-10.
Galati et al., Increased resistance of peptides to serum proteases by modification of their amino groups. Resist peptides against serum proteases. Jan. 8, 2003;58:558-61.
Jiang et al., Tumor imaging by means of proteolytic activation of cell-penetrating peptides. Proc. Natl. Acad. Sci. U. S. A. 2004;101:17867-17872.
Olson et al., In vivo characterization of activatable cell penetrating peptides for targeting protease activity in cancer. Integr Biol (Camb). Jun. 2009;1(5-6):382-93.
Rawlings et al., The MEROPS database of proteolytic enzymes, their substrates and inhibitors in 2017 and a comparison with peptidases in the PANTHER database. Nucleic Acid Res. Jan. 4, 2018;46(D1):D624-D632.
Vandooren et al., Zymography Methods for Visualizing Hydrolytic Enzymes. Nat Methods. Mar. 2013;10(3):211-20. doi: 10.1038/nmeth.2371.
Vasiljeva et al., Monitoring protease activity in biological tissues using antibody prodrugs as sensing probes. Sci Rep. Apr. 3, 2020;10(1):5894.
Wu et al., Expression and clinical significance of matrix metalloproteinase-9 in lymphatic invasiveness and metastasis of breast cancer. Plos One. 2014;9(5):e97804.
Yan et al., In Situ Zymography: A Molecular Pathology Technique to Localize Endogenous Protease Activity in Tissue Sections. Vet Pathol May 2003;40(3):227-36.
Guimaraes et al., Site-specific C-terminal internal loop labeling of proteins using sortase-mediated reactions. NatProtoc. 2013;8:1787-99.
Liu et al., Structure-based programming of lymph-node targeting in molecular vaccines. Nature. Mar. 27, 2014;507(7493):519-22. doi: 10.1038/nature12978. Epub Feb. 14, 2014.
Nouh et al., Cathepsin B: a potential prognostic marker for inflammatory breast cancer. J Transl Med. 2011;9(1):8 pages.
Rousalova et al., Granzyme B-induced apoptosis in cancer cells and its regulation (review). Int J Oncol. Dec. 2010;37(6):1361-78. doi: 10.3892/ijo_00000788. PMID: 21042704.
Schmid et al., Albumin-binding prodrugs of camptothecin and doxorubicin with an ala-leu-ala-leu-linker that are cleaved by cathepsin b: synthesis and antitumor efficacy. Bioconj Chem. 2007;18(3):702-16.
Trapani et al., Killing by cytotoxic T cells and natural killer cells: multiple granule serine proteases as initiators of DNA fragmentation. Immunol Cell Biol. 1993;71(3):201-8.
Extended European Search Report for EP Application No. 21172148.5 dated Jan. 10, 2022.
Partial Supplementary European Search Report for EP Application No. 17779900.4 dated Nov. 12, 2020.
Extended European Search Report for EP Application No. 17779900.4 dated Feb. 12, 2021.
International Preliminary Report on Patentability for International Application No. PCT/US2020/014007 dated Jul. 29, 2021.
International Search Report and Written Opinion for International Application No. PCT/US2020/065547 dated Apr. 15, 2021.
[No Author Listed], Amidase Protein Classification Interpro. 2021. 2 pages.
[No Author Listed], Emboss Needle Sequence Alignment. 2021. 2 pages.
Chen et al., CRISPR-Cas12a target binding unleashes indiscriminate single-stranded DNase activity. Science. Apr. 27, 2018;360(6387):436-439. doi: 10.1126/science.aar6245. Epub Feb. 15, 2018. Erratum in: Science. Feb. 19, 2021;371(6531).
Danino et al., Programmable probiotics for detection of cancer in urine. Sci Transl Med. May 27, 2015;7(289):289ra84. doi: 10.1126/scitranslmed.aaa3519. PMID: 26019220; PMCID: PMC4511399.
Farwell et al., PET/CT imaging in cancer: current applications and future directions. Cancer. Nov. 15, 2014;120(22):3433-45. doi: 10.1002/cncr.28860. Epub Jun. 19, 2014. PMID: 24947987.

(56) References Cited

OTHER PUBLICATIONS

Gootenberg et al., Multiplexed and portable nucleic acid detection platform with Cas13, Cas12a, and Csm6. Science. Apr. 27, 2018;360(6387):439-444. doi: 10.1126/science.aaq0179. Epub Feb. 15, 2018.

Hao et al., CRISPR-Cas-amplified urine biomarkers for multiplexed and portable cancer diagnostics. bioRxiv Jun. 17, 2020.

Jambunathan et al., Prolyl endopeptidase activity in bronchoalveolar lavage fluid: a novel diagnostic biomarker in a guinea pig model of invasive pulmonary aspergillosis. Med Mycol. Aug. 2013;51(6):592-602. doi: 10.3109/13693786.2012.761360. Epub Jan. 28, 2013.

Klan et al., Photoremovable protecting groups in chemistry and biology: reaction mechanisms and efficacy. Chem Rev. Jan. 9, 2013;113(1):119-91. doi: 10.1021/cr300177k. Epub Dec. 21, 2012. PMID: 23256727; PMCID: PMC3557858.

Longo et al., In Vivo Imaging of Tumor Metabolism and Acidosis by Combining PET and MRI-CEST pH Imaging. Cancer Res. Nov. 15, 2016;76(22):6463-6470. doi: 10.1158/0008-5472.CAN-16-0825. Epub Sep. 20, 2016. PMID: 27651313.

Loynachan et al., Renal clearable catalytic gold nanoclusters for in vivo disease monitoring. Nat Nanotechnol. Sep. 2019;14(9):883-890. doi: 10.1038/s41565-019-0527-6. Epub Sep. 2, 2019. PMID: 31477801; PMCID: PMC7045344.

Rashidian et al., Noninvasive imaging of immune responses. Proc Natl Acad Sci U S A. May 12, 2015;112(19):6146-51. doi: 10.1073/pnas.1502609112. Epub Apr. 20, 2015. Erratum in: Proc Natl Acad Sci U S A. Jul. 3, 2018;115(27):E6387. PMID: 25902531; PMCID: PMC4434737.

Rashidian et al., Predicting the response to CTLA-4 blockade by longitudinal noninvasive monitoring of CD8 T cells. J Exp Med. Aug. 7, 2017;214(8):2243-2255. doi: 10.1084/jem.20161950. Epub Jun. 30, 2017. PMID: 28666979; PMCID: PMC5551571.

Soleimany et al., Activity-Based Diagnostics: An Emerging Paradigm for Disease Detection and Monitoring. Trends Mol Med. May 2020;26(5):450-468. doi: 10.1016/j.molmed.2020.01.013. Epub Apr. 5, 2020. PMID: 32359477; PMCID: PMC8290463.

Sun et al., A PET imaging approach for determining EGFR mutation status for improved lung cancer patient management. Sci Transl Med. Mar. 7, 2018;10(431):eaan8840. doi: 10.1126/scitranslmed. aan8840. PMID: 29515002.

Weerakkody et al., Family of pH (low) insertion peptides for tumor targeting. Proc Natl Acad Sci U S A. Apr. 9, 2013;110(15):5834-9. doi: 10.1073/pnas.1303708110. Epub Mar. 25, 2013. PMID: 23530249; PMCID: PMC3625278.

U.S. Appl. No. 17/124,999, filed Dec. 17, 2020, Bhatia et al.

Yoo et al., 2'-O-methyl-modified phosphorothioate antisense oligonucleotides have reduced non-specific effects in vitro. Nucleic Acids Res. Apr. 2, 2004;32(6):2008-16. doi: 10.1093/nar/gkh516. PMID: 15064360; PMCID: PMC390367.

Zinnhardt et al., Combined PET Imaging of the Inflammatory Tumor Microenvironment Identifies Margins of Unique Radiotracer Uptake. Cancer Res. Apr. 15, 2017;77(8):1831-1841. doi: 10.1158/0008-5472.CAN-16-2628. Epub Jan. 30, 2017. PMID: 28137769.

* cited by examiner

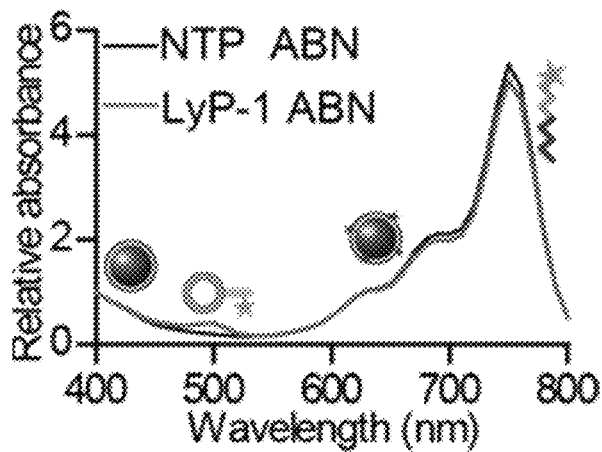
FIG. 5A
FIG. 5B
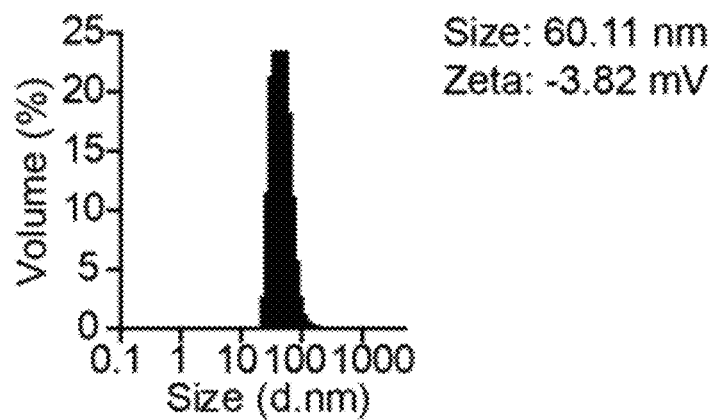
FIG. 5C 40 mm³ p32    α_v    NRP-1

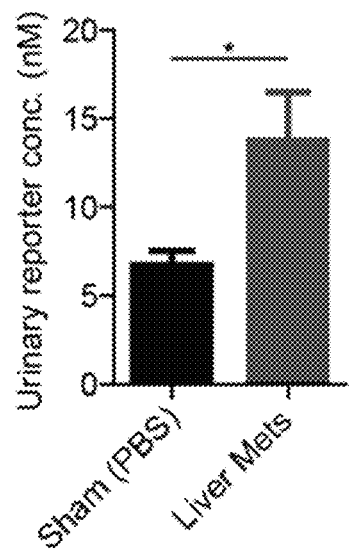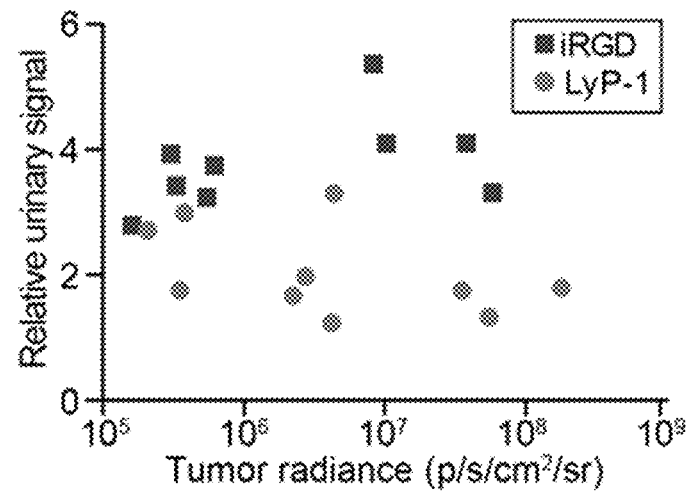
FIG. 19A    FIG. 19B
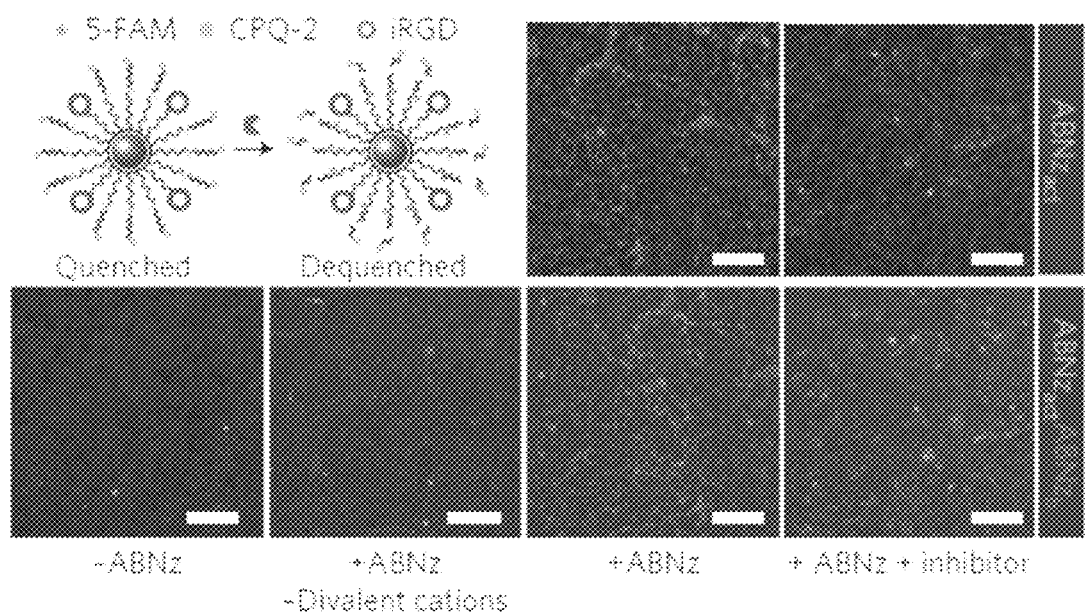
FIG. 20A

SEQUENCE LISTING

```
<160> NUMBER OF SEQ ID NOS: 23

<210> SEQ ID NO 1
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1

Cys Gly Asn Lys Arg Thr Arg Gly Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Polypeptide
```

```
<400> SEQUENCE: 2

Cys Arg Gly Asp Lys Gly Pro Asp Cys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 3

Ser Leu Lys Arg Tyr Gly Gly Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 4

Ala Ala Phe Arg Ser Arg Gly Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 5

Xaa Xaa Phe Arg Phe Phe Xaa Xaa
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 6

Gln Ser Val Gly Phe Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 7

Leu Gly Leu Glu Gly Ala Asp
1               5
```

```
<210> SEQ ID NO 8
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 8

Gly Pro Leu Asp
1

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 9

Leu Gly Val Leu Ile Val
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 10

Gly Leu Val Leu Val Ala
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 11

Pro Ala Ala Leu Val Gly
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 12

Gly Pro Ala Gly Leu Ala Gly
1               5

<210> SEQ ID NO 13
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 13

Gly Gly Pro Leu Gly Val Arg Gly Lys Lys
1               5                   10
```

```
<210> SEQ ID NO 14
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (3)..(3)
<223> OTHER INFORMATION: D steroisomer of Phe

<400> SEQUENCE: 14

Gly Gly Phe Pro Arg Ser Gly Gly Gly Lys
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 15

Pro Leu Gly Val Arg Gly Lys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MOD_RES
<222> LOCATION: (1)..(1)
<223> OTHER INFORMATION: D steroisomer of Phe

<400> SEQUENCE: 16

Phe Pro Arg Ser Gly Gly Gly
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
<221> NAME/KEY: misc_feature
<222> LOCATION: (10)..(11)
<223> OTHER INFORMATION: Modified with CPQ2-PEG2

<400> SEQUENCE: 17

Gly Gly Pro Leu Gly Val Arg Gly Lys Lys Cys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with 5FAM
<220> FEATURE:
```

```
<221> NAME/KEY: MOD_RES
<222> LOCATION: (3)..(3)
<223> OTHER INFORMATION: D stereoisomer of Phe
<220> FEATURE:
<221> NAME/KEY: misc_feature
<222> LOCATION: (10)..(11)
<223> OTHER INFORMATION: Modified with CPQ2-PEG2

<400> SEQUENCE: 18

Gly Gly Phe Pro Arg Ser Gly Gly Gly Lys Cys
1               5                   10

<210> SEQ ID NO 19
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with biotin
<220> FEATURE:
<221> NAME/KEY: misc_feature
<222> LOCATION: (10)..(11)
<223> OTHER INFORMATION: Modified with Cy7
<220> FEATURE:
<221> NAME/KEY: MOD_RES
<222> LOCATION: (11)..(11)
<223> OTHER INFORMATION: D stereoisomer of Glu
<220> FEATURE:
<221> NAME/KEY: MOD_RES
<222> LOCATION: (13)..(13)
<223> OTHER INFORMATION: D stereoisomer of Val
<220> FEATURE:
<221> NAME/KEY: MOD_RES
<222> LOCATION: (14)..(14)
<223> OTHER INFORMATION: D stereoisomer of Asn
<220> FEATURE:
<221> NAME/KEY: MOD_RES
<222> LOCATION: (15)..(15)
<223> OTHER INFORMATION: D stereoisomer of Asp
<220> FEATURE:
<221> NAME/KEY: mod_res
<222> LOCATION: (16)..(16)
<223> OTHER INFORMATION: D stereoisomer of Asn
<220> FEATURE:
<221> NAME/KEY: MOD_RES
<222> LOCATION: (17)..(17)
<223> OTHER INFORMATION: D stereoisomer of Glu
<220> FEATURE:
<221> NAME/KEY: MOD_RES
<222> LOCATION: (18)..(18)
<223> OTHER INFORMATION: D stereoisomer of Glu
<220> FEATURE:
<221> NAME/KEY: MOD_RES
<222> LOCATION: (20)..(20)
<223> OTHER INFORMATION: D stereoisomer of Phe
<220> FEATURE:
<221> NAME/KEY: MOD_RES
<222> LOCATION: (21)..(21)
<223> OTHER INFORMATION: D stereoisomer of Phe
<220> FEATURE:
<221> NAME/KEY: MOD_RES
<222> LOCATION: (22)..(22)
<223> OTHER INFORMATION: D stereoisomer of Ser
<220> FEATURE:
<221> NAME/KEY: MOD_RES
<222> LOCATION: (23)..(23)
<223> OTHER INFORMATION: D stereoisomer of Ala
<220> FEATURE:
<221> NAME/KEY: MOD_RES
<222> LOCATION: (24)..(24)
<223> OTHER INFORMATION: D stereoisomer of Arg

<400> SEQUENCE: 19
```

Cys Gly Pro Leu Gly Val Arg Gly Lys Lys Glu Gly Val Asn Asp Asn
1               5                   10                  15

Glu Glu Gly Phe Phe Ser Ala Arg
            20

<210> SEQ ID NO 20
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (2)..(3)
<223> OTHER INFORMATION: Modified with 5FAM-C6

<400> SEQUENCE: 20

Cys Lys Cys Gly Asn Lys Arg Thr Arg Gly Cys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(2)
<223> OTHER INFORMATION: Modified with PEG2

<400> SEQUENCE: 21

Cys Cys Arg Gly Asp Lys Gly Pro Asp Cys
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with (PEG)n

<400> SEQUENCE: 22

Gly Gly Pro Leu Gly Val Arg Gly Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Modified with (PEG)n
<220> FEATURE:
<221> NAME/KEY: MOD_RES
<222> LOCATION: (3)..(3)
<223> OTHER INFORMATION: D stereoisomer of Phe

<400> SEQUENCE: 23

Gly Gly Phe Pro Arg Ser Gly Gly Gly
1               5

METHODS TO SPATIALLY PROFILE PROTEASE ACTIVITY IN TISSUE AND SECTIONS

RELATED APPLICATIONS

This application claims priority under 35 U.S.C. § 119(e) to U.S. Provisional Application Ser. No. 62/483,245, filed Apr. 7, 2017, the contents of which are incorporated herein by reference in its entirety for all purposes.

FIELD

The disclosure relates, in some aspects, to improved methods and products associated with detecting, localizing, and monitoring the activity of proteases in vivo or in vitro. These methods and products form the basis of, and may be used as, an ultrasensitive diagnostic platform.

BACKGROUND

Early detection of tumors offers the hope of greatly improved outcomes for cancer patients. For the majority of cancer types, diagnosis when the disease is localized to the organ of origin correlates with significantly greater long-term survival compared with when the disease has spread to distant sites, largely because currently available therapeutics are most effective when patients are treated in the early stages of disease. Despite the need for technology that can detect early-stage disease, the predictive value of existing biomarkers used to diagnose cancers is limited. For example, researchers have observed that screening with the blood biomarker CA-125 for ovarian cancer diagnosis does not improve patient prognosis. However, screening with biomarkers that are predictive can significantly improve patient outcomes: colorectal cancer (CRC) mortality at 30-year follow-up was reduced by 32% with annual fecal occult-blood testing.

Despite the progress in improving tumor detection tools, clinical detection of tumors is limited to masses ~1 cm in diameter via imaging techniques (for example, magnetic resonance imaging (MRI) and positron emission tomography) and analysis of blood biomarkers shed by the tumor (for example, proteins and cell-free nucleic acids). It is estimated that it can take up to ten years to establish tumors this size from the initial tumorigenesis, leaving a large window of opportunity for early diagnosis to improve patient outcomes.

SUMMARY

Aspects of the disclosure relate to the surprising discovery that pro-diagnostic reagents comprising certain modifications (e.g., surface presentation of enzyme susceptible domains, functionalization with a tumor-penetrating ligand, or a combination thereof) are capable of improved in situ localization of enzymatic activity in tissue samples. In some aspects, the disclosure relates to the surprising discovery that pro-diagnostic reagents described herein are capable of detecting tumors (e.g., enzymatic activity associated with a tumor) having a size less than 1 cm in diameter, which is below the limit of detection of previously utilized activity-based monitoring molecules, in vivo.

Accordingly, in some aspects, the disclosure provides a pro-diagnostic reagent comprising: (a) a carrier domain linked to a signature producing domain, wherein the signature producing domain comprises an enzyme susceptible domain linked to a signature molecule, wherein the enzyme susceptible domain is susceptible to cleavage by a disease-associated enzyme, and, (b) one or more tumor-penetrating ligands, wherein each tumor-penetrating ligand is linked to the carrier domain.

In some embodiments, a carrier domain is greater than 5 nm in size. In some embodiments, a carrier domain is smaller than 5 nm in size.

In some embodiments, a carrier domain is a nanoparticle, arginine/glycine/aspartic acid (RGD) peptide, protein, polymer, aptamer, or antibody. In some embodiments, a carrier domain is an iron-oxide nanoparticle.

In some embodiments, a carrier domain is linked to the signature producing domain by a linker molecule. In some embodiments, a linker molecule comprises one or more poly(ethylene glycol) (PEG) molecules. In some embodiments, a linker molecule comprises between 2 and 200 PEG molecules.

In some embodiments, an enzyme susceptible domain is susceptible to cleavage by an enzyme associated with cancer, tissue injury or damage, cardiovascular disease, arthritis, viral, bacterial, parasitic or fungal infection, Alzheimer's disease emphysema, thrombosis, hemophilia, stroke, organ dysfunction, any inflammatory condition, vascular disease, parenchymal disease, or a pharmacologically-induced state.

In some embodiments, a disease-associated enzyme is a seine protease, matrix metalloprotease (MMP), thrombin, kallikrein, matriptase, hepsin, cathepsin, plasminogen activator, or A Disintegrin And Metalloprotease (ADAM).

In some embodiments, a signature molecule is a peptide, nucleic acid, small molecule, fluorophore (e.g., a fluorophore, or a fluorophore/quencher pair, such as a FRET pair), carbohydrate, particle, radiolabel. MRI-active compound, ligand encoded reporter, or isotope coded reporter molecule (iCORE).

In some embodiments, a signature molecule comprises a fluorescence resonance energy transfer (FRET) pair. In some embodiments, a FRET pair comprises a fluorophore molecule and a quenching molecule. In some embodiments the fluorophore molecule and the quenching molecule of a FRET pair flank an enzyme susceptible domain of a pro-diagnostic reagent as described by the disclosure. In some embodiments, a quenching molecule is proximal to a carrier domain relative to a fluorophore molecule. In some embodiments, a fluorophore molecule is proximal to a carrier domain relative to a quencher molecule. In some embodiments, a FRET pair is 5-Carboxyfluorescein (5-FAM) and CPQ2.

In some embodiments, a signature molecule is a fluorophore. In some embodiments, a signature molecule is an iCORE. In some embodiments, a signature molecule is cyanine7 (Cy7).

In some embodiments, a tumor-penetrating ligand is a peptide, polypeptide (e.g., antibody), polymer, aptamer, or small molecule. In some embodiments, a tumor-penetrating ligand specifically binds to a p32 receptor, neuropilin-1 (NRP1) receptor, αvβ3 integrin receptor, αvβ5 integrin receptor, folate receptor, transferrin receptor, Her2 receptor, or EGFR. In some embodiments, a tumor-penetrating ligand is LyP-1 (CGNKRTRGC; SEQ ID NO: 1) or iRGD (CRGDKGPDC; SEQ ID NO: 2).

In some embodiments, a tumor-penetrating ligands is linked to a carrier domain by a linker molecule. In some embodiments, a linker molecule comprises one or more poly(ethylene glycol) (PEG) molecules. In some embodiments, a linker molecule comprises between 2 and 200 PEG molecules.

In some embodiments, a carrier domain comprises a plurality of enzyme susceptible domains, a plurality of ligands capable of binding to the tissue sample, or a combination thereof.

In some aspects, the disclosure provides a method for determining the location of disease-associated enzyme activity in a tissue sample, the method comprising: (a) contacting a tissue sample obtained from a subject with a pro-diagnostic reagent, wherein the pro-diagnostic reagent comprises: (i) a carrier domain linked to a signature producing domain, wherein the signature producing domain comprises an enzyme susceptible domain linked to a signature molecule, wherein the enzyme susceptible domain is susceptible to cleavage by a disease-associated enzyme, and, (ii) one or more ligands capable of binding to the tissue sample, wherein each ligand is linked to the carrier domain; wherein the one or more ligands bind the carrier domain to the biological sample prior to cleavage of the enzyme susceptible domain by the disease-associated enzyme; and, (b) subjecting the tissue sample to an analysis method in order to detect the presence of the signature molecule, wherein the presence of the signature molecule in the tissue sample is indicative of the location of disease-associated enzymatic activity within the tissue sample.

In some embodiments, a subject is a mammal, such as a human. In some embodiments, to a tissue sample is a flash-frozen tissue sample. In some embodiments, a tissue sample is obtained from the brain, lymph node, breast, liver, pancreas, colon, liver, lung, blood, skin, ovary, prostate, kidney, or bladder of a subject. In some embodiments, a tissue sample comprises cancer cells.

In some embodiments, an analysis method is a multiplex analysis method. In some embodiments, an analysis method involves mass spectrometry (such as liquid chromatography-mass spectrometry), PCR analysis, DNA microarray, fluorescence analysis, or ELISA. In some embodiments, an analysis method is a singular analysis method.

In some aspects, the disclosure provides a method for detecting a tumor in a subject, the method comprising (i) administering to a subject a pro-diagnostic reagent, wherein the pro-diagnostic reagent comprises (a) a carrier domain linked to a signature producing domain, wherein the signature producing domain comprises an enzyme susceptible domain linked to a signature molecule, wherein the enzyme susceptible domain is susceptible to cleavage by a cancer-associated enzyme, and, (b) one or more tumor-penetrating ligands, wherein each tumor-penetrating ligand is linked to the carrier domain; (ii) subjecting a biological sample obtained from the subject to an analysis method in order to detect the presence of the signature molecule, wherein the presence of the signature molecule in the biological sample is indicative of the subject having a tumor.

In some embodiments of methods described herein, a pro-diagnostic reagent is administered to a subject via a systemic modality, such as intravenous injection.

In some embodiments, a tumor detected by a method described by the disclosure is less than about 1 cm in diameter. In some embodiments, a tumor detected by a method described by the disclosure is between about 1 mm and about 5 mm in diameter.

In some embodiments, a biological sample is a urine sample or a blood sample. In some embodiments, the signature molecule is cleaved form the enzyme susceptible domain at a site that is remote from the biological sample.

BRIEF DESCRIPTION OF DRAWINGS

FIG. 1A shows analysis of fold change in MMP9 mRNA expression in tumors versus healthy controls; compiled from Oncomine and TCGA data. H&N, head and neck; Mela, melanoma; OV, ovarian; GBM, glioblastoma multiforme; COAD, colorectal adenocarcinoma. FIG. 1B shows ROC curves constructed on the basis of MMP9 mRNA expression data to represent how well MMP9 can classify various cancer types versus healthy controls (median AUC=0.81). FIGS. 1C and 1D show immunohistochemical staining of MMP9 protein in normal (Norm) and ovarian carcinoma from a human TMA (FIG. 1C) and corresponding staining scores for tumor (n=20 cores) versus normal (n=5 cores) tissue (FIG. 1D). Blinded analysis of staining was performed by a pathologist; 3 for the highest level of staining and 0 for no visible staining. FIGS. 1E and 1F show immunohistochemical staining of MMP9 protein in normal colon and COAD from a TMA (FIG. 1E) and corresponding expression scores (FIG. 1F). Full TMA staining is shown in FIG. 2D.

FIG. 2A shows mRNA expression of MMP9 is elevated in breast cancer samples compared to normal adjacent tissue based on analysis from The Cancer Genome Atlas. FIG. 2B shows MMP9 mRNA is elevated across all stages of breast cancer compared to normal adjacent tissue based on analysis. FIG. 2C shows scoring of MMP9 staining in tumor and normal tissue from ovarian, breast, lung, and prostate. Cores were scored by a pathologist in a blind manner.

FIG. 2D shows a scan of tumor microarray stained with MMP9 antibody. Tumor microarray was purchased from US BioMax, Inc. (Catalog No. MC5003b). FIG. 2E shows several MMPs showed significantly upregulated expression across breast cancer stages compared to normal adjacent tissue (Two-tail Student's t test for a; 1 way ANOVA with Dunnet's posttest for FIG. 2B & FIG. 2E; *P<0.05, P<0.01, *P<0.001; n=22 for normal, 39 for Stage I, 42 for Stage Ia, 9 for Stage Ib, 26 for Stage II, 164 for Stage IIa, 103 for Stage IIb, 10 for Stage III, 65 for Stage IIIa, 13 for Stage IIIb, 19 for Stage IIIc, 13 for Stage IV, 9 for Stage X).

FIG. 3A shows a schematic depicting FRET-based protease substrate displayed on an ABN surface. The sequence corresponds to SEQ ID NO: 22. FIG. 3B and FIG. 3C show cleavage velocity (V) of an MMP9 substrate by MMP9 (FIG. 3B) or thrombin (FIG. 3C) for 0, 4, 24 and 114 PEG subunits. Lines represent the fit to the Michaelis-Menten equation (mean+s.e.m., n=2-3). FIG. 3D shows the ratio of MMP9 and thrombin velocities at a substrate concentration of 6 µM (RFU, relative fluorescence units). FIGS. 3E-3G show accumulation of LyP-1 ABNs and NTP ABNs (controls) in excised tumors (FIG. 3E) and quantification of ABN signal in tumors (FIG. 3F) and organs (FIG. 3G); mean+s.e.m, n=7 for NTP ABNs and n=8 for Lyp-1 ABNs. FIG. 3H shows a schematic of parameters varied in a mathematical pharmacokinetic model. FIG. 3I and FIG. 3J show change in detection signal when optimized parameters (BC, background cleavage; TC, tumoral cleavage; TA, tumoral accumulation) were applied to 10-mm (FIG. 3I) versus 5-mm (FIG. 3J) tumors (light shading denotes additional signal gained when parameters are combined, compared with BC+TC+TA).

FIG. 3K shows kinetic traces of the detected urine signal (tumor−control) with all three parameters optimized (left line), and the contribution to the signal of increasing the TA term (right line).

FIGS. 5A-5C show characterization of targeted vs untargeted nanoparticles. FIG. 5A shows spectra of LyP-1 and non-tumor penetrating (NTP) ABN. Iron oxide absorbs at wavelengths shorter than 400 nm, LyP-1 is tagged with 5FAM dye, the nanoparticle core is labeled with VT-680 and the peptide substrate is labeled with Cy7. FIG. 5B shows peptide substrate valencies were matched between the two nanoparticles. FIG. 5C shows physicochemical characterization of particles by dynamic light scattering shows a hydrodynamic diameter of 60.11 nm and a surface potential of −3.82 mV.

FIG. 6A shows a schematic depicting urine testing in a mouse flank tumor (MDA-MB-435 xenograft) model; i.v., intravenous. Study time course for urine testing is also shown. FIG. 6B and FIG. 6C show relative reporter concentrations in the urine normalized to urine signal in healthy mice after administration of NTP ABNs (FIG. 6B; mean tumor size for 50+ bin, 146 mm$^3$) and LyP-1 ABNs (FIG. 6C; mean tumor size for 50+ bin, 132 mm$^3$). Tumors from seven (NTP ABNs) or eight (LyP-1 ABNs) mice measured over three weeks were binned by tumor size; mean±s.e.m., two-tailed Student's t-test, *$P<0.05$, **$P<0.01$; p is the Spearman correlation between urine signal and tumor size in individual mice. FIG. 6D and FIG. 6E show ROC curves and calculated AUC values for NTP ABNs (control; FIG. 6D) and LyP-1 ABNs (FIG. 6E).

FIG. 7A shows blood half-lives of LyP-1 and non-penetrating particles are matched (data fit to one-phase to exponential decay). FIG. 7B shows kinetic measurement of the free reporter in the blood and urine after intravenous injection.

FIG. 8A shows caliper measurements of tumor sizes across both groups were consistent, reaching 100 mm$^3$ total burden by week 3. FIG. 8B shows a histogram of tumor sizes for urine data binning. FIG. 8C shows photographs of flank tumors in nude mice. Targeted synthetic biomarkers were able to classify tumors at week 2. Volumes reported are calculated after measurements performed using a digital caliper. Urine signal for mice administered (FIG. 8D) non-penetrating ABNs and (FIG. 8E) LyP-1 ABNs over time course of the study (P-value represented on each graph as calculated by repeated measures ANOVA) are also shown.

FIG. 9A shows a schematic of LyP-1 ABN testing in an ovarian cancer model. FIG. 9B shows immunohistochemical staining of excised tumors (scale bars, 100 µm). FIG. 9C shows size distribution of tumor nodules retrieved from the intraperitoneal space of a representative animal at two weeks after tumor initiation. Average total tumor burden at this time point was 36 mm$^3$.

FIG. 9D and FIG. 9E show accumulation of ABNs in tumor nodules in a representative animal (FIG. 9D; scale bar, 1 cm) and biodistribution of ABNs in organs (FIG. 9E; mean+s.e.m, n=10). FIG. 9F shows urinary measurements of ABNs (bars) and blood measurements of HE4 (black line); mean±s.e.m, n=10 per group, two-tailed Student's t-test, ***$P<0.001$). FIG. 9G shows a ROC curve of urinary diagnostic and blood biomarker.

FIG. 10A shows a standard curve for the HE4 ELISA. FIG. 10B shows secreted HE4 across several lines was measured by collecting supernatants. Data is normalized to get secretion rate per million cells per day. FIG. 10C shows cytoplasmic HE4 was measured by collecting and lysing cells. OVCAR-8 cells have relatively high secretion and cytoplasmic HE4 compared to cells profiled.

FIG. 10D shows cleavage of MMP9 substrate by conditioned media collected from OVCAR-8 cells with and without the MMP inhibitor, Marimistat. Marimistat can inhibit a significant portion of the cleavage. FIG. 10E shows correlation of tumor volumes as measured by imaging of retrieved nodules after necropsy versus bioluminescence imaging. FIG. 10F shows bioluminescence imaging shows that on average, tumor burden increases over time.

FIG. 11A shows a plot of LyP-1 ABN accumulation, as measured by fluorescence intensity, and tumor diameter from the 10 mice shown in FIG. 9F. Linear regression shows that total nanoparticle accumulation was correlated with size of individual tumor nodules (Pearson's r=0.767). FIG. 11B shows total tumor burden was measured at the time when detection became statistically significant for blood biomarker (n=10, 3 weeks; HE4) or for the urinary biomarker (n=10, 2 weeks). The limit of detection for LyP-1 ABN was at a tumor volume of 36 mm$^3$ while the limit of detection for blood biomarker HE4 was at a tumor volume of 88 mm$^3$. FIG. 11C shows distribution of nodule diameters recovered from each mouse at time of positive detection (n=10 each group). FIG. 11D shows tumor and non-tumor mice were imaged live (top), then sacrificed and the abdominal cavities opened to image tumors without skin attenuation (middle). Visible tumors were resected and mice were imaged again (bottom). FIG. 11E shows luminescence from tumor bearing mice before and after tumor resection was measured, and it was calculated that 17.4% and 17.8% of tumor signal was remaining, respectively. FIG. 11F shows resected tissue is luminescent, suggesting that mostly tumor cells were removed. FIG. 11G shows cell standard OVCAR-8 cells was also imaged, with a limit of detection below 3,000 cells.

FIG. 12A shows LyP-1 and iRGD both engage the same tumor trafficking pathway but rely on different primary receptors. LyP-1 and iRGD ABNs were tested in a liver metastasis model. The sequences correspond to LyP-1 (CGNKRTRGC; SEQ ID NO: 1) and iRGD (CRGDKGPDC; SEQ ID NO: 2). FIG. 12B shows a MRI image of a CLM mouse with 40 mm3 of total tumor burden; tumor nodules are indicated by arrows. FIG. 12C shows Haemotoxylin and Eosin staining (scale bar, 5 mm) and immunohistochemical staining of tumor sections for the primary receptors, p32 and αv integrin, and the secondary receptor, NRP-1 (scale bar, 200 µm). FIG. 12D shows imaging of tumor center and margin, as well as normal liver, in sections from CLM mice. The tumor margin is indicated by a dashed line and the inset is indicated by, a box. Sections were stained for nuclei and MMP9; scale bar, 100 µm. FIG. 12E shows bioluminescence imaging of CLM mice over time (mean t s.e.m, n=20). ABNs were administered when luminescence readings reached 107 photons s−1 cm−2 sr−1. FIG. 12F shows fluorescent scans of tumors showing ABN accumulation (left scale bar, 2 cm; right scale bars, 5 mm) and line traces of ABN and liver autofluorescence (in relative fluorescence units) corresponding to the dashed lines. FIG. 12G shows relative reporter concentrations measured in to the urine of healthy mice versus CLM mice after application of LyP-1 ABNs (n=10 mice) or iRGD ABNs (n=9 mice); the mean s.e.m is denoted by a horizontal line with error bars; two-tailed Student's t-test, ***P<0.001.

FIG. 13A shows MC26 cells in culture express integrins. FIG. 13B shows MC26 cells in culture express Neuropilin-1. FIG. 13C shows that MC26 cells in culture do not express p32. Traces indicating IgG control for each sample are also shown.

FIG. 14A shows absorbance spectra of iRGD ABNz. Spectra matches LyP-1 ABNz, except iRGD does not have a FAM label. FIG. 14B shows mouse MMP9 is readily able to cleave the selected MMP9 substrate.

FIG. 15C shows organs were collected 3 hours, 24 hours, and 7 days after ABN administration and fluorescence was measured compared to a PBS injected control. Reporter signal in the blood, urine, and organs was undetectable at 7 days (n=3, +SEM for all time points). FIG. 15D shows nude mice bearing orthotopic ovarian tumors and injected with ABN have similar urine clearance kinetics with no detectable signal after 1 day (n=5, ±SEM).

FIG. 18A shows biodistribution of LyP-1 or iRGD targeted nanoparticles. FIG. 18B shows a fluorescent scan of livers with tumor metastases administered iRGD or LyP-1 targeted synthetic biomarkers or uninjected controls. Scale bar indicates 2 cm. Uninjected controls show no nanoparticle fluorescence. Tumors are not autofluorescent (arrow). FIG. 18C shows photographs of excised livers. Tumors are delineated by lack of autofluorescence.

FIGS. 19A-19B show performance of targeted nanosensors in liver metastasis model. FIG. 19A shows iRGD targeted sensors can differentiate liver metastasis bearing mice from age-matched mice that received a sham surgery (n=5 per condition; ±SEM; Student's t-test, two-tailed, *P<0.05). FIG. 19B shows a plot of an individual mouse relative urinary signal against tumor luminescence. Tumor luminescence between iRGD and LyP-1 groups were similar.

FIGS. 20A-20E show ABN zymography is responsive to human tissues. FIG. 20A shows a schematic of ABNs re-engineered for zymography (ABNz). Nanoparticles were modified with iRGD targeting ligands and FRET-pair flanked substrates that increase their fluorescence on proteolytic cleavage. Frozen sections of CLM livers collected from mice were bound with PBS only (–ABNz), ABNz without divalent cations necessary for iRGD binding, and ABNz. Tissues were subsequently cleaved in MMP9 buffer with and without MMP9 inhibitor and imaged for the bound ABNz (ABNzb) and cleaved ABNz (ABNzact); scale bars, 50 µm. FIG. 20B shows application of iRGD ABNz to a human CRC tumor microarray consisting of 20 colorectal adenocarcinoma (COAD) samples and 20 normal adjacent tissue (NAT) (scale bar, 2 mm). FIG. 20C shows extent of signal co-localization between COAD and NAT samples scored on a scale of 0 to 3 by a blinded independent researcher. FIG. 20D shows a higher-magnification image of the boxed area in FIG. 20B showing a patient sample containing cancer (left) and normal adjacent tissue (right); scale bar, 400 µm. FIG. 20E shows magnified tissue from boxed area in FIG. 20D showing cell-level co-localization of activated ABNz with integrin and MMP9 staining (scale bar, 40 µm).

DETAILED DESCRIPTION

Figure 1A:
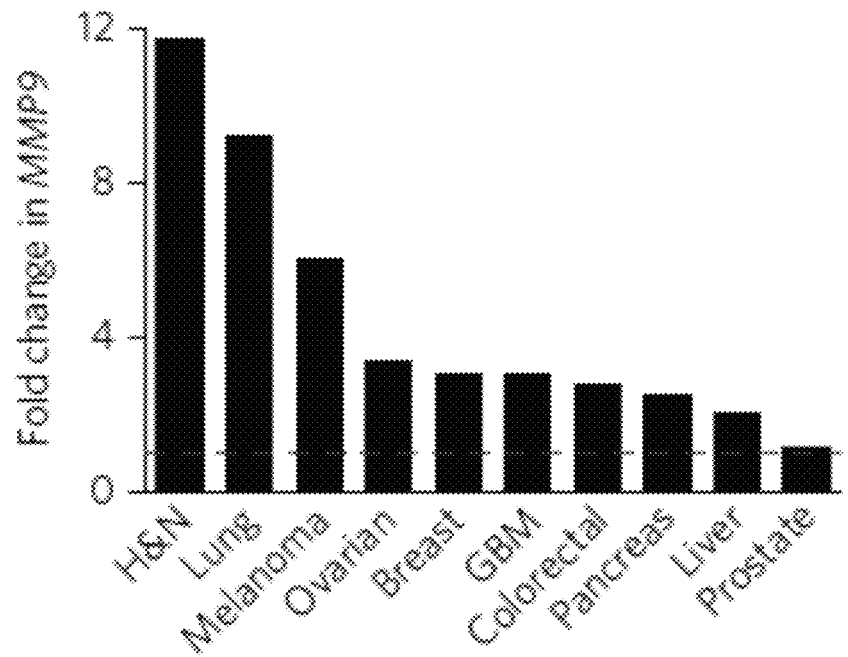
FIGS. 1A-1F show MMP9 is upregulated across human cancers.

Current approaches to measure protease activity in tissue sections rely on measuring cleavage of fluorescently labelled protein gels overlaid on the tissue. Other approaches involve directly binding active proteases, either using antibodies that bind the active site of the protease of interest or activity-based probes that covalently bind to active proteases, for example as disclosed in WO2014/0255313. The evaluation of substrate cleavage in tissue sections using the approaches mentioned above presents several challenges. For example, substrate typically diffuses away from the location of the active protease. Furthermore, currently available activity-based probes are typically unable to detect tumors that are less than 1 cm in diameter.

The compositions and methods of the disclosure have a number of advantages over the prior art methods. For example, compositions and methods described by the disclosure are useful, in some embodiments, for localizing enzyme substrate to a tissue prior to proteolysis, as opposed to enabling tissue binding after proteolysis, and then measuring protease activity on the substrate (e.g. measuring enzymatic activity in situ on a tissue sample). In another example, pro-diagnostic reagents comprising one or more ligands that bind to a tissue (e.g., tumor-penetrating ligands) greatly increase the sensitivity of pro-diagnostic reagents described by the disclosure, thus making them capable of detecting tumors that are less than 5 mm in diameter.

Accordingly, in some aspects, the disclosure provides a pro-diagnostic reagent comprising: (a) a carrier domain linked to a signature producing domain, wherein the signature producing domain comprises an enzyme susceptible domain linked to a signature molecule, wherein the enzyme susceptible domain is susceptible to cleavage by a disease-associated enzyme, and, (b) one or more tumor-penetrating ligands, wherein each tumor-penetrating ligand is linked to the carrier domain.

Carrier Domain

A pro-diagnostic reagent as described by the disclosure typically comprises a modular structure having a carrier domain linked to an enzyme susceptible detectable marker. As used herein, the pro-diagnostic agent is non-natural (i.e., synthetic). A modular structure, as used herein, refers to a molecule having multiple domains.

The carrier domain may include a single type of enzyme susceptible detectable marker, such as, a single type of enzyme susceptible domain and/or detectable marker or it may include multiple type of enzyme susceptible detectable markers, such as, different enzyme susceptible domains and detectable markers. For instance each carrier may include one type of enzyme susceptible detectable marker or it may include 2-1,000 different enzyme susceptible detectable markers or any integer therebetween. Alternatively each carrier may include greater than 1,000 enzyme susceptible detectable markers. Multiple copies of the pro-diagnostic reagent are administered to the subject. Some mixtures of pro-diagnostic reagents may include enzyme susceptible detectable markers that are enzymes, others may be enzymatic susceptible domains, and other may be mixtures of the two. Additionally a plurality of different pro-diagnostic reagents may be administered to the subject to determine whether multiple enzymes and/or substrates are present. In that instance, the plurality of different pro-diagnostic reagents includes a plurality of detectable markers, such that each enzyme susceptible domain is associated with a particular detectable marker or molecules.

The carrier domain may serve as the core of the nanoparticle. A purpose of the carrier domain is to serve as a platform for the enzyme susceptible detectable marker. As such, the carrier can be any material or size as long as it can serve as a carrier or platform. Preferably the material is non-immunogenic, i.e. does not provoke an immune response in the body of the subject to which it will be administered. Another purpose is that it may function as a targeting means to target the modular structure to a tissue, cell or molecule. In some embodiments the carrier domain is a particle. A particle, for example, a nanoparticle, may, for instance, result in passive targeting to tumors by circulation. Other types of carriers, include, for instance, compounds that cause active targeting to tissue, cells or molecules. Examples of carriers include, but are not limited to, microparticles, nanoparticles, aptamers, peptides (RGD, iRGD, LyP-1, CREKA, etc.), proteins, nucleic acids, polysaccharides, polymers, antibodies or antibody fragments (e.g., herceptin, cetuximab, panitumumab, etc.) and small molecules (e.g., erlotinib, gefitinib, sorafenib, etc.).

As used herein the term "particle" includes nanoparticles as well as microparticles. Nanoparticles are defined as particles of less than 1.0 µm in diameter. A preparation of nanoparticles includes particles having an average particle size of less than 1.0 µm in diameter. Microparticles are particles of greater than 1.0 µm in diameter but less than 1 mm. A preparation of microparticles includes particles having an average particle size of greater than 1.0 µm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments the diameter is about 5 nm to about 500 nm. In other embodiments, the diameter is about 100 nm to about 200 nm. In other embodiment, the diameter is about 10 nm to about 100 nm.

The particles may be composed of a variety of materials including iron, ceramic, metallic, natural polymer materials (including lipids, sugars, chitosan, hyaluronic acid, etc.), synthetic polymer materials (including poly-lactide-coglycolide, poly-glycerol sebacate, etc.), and non-polymer materials, or combinations thereof.

The particles may be composed in whole or in part of polymers or non-polymer to materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxyapatite, tricalcium phosphate, dicalcium phosphate, tricalcium phosphate, tetracalcium phosphate, amorphous calcium phosphate, octacalcium phosphate, and silicates. In certain embodiments the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide.

A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, Acc. Chem. Res. 33:94, 2000; Langer, J. Control Release 62:7, 1999; and Uhrich et al., Chem. Rev. 99:3181, 1999; all of which are incorporated herein by reference).

Polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as algninate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyethylene glycol (PEG), also known as poly(oxyethylene) glycol, is a condensation polymer of ethylene oxide and water having the general chemical formula $HO(CH_2CH_2O)[n]H$.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, PVA and PVP are commercially available from chemical suppliers such as the Sigma Chemical Company (St. Louis, Mo.).

In certain embodiments the particles may comprise poly (lactic-co-glycolic acid) (PLGA).

The carrier may be composed of inorganic materials. Inorganic materials include, for instance, magnetic materials, conductive materials, and semiconductor materials.

In addition to particles the carrier may be composed of any organic carrier, including biological and living carriers such as cells, viruses, bacteria, as well as any non-living organic carriers, or any composition enabling exposure of enzyme substrates to enzymes in disease (including extracellular, membrane-bound, and intracellular enzymes).

In some embodiments, the particles are porous. A porous particle can be a particle having one or more channels that extend from its outer surface into the core of the particle. In some embodiments, the channel may extend through the particle such that its ends are both located at the surface of the particle. These channels are typically formed during synthesis of the particle by inclusion followed by removal of a channel forming reagent in the particle.

The size of the pores may depend upon the size of the particle. In certain embodiments, the pores have a diameter of less than 15 microns, less than 10 microns, less than 7.5 microns, less than 5 microns, less than 2.5 microns, less than 1 micron, less than 0.5 microns, or less than 0.1 microns. The degree of porosity in porous particles may range from greater than 0 to less than 100% of the particle volume. The degree of porosity may be less than 1%, less than 5%, less than 10%, less than 15%, less than 20%, less than 25%, less than 30%, less than 35%, less than 40%, less than 45%, or less than 50%. The degree of porosity can be determined in a number of ways. For example, the degree of porosity can be determined based on the synthesis protocol of the carriers (e.g., based on the volume of the aqueous solution or other channel-forming reagent) or by microscopic inspection of the carriers post-synthesis.

The plurality of particles may be homogeneous for one or more parameters or characteristics. A plurality that is homogeneous for a given parameter, in some instances, means that particles within the plurality deviate from each other no more than about +/−10%, preferably no more than about +/−5%, and most preferably no more than about +/−1% of a given quantitative measure of the parameter. As an example, the particles may be homogeneously porous. This means that the degree of porosity within the particles of the plurality differs by not more than +/−10% of the average porosity. In other instances, a plurality that is homogeneous means that all the particles in the plurality were treated or processed in the same manner, including for example exposure to the same agent regardless of whether every particle ultimately has all the same properties. In still other embodiments, a plurality that is homogeneous means that at least 80%, preferably at least 90%, and more preferably at least 95% of particles are identical for a given parameter.

The plurality of particles may be heterogeneous for one or more parameters or characteristics. A plurality that is heterogeneous for a given parameter, in some instances, means that particles within the plurality deviate from the average by more than about +/−10%, including more than about +/−20%. Heterogeneous particles may differ with respect to a number of parameters including their size or diameter, their shape, their composition, their surface charge, their degradation profile, whether and what type of agent is comprised by the particle, the location of such agent (e.g., on the surface or internally), the number of agents comprised by the particle, etc. The invention contemplates separate synthesis of various types of particles which are then combined in any one of a number of pre-determined ratios prior to contact with the sample. As an example, in one embodiment, the particles may be homogeneous with respect to shape (e.g., at least 95% are spherical in shape) but may be heterogeneous with respect to size, degradation profile and/or agent comprised therein.

Particle size, shape and release kinetics can also be controlled by adjusting the particle formation conditions. For example, particle formation conditions can be optimized to produce smaller or larger particles, or the overall incubation time or incubation temperature can be increased, resulting in particles which have prolonged release kinetics.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells.

To enhance delivery the particles may be incorporated, for instance, into liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFECTIN™ (commercially available cationic liposomes comprising DOTMA and DOPE, from GIBCO/BRL, Grand Island, N.Y., USA); LIPOFECTAMINE™) (commercially available cationic liposomes comprising DOSPA and DOPE, from GIBCO/BRL); and TRANSFECTAM™ (commercially available cationic lipids comprising DOGS in ethanol from Promega Corp., Madison, Wis., USA). A variety of methods are available for preparing liposomes e.g., U.S. Pat. Nos. 4,186,183, 4,217,344, 4,235,871, 4,261,975, 4,485, 054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradable food based particles such as cellulose.

The carrier domain can serve several functions. As discussed above, it may be useful for targeting the product to a specific region, such as a tissue. In that instance it could include a targeting agent such as a glycoprotein, an antibody, or a binding protein.

Further, the size of the carrier domain may be adjusted based on the particular use of the pro-diagnostic reagent. For instance, the carrier domain may be designed to have a size greater than 5 nm. Particles, for instance, of greater than 5 nm are not capable of entering the urine, but rather, are cleared through the reticuloendothelial system (RES; liver, spleen, and lymph nodes). By being excluded from the removal through the kidneys any uncleaved pro-diagnostic reagent will not be detected in the urine during the analysis step. Additionally, larger particles can be useful for maintaining the particle in the blood or in a tumor site where large particles are more easily shuttled through the vasculature. In some embodiments the carrier domain is 500 microns-5 nm, 250 microns-5 nm, 100 microns-5 nm, 10 microns-5 nm, 1 micron-5 nm, 100 nm-5 nm, 100 nm-10 nm, 50 nm-10 nm or any integer size range there between. In other instances the carrier domain is smaller than 5 nm in size. In such instance the nanoparticle will be cleared into the urine. However, the presence of free detectable marker can still be detected for instance using mass spectrometry. In some embodiments the carrier domain is 1-5 nm, 2-5 nm, 3-5 nm, or 4-5 nm.

Optionally the carrier domain may include a biological agent. In one embodiment a biological agent could be incorporated in the carrier domain or it may make up the carrier domain. For instance, it may form the scaffold or platform that the proteolytic domain is attached to. Thus the compositions of the invention can achieve two purposes at the same time, the diagnostic methods and delivery of a therapeutic agent. In some embodiments the biological agent may be an enzyme inhibitor. In that instance the biological agent can inhibit proteolytic activity at a local site and the detectable marker can be used to test the activity of that particular therapeutic at the site of action. HIV is an example of the disease in which active proteases can be monitored. In this embodiment the composition may include a microparticle or other delivery device carrying a protease inhibitor. The protease susceptible site may be sensitive to the HIV proteases such that feedback can be provided regarding the activity of the particular protease inhibitor.

Enzyme Susceptible Domains

The enzyme susceptible domain is a portion of a pro-diagnostic reagent that is typically connected to a carrier domain. An enzyme susceptible domain may be directly (e.g., via a peptide bond) or indirectly (e.g., by a linker) connected to a carrier domain. An enzyme susceptible domain, as used herein, is the portion of the modular structure (e.g., a pro-diagnostic reagent) that promotes the enzymatic reaction in a subject or tissue sample, causing the release of a detectable marker (e.g., a signature molecule).

The enzyme susceptible site is dependent on enzymes that are active in a specific disease state. For instance, tumors are associated with a specific set of enzymes. If the disease state being analyzed is a tumor then the product is designed with an enzyme susceptible site that matches that of the enzyme expressed by the tumor or other diseased tissue. Alternatively, the enzyme specific site may be associated with enzymes that are ordinarily present but are absent in a particular disease state. In this example, a disease state would be associated with a lack or signal associated with the enzyme, or reduced levels of signal compared to a normal reference. An enzyme, as used herein refers to any of numerous proteins produced in living cells that accelerate or catalyze the metabolic processes of an organism. Enzymes act on substrates. The substrate binds to the enzyme at a location called the active site just before the reaction catalyzed by the enzyme takes place. Enzymes include but are not limited to proteases, glycosidases, lipases, heparinases, phosphatases.

In some embodiments, an enzyme susceptible detectable domain comprises a substrate for a protease (e.g., an amino acid sequence that is cleaved by a protease). In some embodiments, the protease substrate is a substrate of a disease-associated enzyme. Examples of enzymes that are associated with disease in a subject include serine proteases, cysteine proteases, threonine proteases, aspartic proteases, glutamic proteases, metalloproteases, etc. Examples of substrates for disease-associated enzymes include but are not limited to SLKRYGGG (SEQ ID NO: 3; plasma kallikrein), AAFRSRGA (SEQ ID NO: 4; kallikrein 1), xxFRFFxx (SEQ ID NO: 5; cathepsin B), QSVGFA (SEQ ID NO: 6: cathepsin B), LGLEGAD (SEQ ID NO: 7; cathepsin K), GPLD (SEQ ID NO: 8; subunit beta 1c), LGVLIV (SEQ ID NO: 9: cathepsin D), GLVLVA (SEQ ID NO: 10; cathepsin E), PAALVG (SEQ ID NO: 11; MMP2), GPAGLAG (SEQ ID NO: 12; MMP9), GGPLGVRGKK (SEQ ID NO: 13; MMP9), and GGfPRSGGGK (f=d-stereoisomer of phenylalanine; SEQ ID NO: 14; thrombin).

The enzyme susceptible site may be optimized to provide both high catalytic activity (or other enzymatic activity) for specified target enzymes but to also release optimized detectable markers for detection. Patient outcome depends on the phenotype of individual diseases at the molecular level, and this is often reflected in expression of enzymes. The recent explosion of bioinformatics has facilitated exploration of complex patterns of gene expression in human tissues (Fodor, S. A. Massively parallel genomics. Science 277, 393-395 (1997)). Sophisticated computer algorithms have been recently developed capable of molecular diagnosis of tumors using the immense data sets generated by expression profiling (Khan J, Wei J S, Ringner M, Saal L H, Ladanyi M, Westermann F. et al. Classification and diagnostic prediction of cancers using gene expression profiling and artificial neural networks. Nat Med 2001; 7:673-679). This information can be accessed in order to identify enzymes and substrates associated with specific diseases. Based on this information the skilled artisan can identify appropriate enzyme or substrates to incorporate into the pro-diagnostic reagent.

Table 1 provides a non-limiting list of enzymes associated with (either increased or decreased with respect to normal) disease and in some instances, the specific substrate. Table 2 provides a non-limiting list of substrates associated with disease or other conditions. Numerous other enzyme/substrate combinations associated with specific diseases or conditions are known to the skilled artisan and are useful according to the invention.

TABLE 1

| Disease | Enzyme | Substrate |
| --- | --- | --- |
| Cancer | MMP | collagens, gelatin, various ECM proteins |

TABLE 1-continued

| Disease | Enzyme | Substrate |
|---|---|---|
| Cancer | MMP-2 | type IV collagen and gelatin |
| Cancer | MMP-9 | type IV and V collagens and gelatin |
| Cancer | kallikreins | kininogens, plasminogen |
| Cancer | cathepsins | broad spectrum of substrates |
| Cancer | plasminogen activator, tPA | Plasminogen |
| Cancer | ADAM (A Diseintegrin And Metalloprotease, also MDC, Adamalysin) | various extracellular domains of transmembrane proteins |
| Pancreatic carcinoma | MMP-7 | various, e.g. collagen 18, FasL, HLE, DCN, IGFBP-3, MAG, plasminogen, other MMPs |
| Pancreatic Cancer | ADAM9, ADAM15 | various extracellular domains of transmembrane proteins |
| Prostate adenocarcinoma | Matriptase, a type II transmembrane serine protease | unspecific, cleaves after Lys or Arg residues |
| Prostate cancer | Kallikrein 3 | kininogens, plasminogen |
| Prostate cancer | ADAM15 | various extracellular domains of transmembrane proteins |
| Ovarian carcinoma | Kallikrein 6 | kininogens, plasminogen |
| Epithelial-derived tumors (breast, prostate, ovarian, colon, oral) | Matriptase, a type II transmembrane serine protease | unspecific, cleaves after Lys or Arg residues |
| Ovarian Cancer | MMP-2, MMP-9, kallikrein-10 (hk-10) | type IV and V collagens and gelatin, kininogens, plasminogen |
| Breast, gastric, prostate cancer | cathepsins B, L and D | broad spectrum of substrates |
| Endometrial cancer | cathepsin B | unspecific cleavage of a broad spectrum of substrates without clear sequence specificity |
| esophageal adenocarcinoma | cathepsin B | unspecific cleavage of a broad spectrum of substrates without clear sequence specificity |
| Invasive cancers, metastases | type II integral serine proteases (dipeptidyl peptidase IV (DPP4/CD26), seprase/fibroblast activation protein alpha (FAPalpha) and related type II transmembrane prolyl serine peptidases)) | |
| Invasive cancers, metastases | Seprase | various ECM proteins |
| Viral Infections | | |
| All Retroviruses | viral protease | precursor GagPol fusion |
| HIV | HIV protease (HIV PR, an aspartic protease) | precursor Gag and GagPol proteins |
| Hepatitis C | NS3 serine protease | viral precursor polyprotein |
| Dengue | Dengue protease | autocleavage (NS2B/NS3), NS3/NS4A and NS4B/NS5 cleavage |
| West Nile | NS2B/NS3pro | viral precursor polyprotein |
| Bacterial Infections | | |
| *Legionella* spp. | zinc metalloprotease | Me-Arg-Pro-Tyr |
| Meninogencephalitis | histolytic cysteine protease | |
| *Streptococcus pyogenes* (Group A *Streptococcus*) | streptococcal pyrogenic exotoxin B (SpeB) | extracellular matrix, immunoglobulins, complement components |
| *Clostridium difficile* | Cwp84 | fibronectin, laminin, vitronectin and other ECM proteins |
| Additional Diseases | | |
| Alzheimer's disease | BACE-1,2 (Alzheimer secretase) | β-amyloid precursor protein |
| Stroke and recovery | MMP, tPA | |
| cardiovascular disease | Angiotensin Converting Enzyme (ACE) | angiotensin I, bradykinin |
| Atherosclerosis | cathepsin K, L, S | broad spectrum of substrates |
| arthritis | MMP-1 | triple-helical fibrillar collagens |
| rheumatoid arthritis | thrombin | Osteopontin |
| osteoarthritis | thrombin | Osteopontin |
| osteoporosis/osteoarthritis | cathepsin K, S | broad spectrum of substrates |
| Arthritis, inflammatory joint disease | Aggrecanase (ADAMTS4, ADAMTS11) | aggrecans (proteoglycans) |
| thrombosis | factor Xa (thrombokinase) | Prothrombin |
| thrombosis | ADAMTS13 | von Willebrand factor (vWF) |

TABLE 1-continued

| Disease | Enzyme | Substrate |
| --- | --- | --- |
| thrombosis | plasminogen activator, tPA | Plasminogen |
| Stress-induced Renal pressure natriuresis | Prostasin | epithelial Na channel subunits |

TABLE 2

| DISEASE | TARGET SUBSTRATE | ENZYME |
| --- | --- | --- |
| Inflammation | Interleukin 1 beta | MMP-2, MMP-3, MMP-9, Trypsin, chymotrypsin, pepsin, Lys-C, Glu-C, Asp-N, Arg-C |
| Pituitary gland dysfunction, abnormal bone density, growth disorders | IGFBP-3 | MMP-1, MMP-3, MMP-9, Trypsin, chymotrypsin, pepsin, Lys-C, Glu-C, Asp-N, Arg-C |
| Cancer | TGF-beta | MMP-9, Trypsin, chymotrypsin, pepsin, Lys-C, Glu-C, Asp-N, Arg-C |
| Cancer, autoimmune disease | TNF | MMP-7, Trypsin, chymotrypsin, pepsin, Lys-C, Glu-C, Asp-N, Arg-C |
| Cancer, autoimmune disease | FASL | MMP-7, Trypsin, chymotrypsin, pepsin, Lys-C, Glu-C, Asp-N, Arg-C |
| Wound healing, cardiac disease | HB-EGF | MMP-3, Trypsin, chymotrypsin, pepsin, Lys-C, Glu-C, Asp-N, Arg-C |
| Pfeiffer syndrome | FGFR1 | MMP-2, Trypsin, chymotrypsin, pepsin, Lys-C, Glu-C, Asp-N, Arg-C |
| Cancer | Decorin | MMP-2, MMP-3, MMP-7, Trypsin, chymotrypsin, pepsin, Lys-C, Glu-C, Asp-N, Arg-C |
| Cancer | Tumor associated carbohydrate antigens | Endoglycosidases |
| Cancer | Sialyl Lewis$^a$ | O-glycanase |
| Cancer | Sialyl Lewis$^x$ | O-glycanase |
| Cancer/Rheumatoid Arthritis, pulmonary hypertension | VEGF | Trypsin, chymotrypsin, pepsin, Lys-C, Glu-C, Asp-N, Arg-C |
| Cancer | EGF | Trypsin, chymotrypsin, pepsin, Lys-C, Glu-C, Asp-N, Arg-C |
| Cancer | IL2 | Trypsin, chymotrypsin, pepsin, Lys-C, Glu-C, Asp-N, Arg-C |
| Cancer inflammation/angiogenesis | IL6 | Trypsin, chymotrypsin, pepsin, Lys-C, Glu-C, Asp-N, Arg-C |
| Cancer | IFN-γ | Trypsin, chymotrypsin, pepsin, Lys-C, Glu-C, Asp-N, Arg-C |
| Cancer inflammation/angiogenesis, Rheumatoid Arthritis | TNF-α | Trypsin, chymotrypsin, pepsin, Lys-C, Glu-C, Asp-N, Arg-C |
| Cancer, Pulmonary fibrosis, Asthma | TGF-β | Trypsin, chymotrypsin, pepsin, Lys-C, Glu-C, Asp-N, Arg-C |
| Cancer, Pulmonary hypertension | PDGF | Trypsin, chymotrypsin, pepsin, Lys-C, Glu-C, Asp-N, Arg-C |
| Cancer, pulmonary cystadenoma | Fibroblast growth factor (FGF) | Trypsin, chymotrypsin, pepsin, Lys-C, Glu-C, Asp-N, Arg-C |
| Cancer | Brain-derived neurotrophic factor (BDNF) | Trypsin, chymotrypsin, pepsin, Lys-C, Glu-C, Asp-N, Arg-C |
| Cancer | Interferon regulatory factors (IRF-1, IRF-2) | Trypsin, chymotrypsin, pepsin, Lys-C, Glu-C, Asp-N, Arg-C |
| Inhibitor of tumor suppressors | MIF | Trypsin, chymotrypsin, pepsin, Lys-C, Glu-C, Asp-N, Arg-C |
| Lymphomas/carcinomas, alveolar proteinosis | GM-CSF | Trypsin, chymotrypsin, pepsin, Lys-C, Glu-C, Asp-N, Arg-C |
| Cancer invasion | M-CSF | Trypsin, chymotrypsin, pepsin, Lys-C, Glu-C, Asp-N, Arg-C |
| Chemical carcinogenesis, multiple sclerosis, rheumatoid arthritis, Crohn's disease | IL-12 | Trypsin, chymotrypsin, pepsin, Lys-C, Glu-C, Asp-N, Arg-C |
| Natural Killer T cell leukemias, inflammatory bowel disease, rheumatoid arthritis | IL-15 | Trypsin, chymotrypsin, pepsin, Lys-C, Glu-C, Asp-N, Arg-C |

TABLE 2-continued

| DISEASE | TARGET SUBSTRATE | ENZYME |
|---|---|---|
| Cirrhosis | Tissue inhibitor of MMPs (TIMPs) | Trypsin, chymotrypsin, pepsin, Lys-C, Glu-C, Asp-N, Arg-C |
| Cirrhosis | Collagen I, III | MMP-1, MMP-8, Trypsin, chymotrypsin, pepsin, Lys-C, Glu-C, Asp-N, Arg-C |
| Cirrhosis | Collagen IV, V | MMP-2, Trypsin, chymotrypsin, pepsin, Lys-C, Glu-C, Asp-N, Arg-C |

In some embodiments, the enzyme susceptible domain is a cancer-specific (e.g., tumor-specific) enzyme susceptible domain. As used herein, "cancer-specific enzyme susceptible domain" refers to an enzyme susceptible domain that is capable of being cleaved by a protease that is present (or upregulated) in a subject having a cancer (e.g., a malignant tumor, metastatic cancer, etc.). For example, certain cancers (e.g. metastatic cancers) are associated with upregulation of specific enzymes (e.g. ADAM28, MMP9, MMP12, ACE, C2, ADAMTS5, HTRA4, MMP16, MMP1, MMP3, MMP4, MMP7, MMP8, Cathepsin B, Cathepsin L, Cathepsin S, ADAM10, ADAM12. PRSS3, uPA, etc.).

The enzyme susceptible detectable marker is preferably a polymer made up of a plurality of chemical units. A "chemical unit" as used herein is a building block or monomer which may be linked directly or indirectly to other building blocks or monomers to form a polymer.

Linker Molecules

An enzyme susceptible detectable marker may be attached directly to the carrier. For instance it may be coated directly on the surface of microparticles using known techniques. Alternatively if the carrier is a protein material it may be directly connected through a peptide bond. Additionally, the enzyme susceptible detectable marker may be connected to the carrier domain through the use of a linker. As used herein "linked" or "linkage" means two entities are bound to one another by any physicochemical means. Any linkage known to those of ordinary skill in the art, covalent or non-covalent, is embraced. Tus, in some embodiments the carrier has a linker attached to an external surface, which can be used to link the enzyme susceptible detectable marker. Another molecule can also be attached to the linker. In some embodiments, two molecules are linked using a transpeptidase, for example Sortase A.

Aspects of the disclosure relate to the surprising discovery that the sensitivity and specificity of a pro-diagnostic reagent may be significantly improved by modulating presentation of the enzyme susceptible domain to its cognate enzyme, for example by varying the distance between the carrier domain and the enzyme susceptible domain of the pro-diagnostic reagent. For example, in some embodiments, a polymer comprising one or more linking molecules is used to adjust the distance between a carrier domain and an enzyme susceptible domain, thereby improving presentation of the enzyme susceptible domain to an enzyme.

In some embodiments, the distance between a carrier domain and an enzyme susceptible domain ranges from about 1.5 angstroms to about 1000 angstroms. In some embodiments, the distance between a carrier domain and an enzyme susceptible domain ranges from about 10 angstroms to about 500 angstroms (e.g., any integer between 10 and 500). In some embodiments, the distance between a carrier domain and an enzyme susceptible domain ranges from about 50 angstroms to about 800 angstroms (e.g., any integer between 50 and 800). In some embodiments, the distance between a carrier domain and an enzyme susceptible domain ranges from about 600 angstroms to about 1000 angstroms (e.g., any integer between 600 and 1000). In some embodiments, the distance between a carrier domain and an enzyme susceptible domain is greater than 1000 angstroms.

Examples of linking molecules include but are not limited to poly(ethylene glycol), peptide linkers. N-(2-Hydroxypropyl) methacrylamide linkers, elastin-like polymer linkers, and other polymeric linkages. Generally, a linking molecule is a polymer and may comprise between about 2 and 200 (e.g., any integer between 2 and 200, inclusive) molecules. In some embodiments, a linking molecule comprises one or more poly(ethylene glycol) (PEG) molecules. In some embodiments, a linking molecule comprises between 2 and 200 (e.g., any integer between 2 and 200, inclusive) PEG molecules. In some embodiments, a linking molecule comprises between 2 and 20 PEG molecules. In some embodiments, a linking molecule comprises between 5 and 15 PEG molecules. In some embodiments, a linking molecule comprises between 5 and 25 PEG molecules. In some embodiments, a linking molecule comprises between 10 and 40 PEG molecules. In some embodiments, a linking molecule comprises between 25 and 50 PEG molecules. In some embodiments, a linking molecule comprises between 100 and 200 PEG molecules.

Signature Molecules

The signature molecule is capable of being released from the pro-diagnostic reagent when exposed to an enzyme in vivo or in vitro. In some embodiments, the detectable marker (e.g., signature molecule) once released is free to travel to a remote site for detection. A remote site is used herein to refer to a site in the body that is distinct from the bodily tissue housing the enzyme where the enzymatic reaction occurs. In some embodiments, the bodily tissue housing the enzyme where the enzymatic reaction occurs is a tumor. In some embodiments, a remote site is a biological sample that is non-invasively obtained from a subject, for example a urine sample, or a blood sample.

Modification of the enzyme susceptible domain by an enzyme in vivo, results in the production of a signature molecule (e.g., a detectable marker). Alternatively, when the enzyme susceptible detectable marker is an enzyme the enzyme cleaves an endogenous substrate producing a detectable marker from the endogenous substrate. In some embodiments, the detectable marker is composed of two ligands joined by a linker, as described above. The detectable marker may be comprised of, for instance one or more of a peptide, nucleic acid, small molecule, fluorophore/quencher, carbohydrate, particle, radiolabel. MRI-active compound, inorganic material, organic material, with encoded characteristics to facilitate optimal detection.

Aspects of the disclosure relate to the surprising discovery that pro-diagnostic reagents comprising a ligand that binds to a target tissue and certain signature molecules are useful for in situ localization of enzymatic activity in a tissue (e.g., a tissue sample). Without wishing to be bound by any particular theory, pro-diagnostic reagents described by the disclosure bind to a target tissue prior to proteolysis, as opposed to enabling tissue binding after proteolysis, thereby allowing detection of the signature molecule in situ and thus localization of enzymatic activity within a tissue (e.g., a tumor within a tissue sample). Accordingly, in some embodiments, a signature molecule does not travel to a site that is remote from the bodily tissue housing the enzyme where the enzymatic reaction occurs. In some embodiments, a signature molecule remains bound to a carrier domain (e.g. directly or indirectly) after cleavage of an enzyme susceptible domain. For example, in some embodiments, a signature molecule comprises a FRET pair (e.g., a fluorophore and a quencher) linked by an enzyme susceptible domain, configured such that cleavage of the enzyme susceptible domain results in release of the quencher molecule from the carrier domain and detection of the carrier domain-linked fluorophore.

The detectable markers of the present disclosure comprise a detection ligand. A detection ligand is a molecule that is capable of being detected by any of a variety of methods. In some embodiments, the detectable marker comprises a detection ligand and a capture ligand, wherein the detection ligand and the capture ligand are distinct. While a capture ligand and a detection ligand will be distinct from one another in a particular detectable marker, the class of molecules that make up capture and detection ligands overlap significantly. For instance, many molecules are capable of being captured and detected. In some instances these molecules may be detected by being captured or capturing a probe. The capture and detection ligand each independently may be one or more of the following: a protein, a peptide, a polysaccharide, a nucleic acid, a fluorescent molecule, or a small molecule, for example. In some embodiments the detection ligand or the capture ligand may be, but is not limited to, one of the following: Alexa488, TAMRA, DNP, fluorescein, Oregon Green, Texas Red, Dansyl, BODIPY, Alexa405, Cascade Blue, Lucifer Yellow, Nitrotyrosine, HA-tag, FLAG-tag, His-tag, Myc-tag, V5-tag, S-tag, biotin or streptavidin. In some embodiments, the capture ligand and a detection ligand are connected by a linker, for example as described in International Application Publication No. WO2014/197840, filed Jun. 6, 2014, the entire contents of which are incorporated herein by reference. The purpose of the linker is prevent steric hindrance between the two ligands. Thus, the linker may be any type of molecule that achieves this. The linker may be, for instance, a polymer such as PEG, a protein, a peptide, a polysaccharide, a nucleic acid, or a small molecule. In some embodiments the linker is a protein of 10-100 amino acids in length. In other embodiments the linker is GluFib. Optionally, the linker may be 8 nm-100 nm, 6 nm-100 nm, 8 nm-80 nm, 10 nm-100 nm, 13 nm-100 nm, 15 nm-50 nm, or 10 nm-50 nm in length.

In some embodiments, a signature molecule is a mass encoded reporter, for example an iCORE as described in WO2012/125808, filed Mar. 15, 2012, the entire contents of which are incorporated herein by reference. Upon arrival in the diseased microenvironment, the iCORE agents interface with aberrantly active proteases to direct the cleavage and release of surface-conjugated, mass-encoded peptide substrates into host urine for detection by mass spectrometry (MS) as synthetic biomarkers of disease.

The signature molecule may be detected by any known detection methods to achieve the capture/detection step. A variety of methods may be used, depending on the nature of the detectable marker. Detectable markers may be directly detected, following capture, through optical density, radioactive emissions, nonradiative energy transfers, or detectable markers may be indirectly detected with antibody conjugates, affinity columns, streptavidin-biotin conjugates, PCR analysis, DNA microarray, and fluorescence analysis.

The capture assay in some embodiments involves a detection step selected from the group consisting of an ELISA, including fluorescent, colorimetric, bioluminescent and chemiluminescent ELISAs, a paper test strip or Lateral flow assay (LFA), bead-based fluorescent assay, and label-free detection, such as surface plasmon resonance (SPR). The capture assay may involve, for instance, binding of the capture ligand to an affinity agent.

The analysis step may be performed directly on the biological sample or the signature component may be purified to some degree first. For instance, a purification step may involve isolating the detectable marker from other components in the biological sample. Purification steps include methods such as affinity chromatography. As used herein an "isolated molecule" or "purified molecule" is a detectable marker that is isolated to some extent from its natural environment. The isolated or purified molecule need not be 100% pure or even substantially pure prior to analysis.

The methods for analysing detectable markers by identifying the presence of a detectable marker may be used to provide a qualitative assessment of the molecule (e.g. whether the detectable marker is present or absent) or a quantitative assessment (e.g., the amount of detectable marker present to indicate a comparative activity level of the enzymes. The quantitative value may be calculated by any means, such as, by determining the percent relative amount of each fraction present in the sample. Methods for making these types of calculations are known in the art.

The detectable marker may be labeled. For example, a label may be added directly to a nucleic acid when the isolated detectable marker is subjected to PCR. For instance, a PCR reaction performed using labeled primers or labeled nucleotides will produce a labeled product. Labeled nucleotides (e.g., fluorescein-labeled CTP) are commercially available. Methods for attaching labels to nucleic acids are well known to those of ordinary skill in the art and, in addition to the PCR method, include, for example, nick translation and end-labeling.

Labels suitable for use in the methods of the present invention include any type of label detectable by standard means, including spectroscopic, photochemical, biochemical, electrical, optical, or chemical methods. Preferred types of labels include fluorescent labels such as fluorescein. A fluorescent label is a compound comprising at least one fluorophore. Commercially available fluorescent labels include, for example, fluorescein phosphoramidides such as fluoreprime (Pharmacia, Piscataway, N.J.), fluoredite (Millipore, Bedford, Mass.), FAM (ABI, Foster City, Calif.), rhodamine, polymethadine dye derivative, phosphores, Texas red, green fluorescent protein, CY3, and CY5. Polynucleotides can be labeled with one or more spectrally distinct fluorescent labels. "Spectrally distinct" fluorescent labels are labels which can be distinguished from one another based on one or more of their characteristic absorption spectra, emission spectra, fluorescent lifetimes, or the like. Spectrally distinct fluorescent labels have the advantage that they may be used in combination ("multiplexed").

Radionuclides such as 3H, 125I, 35S, 14C, or 32P are also useful labels according to the methods of the invention. A plurality of radioactively distinguishable radionuclides can be used. Such radionuclides can be distinguished, for example, based on the type of radiation (e.g. α, β, or δ radiation) emitted by the radionuclides. The 32P signal can be detected using a phosphoimager, which currently has a resolution of approximately 50 microns. Other known techniques, such as chemiluminescence or colorimetric (enzymatic color reaction), can also be used.

Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET), such as fluorescence resonance energy transfer (FRET). Cleavage of the peptide results in separation of the chromophore and fluorophore, removal of the quench, and generation of a subsequent signal measured from the donor fluorophore. Examples of FRET pairs include 5-Carboxyfluorescein (5-FAM) and CPQ2, FAM and DABCYL, Cy5 and QSY21, Cy3 and QSY7, etc.

The disease or condition assessed according to the methods of the invention is any disease or condition that is associated with an enzyme. For instance, cancer, cardiovascular disease, arthritis, viral, bacterial, parasitic or fungal infection. Alzheimer's disease emphysema, thrombosis, hemophilia, stroke, organ dysfunction, any inflammatory condition, vascular disease, parenchymal disease, or a pharmacologically-induced state are all known to be associated with enzymes. A pharmacologically-induced state is a condition in which enzyme inhibitors and other agents directly or indirectly affect enzyme activities. Thus each of the these can be assessed or monitored or studied according to methods of the disclosure.

Tumor-Penetrating Ligands

Aspects of the disclosure relate to the discovery that pro-diagnostic reagents comprising certain ligands that bind to a target tissue (e.g., tumor-penetrating ligands) significantly improve the specificity and sensitivity of the reagents.

As used herein, a "ligand capable of binding to a tissue", or "capable of binding to a tissue sample" refers to a molecule that specifically binds to a target tissue. The ligand may be a peptide, protein (e.g., antibody), small molecule, nucleic acid (e.g., DNA, RNA, etc.), aptamer, etc. For example, in some embodiments a ligand is a peptide or protein that binds to a receptor on the surface of a particular cell type (e.g., a tumor cell). Examples of tissue targeting ligands include but are not limited to Lyp1, iRGD, anticancer antibodies (e.g., Trastuzumab, Pertuzumab, Brentuximab, Tositumomab, Ibritumomab, etc.) and fragments thereof, etc.

A "tumor-penetrating peptide" is a peptide that binds to a receptor expressed by a cancer cell and mediates internalization of a cargo molecule (e.g., a pro-diagnostic reagent) into the tumor tissue. In some embodiments, a tumor-penetrating peptide binds to a receptor involved in the active transport pathway of the cell (e.g., cancer cell), for example neuropilin 1 (NRP-1) or p32. Additional examples of receptors involved in the active transport pathway of cells (e.g., cancer cells) include but are not limited to neuropilin-2 (NRP-2), transferrin receptor, LDLR, etc.

Examples of tumor-penetrating peptides include but are not limited to LyP1 (CGNKRTRGC; SEQ ID NO: 1), iRGD (CRGDKGPDC; SEQ ID NO:2). TT1, iNGR, and others for example as disclosed in Ruoslahti et al. J. Cell Biol. 188: 759-768 (2010). In some embodiments, a suite of tumor-penetrating ligands specific for a range of primary receptors is produced by incorporation of the C-end rule motif, K/RXXK/R, which triggers the active internalization pathway of tumor cells.

Methods to Spatially Profile Protease Activity in Tissue

Aspects of the disclosure relate to the surprising discovery that pro-diagnostic reagents comprising a ligand that binds to a target tissue, and certain signature molecules, are useful for in situ localization of enzymatic activity in a tissue (e.g., a tissue sample).

As used herein, a biological sample is a tissue sample (such as a blood sample, a hard tissue sample, a soft tissue sample, etc.), a urine sample, saliva sample, fecal sample, seminal fluid sample, cerebrospinal fluid sample, etc. In preferred embodiments, the biological sample is a tissue sample. The tissue sample may be obtained from any tissue of the subject, including brain, lymph node, breast, liver, pancreas, colon, liver, lung, blood, skin, ovary, prostate, kidney, or bladder. The tissue from which the biological sample is obtained may be healthy or diseased. In some embodiments, a tissue sample comprises tumor cells or a tumor.

A tissue sample for use in methods described by the disclosure may be unmodified (e.g., not treated with any fixative, preservative, cross-linking agent, etc.) or physically or chemically modified. Examples of fixatives include aldehydes (e.g., formaldehyde, formalin, gluteraldehyde, etc.), alcohols (e.g., ethanol, methanol, acetone, etc.), and oxidizing agents (e.g., osmium tetroxide, potassium dichromate, chromic acid, potassium permanganate, etc.). In some embodiments, a tissue sample is cryopreserved (e.g., frozen). In some embodiments, a tissue sample is embedded in paraffin.

Without wishing to be bound by any particular theory, pro-diagnostic reagents as described herein are capable of binding to a target tissue prior to enzymatic cleavage of the enzyme susceptible domain, thereby preventing the diffusion of substrate and/or detectable signature molecule away from the site of enzymatic activity in a biological sample, such as a tissue sample. Accordingly, in some embodiments, after binding of the pro-diagnostic reagent to a tissue sample and subsequent cleavage of the enzyme susceptible domain, the pro-diagnostic reagent and signature molecule remain bound to the tissue sample.

Binding of the pro-diagnostic reagent to a tissue sample may be mediated by a molecule that specifically recognizes (e.g., specifically binds to) a site, such as a receptor, on a tissue sample. In some embodiments, the pro-diagnostic reagent comprises a tumor-penetrating peptide that binds to a tissue sample. In some embodiments, the pro-diagnostic reagent comprises another ligand that binds specifically to a target tissue, for example, charged peptides that specifically interact with the tissue (such as poly-arginine), peptides that specifically interact with target tissue cell membranes, and ligands that react chemically with the tissue to form covalent linkages (e.g., through reactive thiols or amines to link the pro-diagnostic reagent to the tissue).

The modality used for detection of the signature molecule (e.g., a signature molecule bound to a tissue sample and a carrier domain) will depend upon the characteristics of the signature molecule itself. For example, in some embodiments, the signature molecule is a peptide antigen and the detection method is a capture-based assay, such as ELISA. In some embodiments, the signature molecule is a fluorophore (e.g., a FRET pair comprising a fluorophore) and the detection method is a fluorescence-based imaging assay. Additional appropriate signature molecules and methods of detecting the same are described elsewhere in the disclosure and will be readily apparent to the skilled artisan.

Methods for Detecting Tumors in a Subject

In some aspects, the disclosure provides methods for detecting tumors in a subject. As used herein, a subject is a human, non-human primate, cow, horse, pig, sheep, goat, dog, cat, or rodent. In all embodiments human subjects are preferred. In aspects of the invention pertaining to cancer diagnosis in general the subject preferably is a human suspected of having cancer, or a human having been previously diagnosed as having cancer. Methods for identifying subjects suspected of having cancer may include physical examination, subject's family medical history, subject's medical history, biopsy, or a number of imaging technologies such as ultrasonography, computed tomography, magnetic resonance imaging, magnetic resonance spectroscopy, or positron emission tomography.

The disclosure is based, in part, on the discovery that pro-diagnostic reagents described herein are capable of detecting tumors smaller than 5 mm in diameter in a subject, which is surprising because generally the ability to identify cancer lesions with endogenous biomarkers was previously thought to be limited to detection of tumors greater than 1 cm in diameter. In some embodiments, methods described by the disclosure result in identification (e.g., detection) of a tumor smaller than 1 cm in a subject. In some embodiments, a tumor that is less than 1 cm, less than 0.5 cm, or less than 0.005 cm is detected using methods described by the disclosure. In some embodiments, the tumor that is detected is between 1 mm and 5 mm in diameter (e.g., about 1 mm, 2 mm, 3 mm, 4 mm, or about 5 mm) in diameter.

In some embodiments, the presence of a tumor in a subject is identified by obtaining a biological sample from a subject that has been administered a pro-diagnostic reagent as described by the disclosure and detecting the presence of a signature molecule in the biological sample. Generally, the biological sample may be a tissue sample (such as a blood sample, a hard tissue sample, a soft tissue sample, etc.), a urine sample, saliva sample, fecal sample, seminal fluid sample, cerebrospinal fluid sample, etc.

In some aspects, the disclosure relates to the discovery that pro-diagnostic reagents comprising certain modifications (e.g., surface presentation of enzyme susceptible domains, functionalization with a tumor-penetrating ligand, or a combination thereof) increase the sensitivity and selectivity of the pro-diagnostic reagent with regard to detection of the signature molecule at a site remote from the bodily tissue housing the enzyme where the enzymatic reaction occurs. Thus, in preferred embodiments, the biological sample is a sample that has been obtained non-invasively, for example a urine sample. In some embodiments, the biological sample is a blood sample.

The pro-diagnostic reagent, in some embodiments, comprises a modification that localizes the reagent to a target tissue (e.g., tissue of a tumor microenvironment). In some embodiments, the pro-diagnostic reagent comprises a tumor-penetrating peptide, for example a peptide that binds to a receptor involved in the active transport pathway of a cancer cell (e.g., p32 or NRP-1). Without wishing to be bound by any particular theory, a pro-diagnostic reagent comprising a tumor-penetrating peptide increases on-target (e.g., cell-type specific) and decreases off-target protease cleavage that occurs in vivo relative to a pro-diagnostic reagent that does not comprise a tumor-penetrating peptide.

Aspects of the disclosure are based on the observation that detection of a signature molecule in a urine signal increases when a primary receptor (e.g., a receptor expressed on the surface of a cancer cell) is matched with a tumor-penetrating ligand. For example, as described in the Examples section, administering a pro-diagnostic reagent comprising iRGD to a subject (e.g. a cell of a subject) having a tumor associated with expression of NRP-1 (the cognate receptor of iRGD) results in increased detection of signature molecules relative to administration of a pro-diagnostic reagent comprising iRGD to a subject (e.g. a cell of a subject) having a tumor that is not associated with expression of NRP-1. Accordingly, a cocktail of different tumor-penetrating peptides may be used, in some embodiments, to noninvasively and rapidly stratify patients on the basis of receptor expression. In some embodiments, methods described herein are useful as a companion diagnostic to monitor receptor status in tumors treated with precision medicines, such as integrin-targeted therapeutics.

Administration

Compositions described herein can be administered to any suitable subject. In some embodiments, pro-diagnostic reagents of the disclosure are administered to the subject in an effective amount for detecting enzyme activity. An "effective amount", for instance, is an amount necessary or sufficient to cause release of a detectable level of detectable marker in the presence of an enzyme. The effective amount of a compound of the invention described herein may vary depending upon the specific compound used, the mode of delivery of the compound, and whether it is used alone or in combination. The effective amount for any particular application can also vary depending on such factors as the disease being assessed or treated, the particular compound being administered, the size of the subject, or the severity of the disease or condition as well as the detection method. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective regimen can be planned.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The agent may comprise different types of carriers depending on whether it is to be administered in solid, liquid or aerosol form, and whether it need to be sterile for such routes of administration as injection.

Aspects of the disclosure relate to systemic administration of a pro-diagnostic reagent to a subject. In some embodiments, the systemic administration is injection, optionally subcutaneous injection. Preferably the material is injected into the body but could also be administered by other routes. For instance, the compounds of the present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

EXAMPLES

MMP9 is Upregulated Across Human Cancers

Figure 1B:
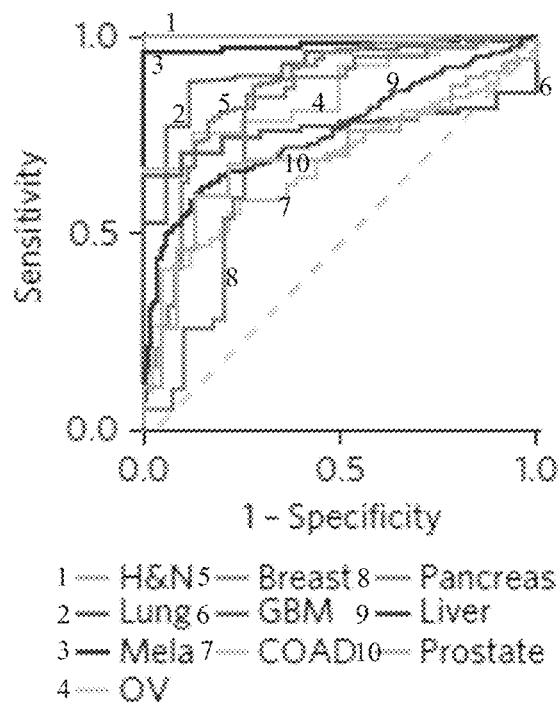
Figure 1C:
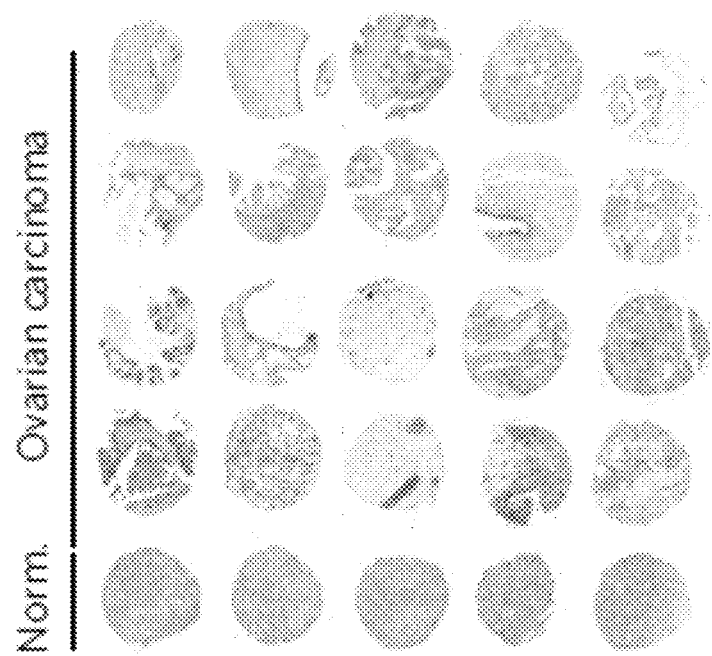
Figure 1D:
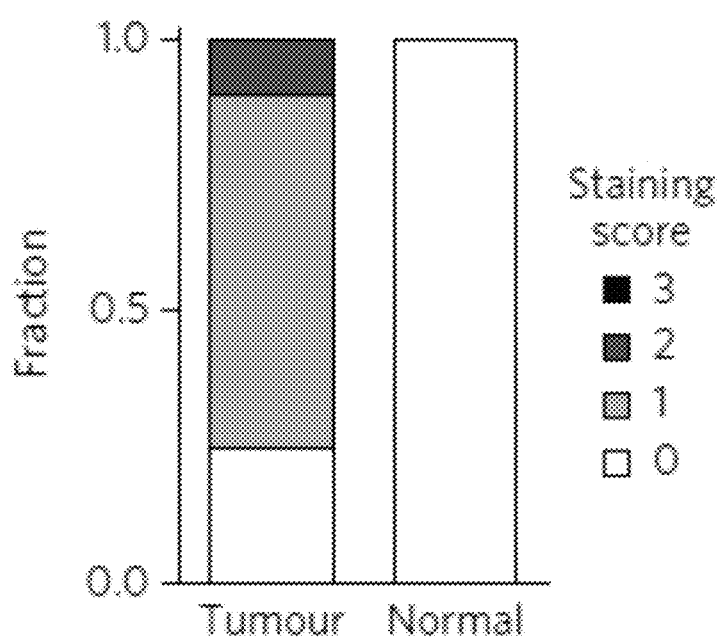
Figure 1E:
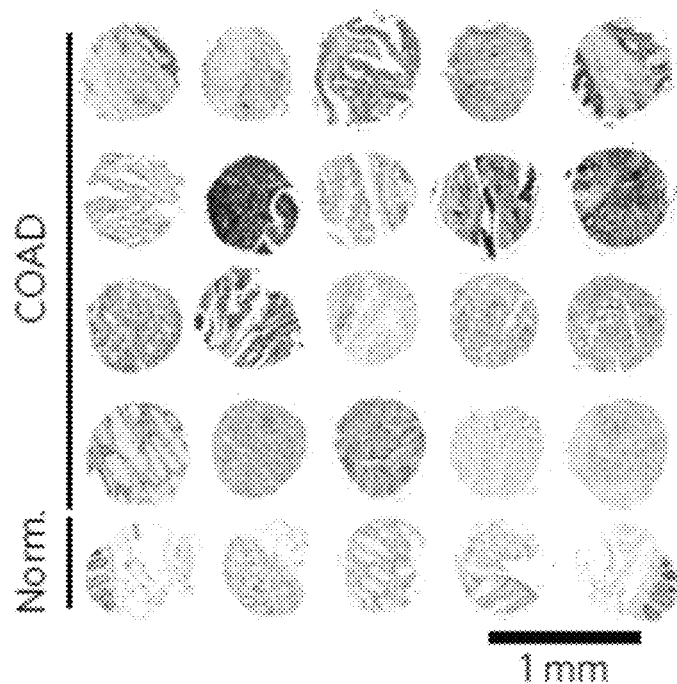
Figure 1F:
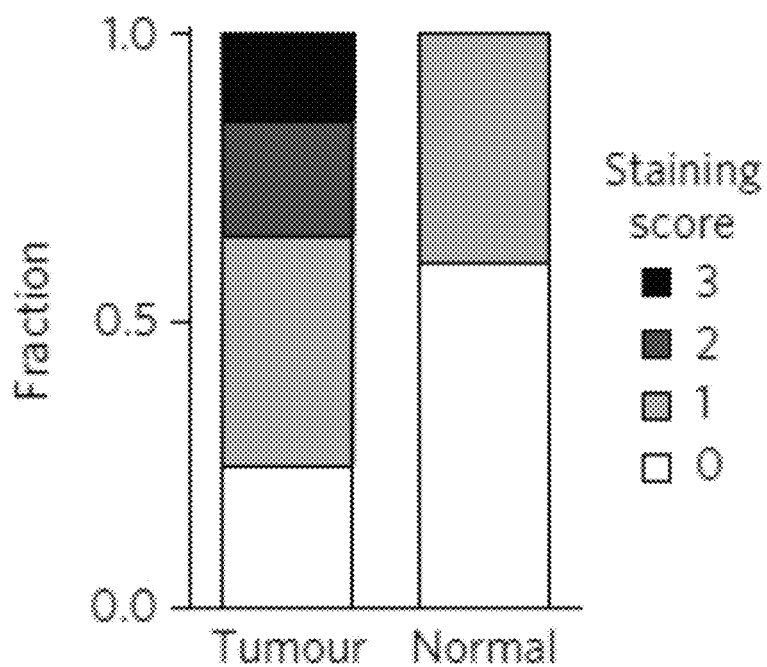
Figure 2A:
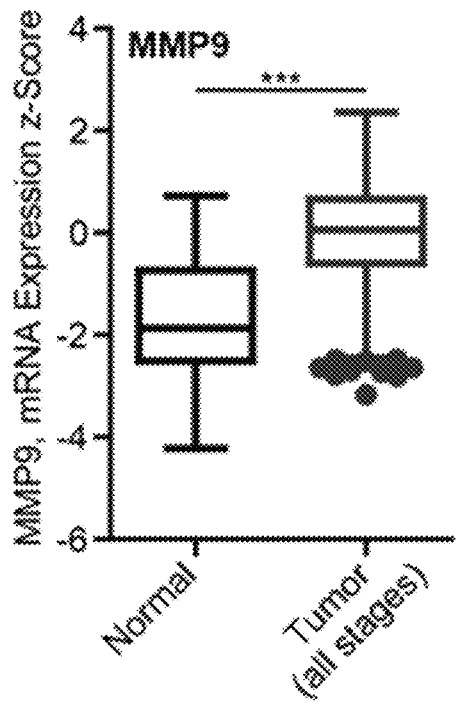
FIGS. 2A-2E show TCGA mRNA and human tissue microarray analysis of MMP9 expression.
Figure 2B:
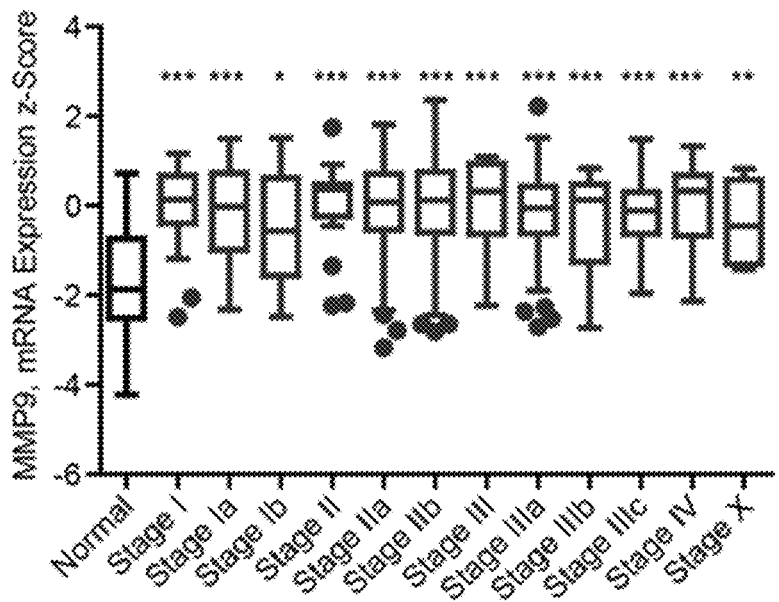
Figure 2C:
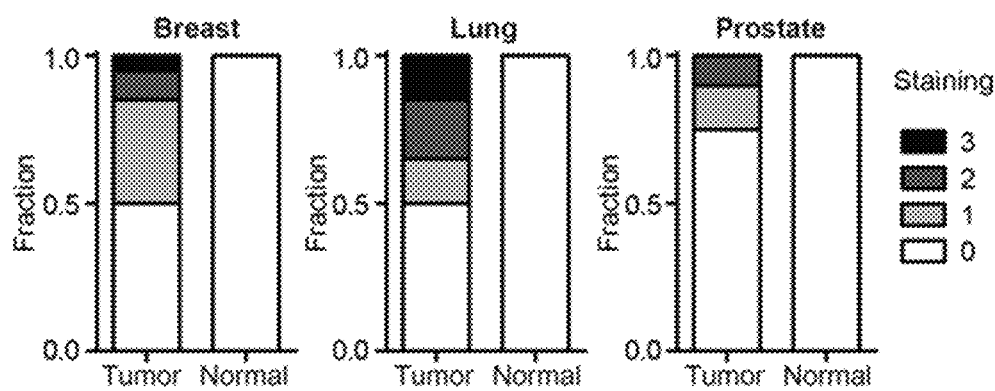

One embodiment of an Activity-based Nanosensor (ABN) was designed on the basis of a proteolytic target that is highly elevated across numerous human cancers and that has a fundamental biological role in tumor progression. Analysis of mRNA expression data from Oncomine and The Cancer Genome Atlas (TCGA) showed that matrix metalloproteinase 9 (MMP9) is significantly upregulated compared with healthy controls across many human cancer types (FIG. 1A), and this can be used to distinguish cancer from normal tissue, via construction of receiver operating characteristic (ROC) curves (median area under the curve (AUC)=0.81; FIG. 1B). Furthermore, MMP9 mRNA levels are consistent across all stages, indicating that it can be used for both early and late stage diagnosis (FIGS. 2A-2B). Using MMP9 as a disease marker may be a valuable means to distinguish aggressive cancers from indolent ones, as it is been observed to play a critical role in the angiogenic switch needed for access to host vasculature when tumors reach 1-2 mm in diameter. Therefore, in some embodiments, MMP9 activity measurements prospectively reflect disease progression, and do not merely detect a byproduct of tumor growth, as is the case with many existing blood biomarkers.

Figure 2D:
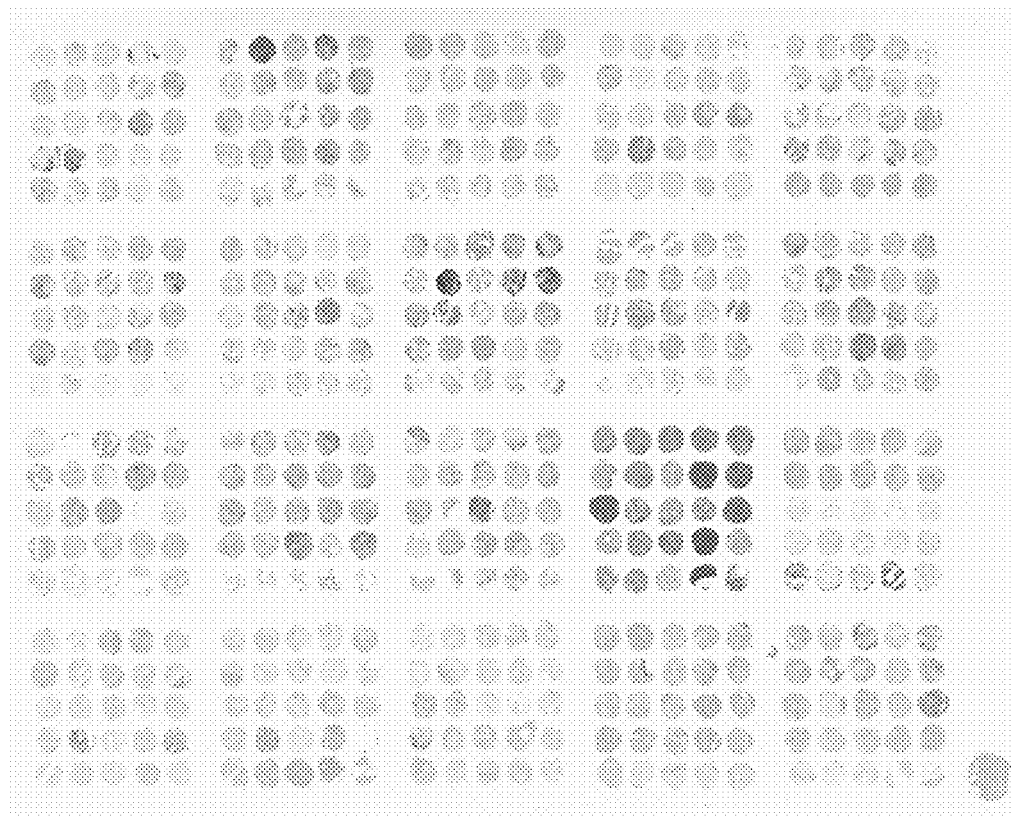
Figure 2E:
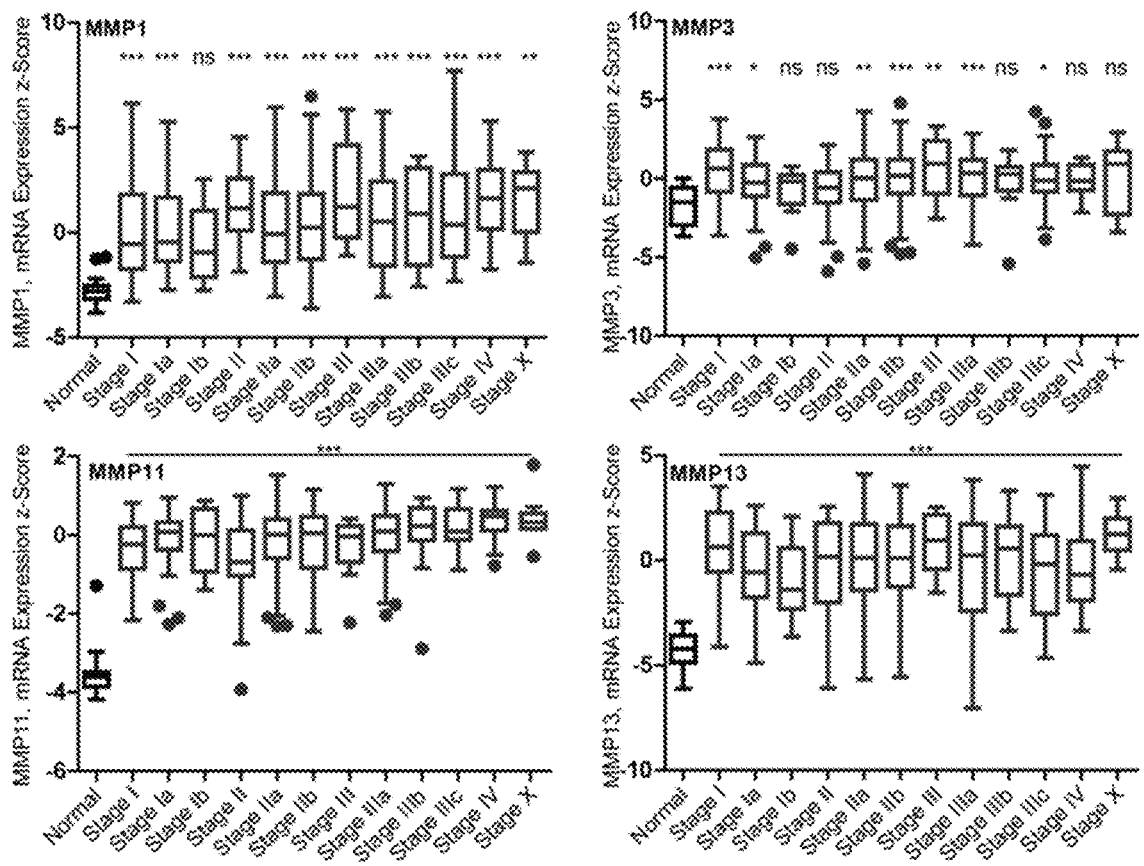

MMP9 immunohistochemical staining (blindly scored by a pathologist) was performed on a tumor tissue microarray (TMA). Data indicate that MMP9 protein levels were elevated across many human cancers (FIGS. 1C-1F and FIGS. 2B-2C). An ABN was produced as a probe for MMP9 activity in vivo and as a platform for further development, establishing design principles that could be applied to other tumor-specific proteases found to be upregulated in cancer. Existing point-of-care technologies inadequately assess MMP9, as it acts locally at the tumor site and thus, typically cannot be assayed from body fluids with high sensitivity and specificity. Further exploration into other MMPs in breast cancer samples from TCGA revealed several other biomarker candidates that had elevated mRNA levels (FIG. 2D). These proteases could be assayed with multiplexed substrates in other embodiments of ABNs.

ABN Optimization Achieves Magnitude-Fold Improvement

This example describes two strategies to engineer ABNs that were developed: (1) presentation of peptide substrates on the nanoparticle surface for maximal on-target and minimal off-target protease cleavage, and (2) modification of ABNs with tumor-penetrating ligands that engage active tumor trafficking pathways initiated by receptor binding. The strategies were also combined in order to increase cancer-specific signal generation.

Figure 3A:
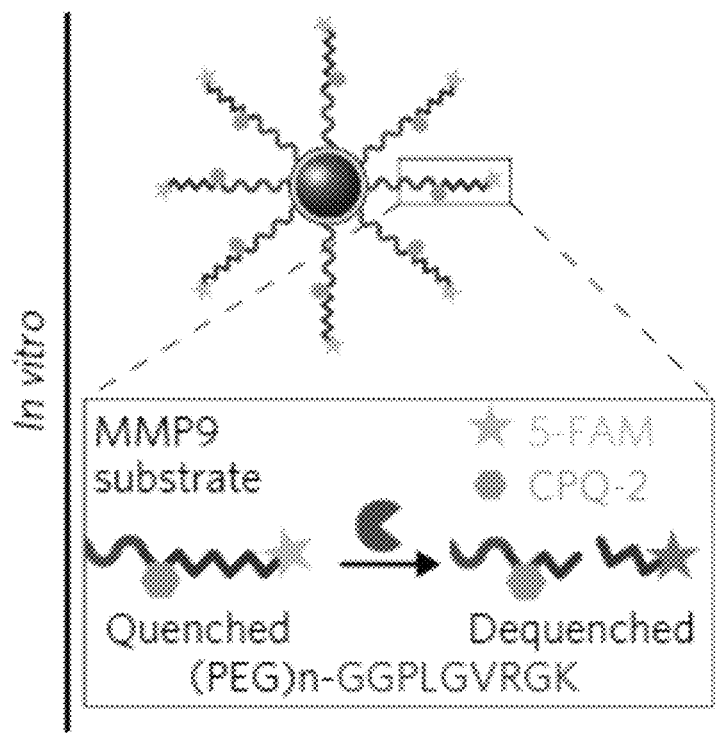
FIGS. 3A-3K show in vitro and in vivo experiments and in silico evaluation for engineering of a tuned ABN.
Figure 3B:
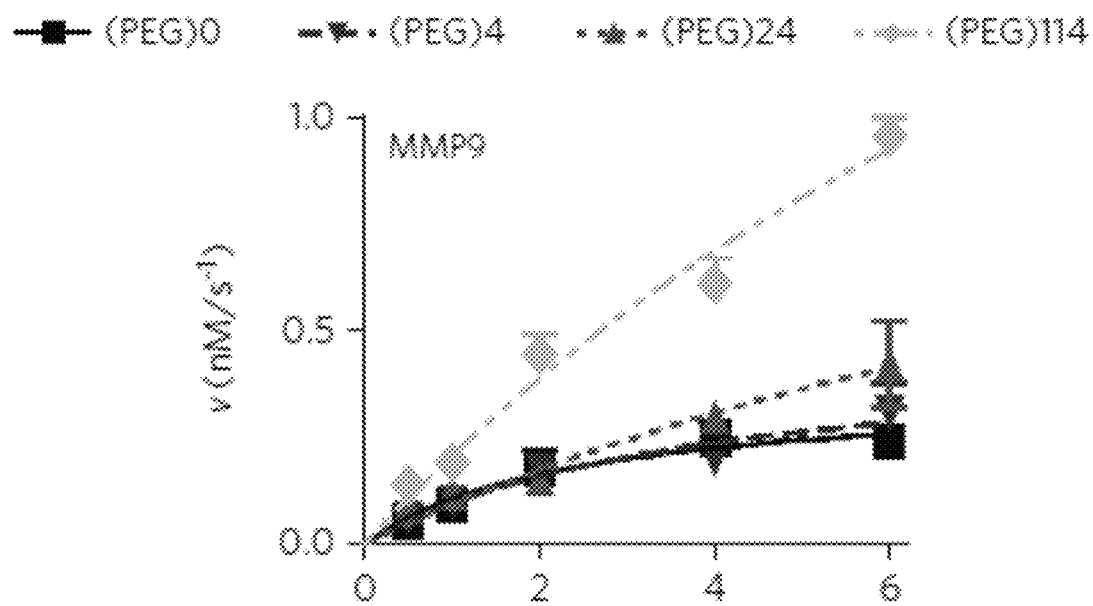
Figure 3C:
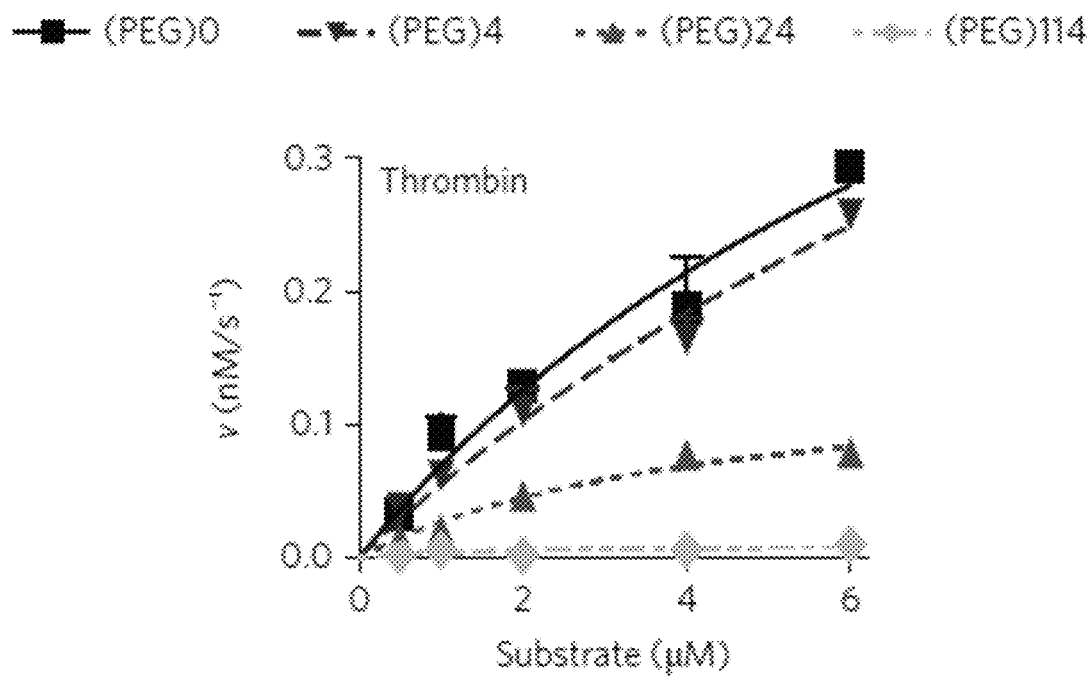
Figure 3D:
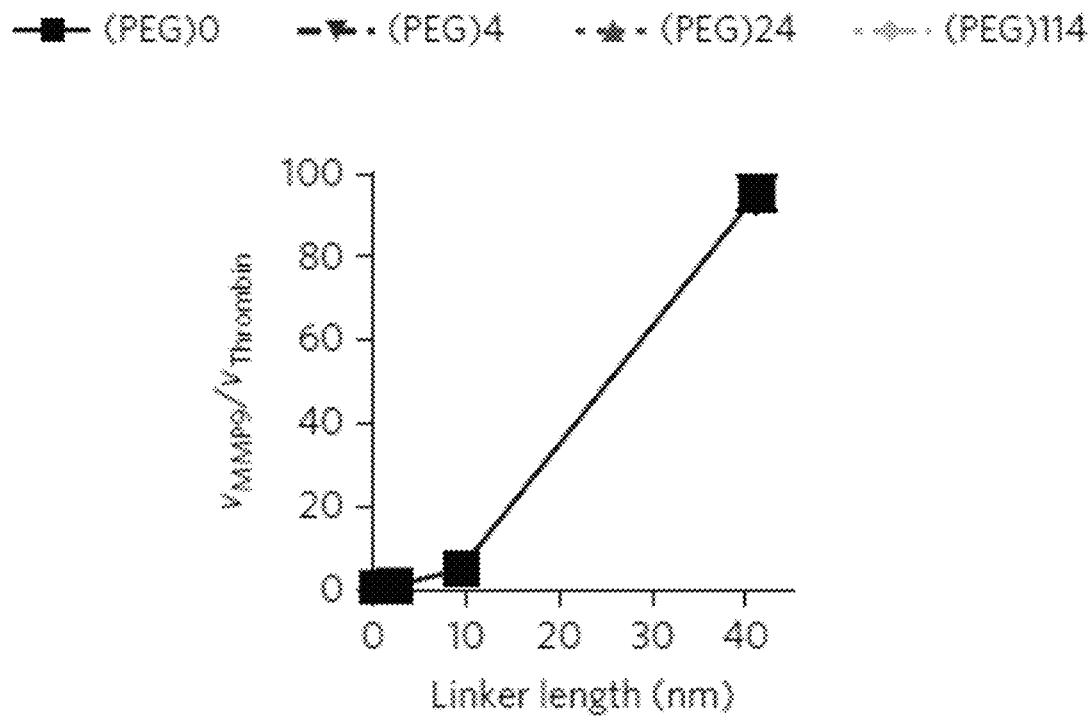
Figure 4:
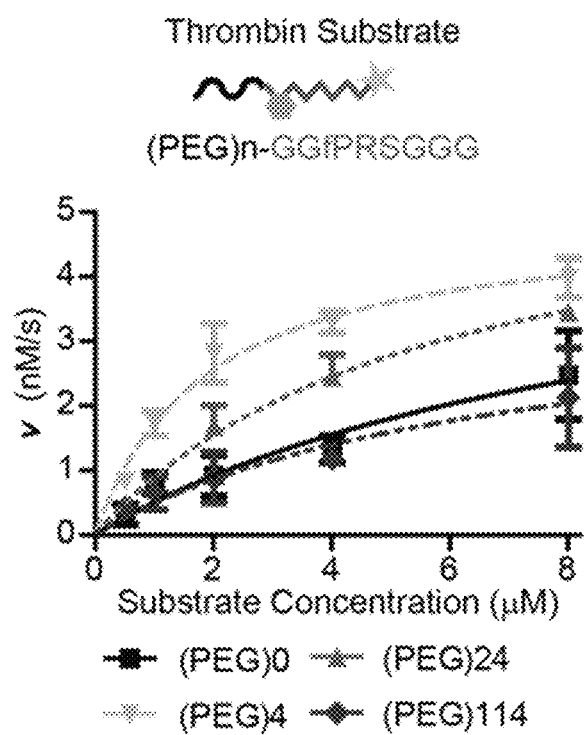
FIG. 4 shows thrombin cleavage of thrombin substrate varies on surface presentation. A thrombin substrate was presented on the nanoparticle surface with varying linker lengths (n=2-3, ±SEM). Unlike the MMP substrate, an intermediate length was optimal for thrombin catalysis. Data was fit to the Michaelis-Menten equation. The sequence corresponds to SEQ ID NO: 23).

In some embodiments, surface presentation of peptide substrates allows tuning of specificity between on- and off-target proteolytic cleavage rates of the substrate (e.g., MMP9 substrate). The cleavage kinetics of an MMP9 peptide substrate (PLGVRGK; SEQ ID NO: 15), flanked by a fluorescence resonance energy transfer (FRET) pair, at varying distances from the nanoparticle core (FIG. 3A) were tested. For this substrate, the rate of cleavage by MMP9 increased with increasing presentation distance (tether length) for all the substrate concentrations tested (0.5, 1.0, 2.0, 4.0 and 6.0 µM); as an example, cleavage velocity (V) increased from 0.24 to 0.96 nM s$^{-1}$ at 6 µM (FIG. 3B). Unexpectedly, this phenomenon was not generalizable across enzymes. For example, cleavage rates by the serine protease, thrombin, decreased with increasing presentation distance when the same substrate was tested (e.g., V at 6 µM of substrate decreased from 0.29 to 0.01 nM s$^{-1}$; FIG. 3C). Nor was it generalizable across substrates. For example, thrombin cleavage of a thrombin-selective substrate (fPRSGGG; lower case letter indicates $_D$-stereoisomer of the amino acid residue; SEQ ID NO: 16) was optimally presented at an intermediate length (FIG. 4). Taken together, these data indicate that it is possible to significantly augment the signal-to-noise ratio of ABNs by tuning presentation on the nanoparticle surface (FIG. 3D). The presentation of the MMP9 substrate on the ABNs described in this example exploited the increased on-target and decreased off-target protease cleavage that occurs for long tether lengths.

Next, localization of MMP9 ABN for sampling the tumor microenvironment in a living organism was investigated. In some embodiments, the benefit of tissue-level localization is magnified when applied to an activity-based system (e.g., ABNs), due to the synergy of accumulation and enzymatic amplification effects. To this end, a unique class of peptide ligands that mediate active internalization and transport of nanomaterials past tumor stroma and into the tumor tissue were employed; they are referred to here as tumor-penetrating peptides. In some embodiments, tumor-penetrating peptides are identified by phage-display screening.

The dual strategy of tuning MMP9-substrate presentation and increasing tumor-tissue access were applied to ABNs. Briefly, ABNs were decorated with the cyclic tumor-penetrating peptide, LyP-1 (CGNKRTRGC; SEQ ID NO: 1), which increases penetration of a variety of nanomaterials deep into the tumor parenchyma by binding its cognate receptor, p32, and engaging a secondary receptor, neuropilin-1 (NRP-1), which triggers an active transport pathway.

Figure 3E:
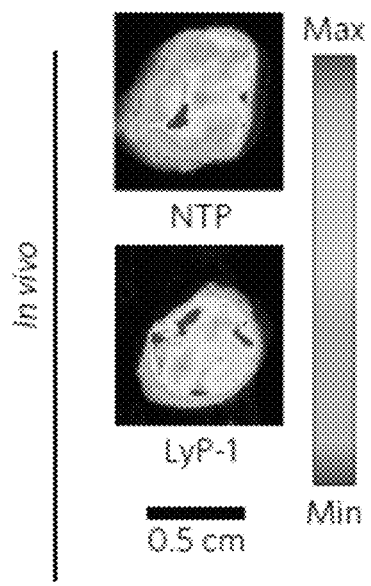
Figure 3F:
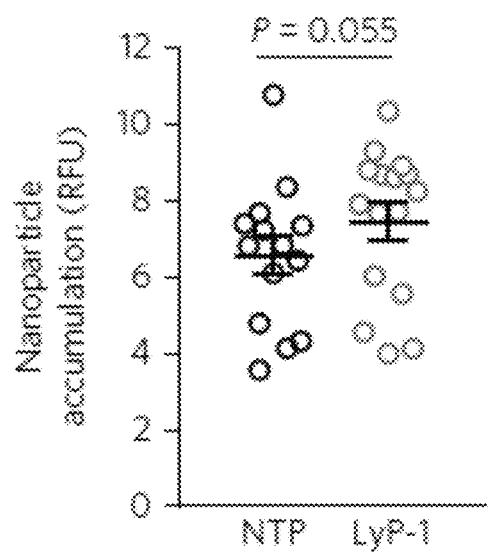
Figure 3G:
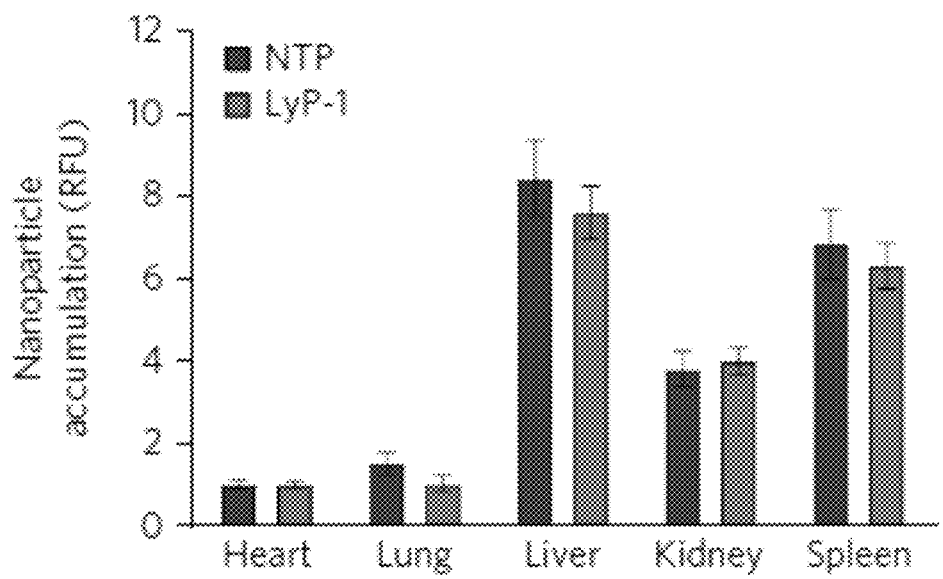

An MDA-MB-435 subcutaneous flank xenograft was used as a model of an epithelial tumor. MDA-MB-435 tumors have elevated p32[31] and MMP9[32] expression. Non-tumor-penetrating (NTP) and LyP-1 ABNs were matched for substrate valency (FIGS. 5A-5B) and were measured to have a ~60 nm hydrodynamic diameter and a slightly negative surface potential (FIG. 5C). Visualization of their fluorescent cores three hours after administration revealed that the amount of ABN accumulation in the tumors was similar to that in organs (FIGS. 3E-3G); addition of LyP-1 moderately increased tumoral accumulation (by ~20%) and resulted in slightly decreased off-target accumulation in organs, versus NTP ABNs (FIG. 3G).

Figure 3H:
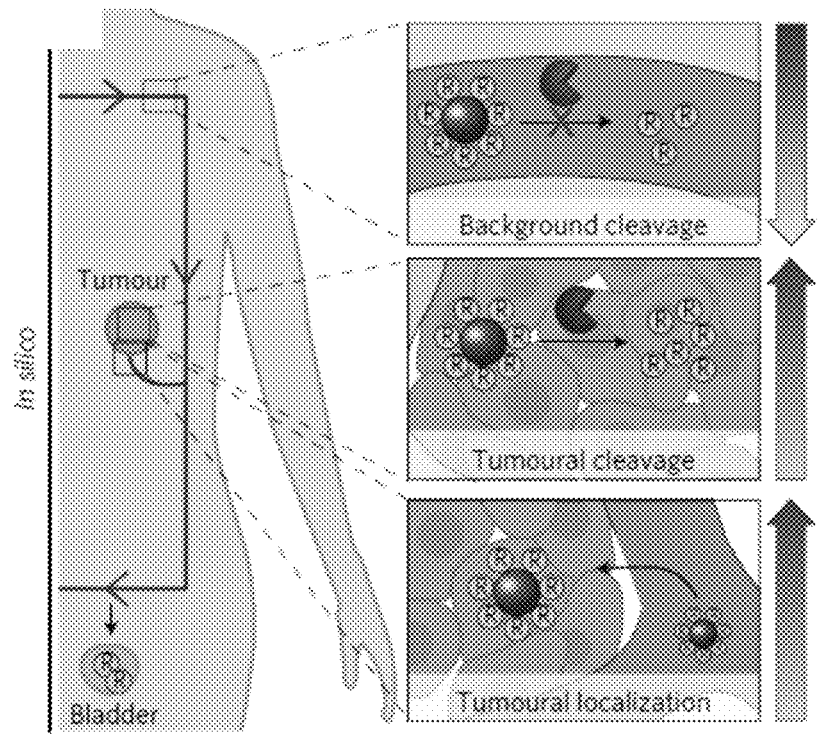
Figure 3I:
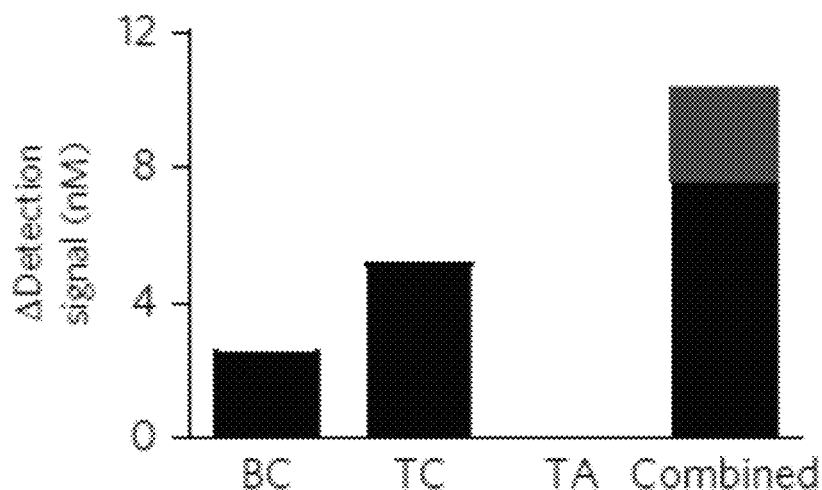
Figure 3J:
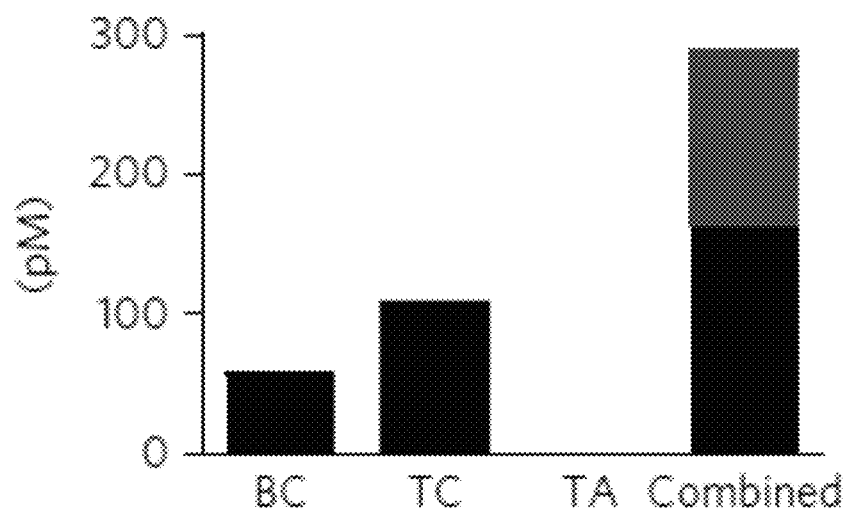
Figure 3K:
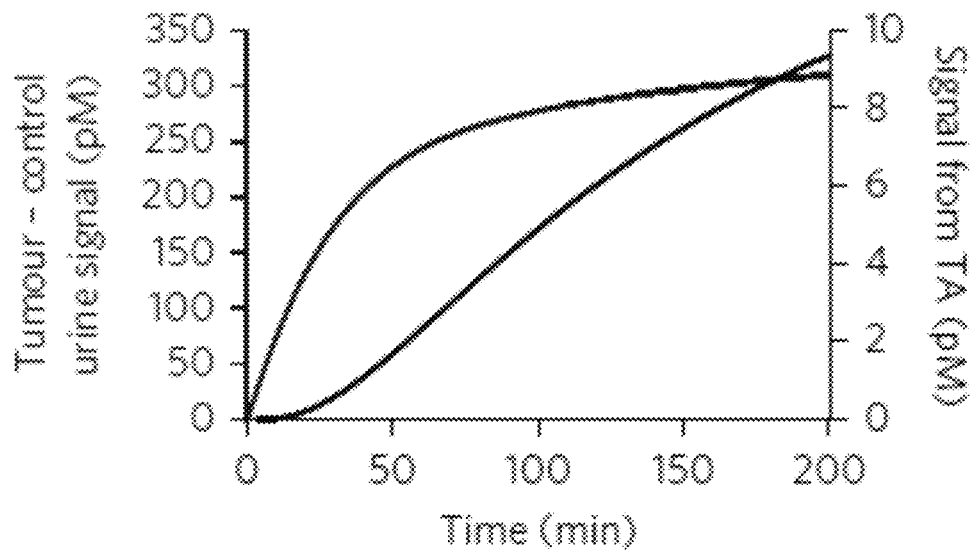

A pharmacokinetic mathematical model was used as a tool to understand how modifications affect the performance of ABNs. The model comprises a set of five ordinary differential equations solved in three separate compartments (blood, tumor and bladder). The equations are derived from transport and biochemical governing equations (e.g., Fick's Law and Michaelis-Menten kinetics) with variables fit to experimental data. On the basis of the in vitro and in vivo experimental ABN data presented in this example (FIGS. 3A-3G), three parameters of the model were modified: tumor-protease-specific cleavage ($k_{cat}^{MMP9}$), off-target cleavage ($k_{cat}^{blood}$) and tumoral accumulation ($k^{NP}_{tumor}$) (cat, catalysis; NP, nanoparticle; FIG. 3H). When applied to tumors of moderate size (10 mm diameter), the model indicated cooperation between the three parameters: increases in detection signal were greater when parameters were input simultaneously compared with the sum of each parameter input individually (FIG. 3I, light shaded bar). The model indicated negligible enhancement of the detection signal to increased tumoral accumulation by itself. When the same analysis was applied to small tumors (5 mm diameter), similar trends were observed (FIG. 3J). The model indicated interactions between parameters to be greater for these smaller tumors, suggesting that multi-parameter tuning is important when engineering ABNs for detection of small tumors. Lastly, the benefit of improved accumulation when combined with the other two parameters was examined. This was assessed by measuring the difference in the detection signal when all three parameters were input versus when just the modified protease cleavage parameters were input (FIG. 3K).

Tumor-Penetrating ABNs Detect Sub-5 mm Diameter Tumors

Figure 6A:
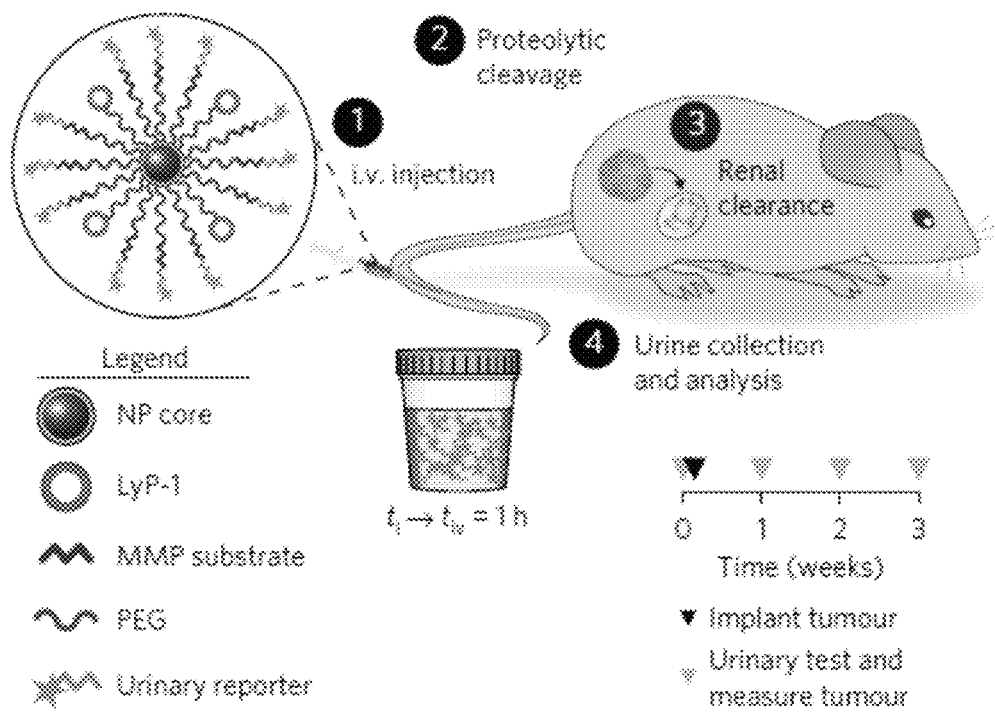
FIGS. 6A-6E show tuned ABNs detect sub-5 mm diameter tumors.
Figure 6B:
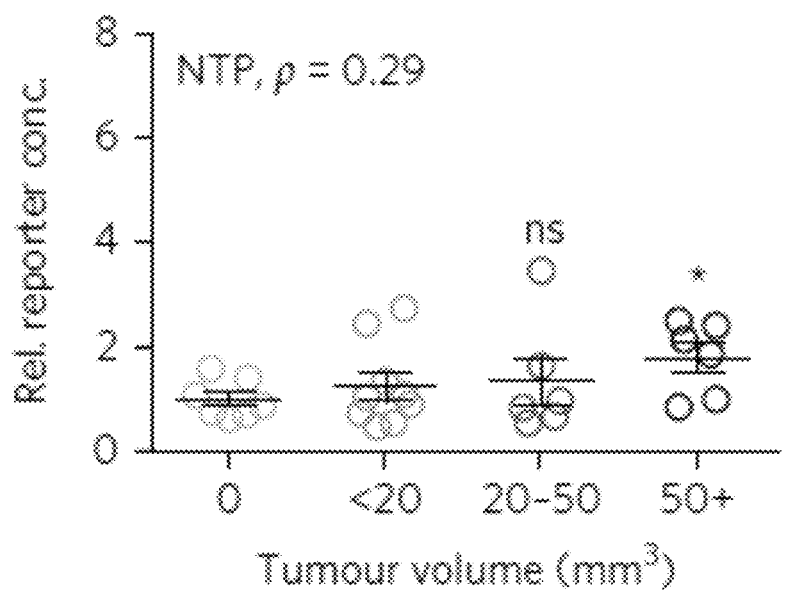
Figure 6C:
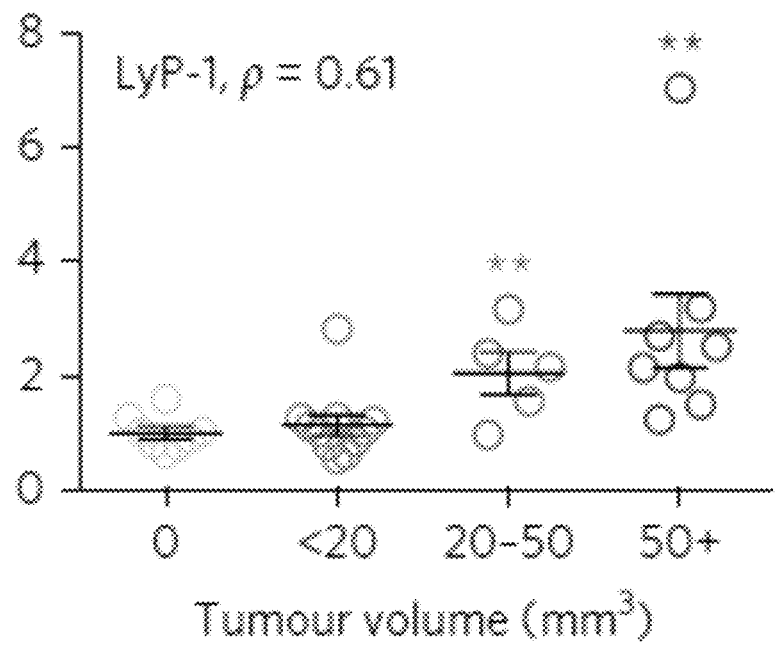
Figure 6D:
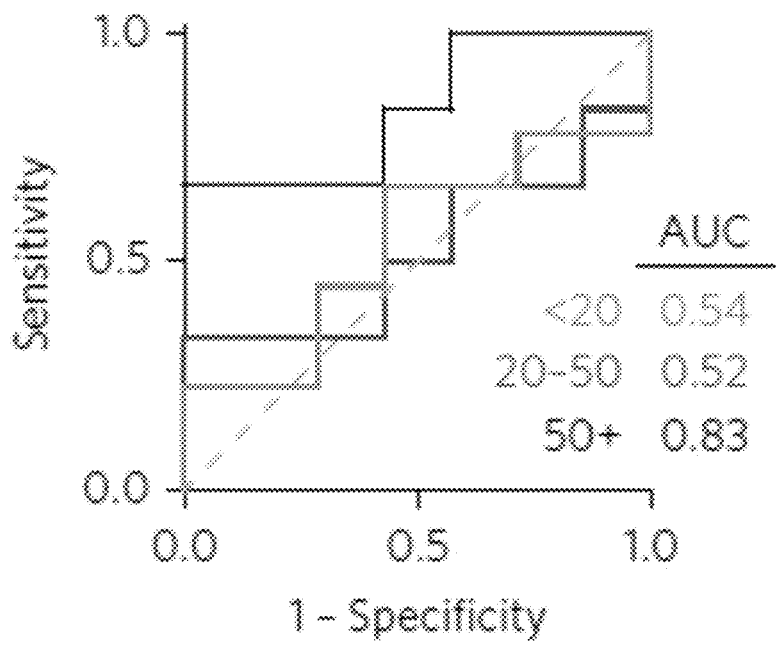
Figure 6E:
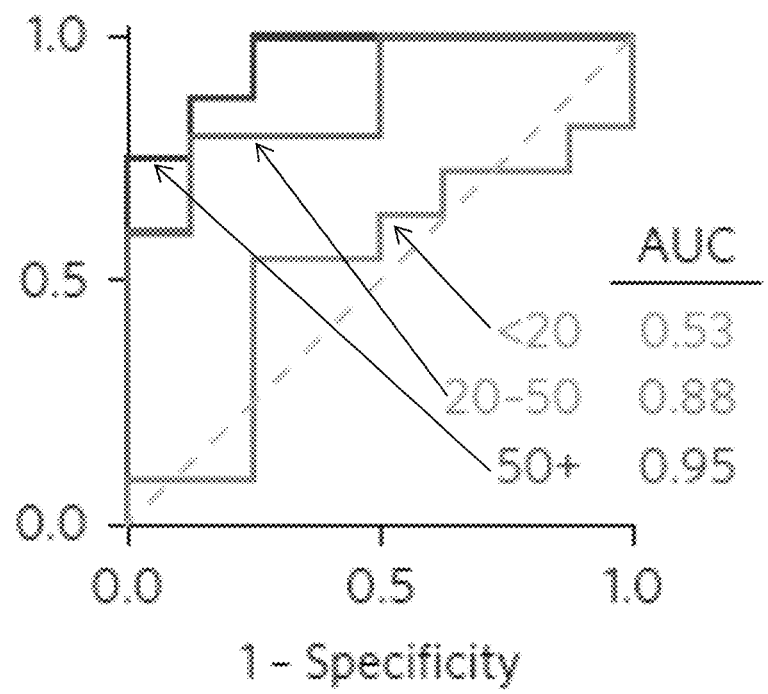
Figure 7A:
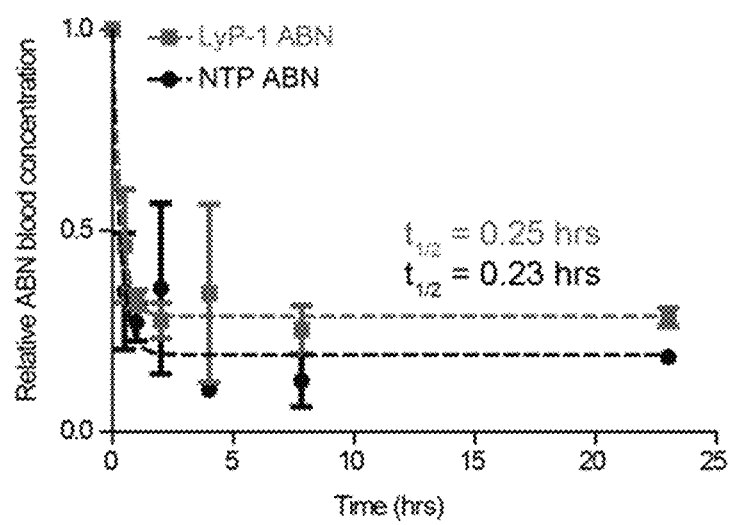
FIGS. 7A-7B show half-life measurements of ABN and free reporter.
Figure 7B:
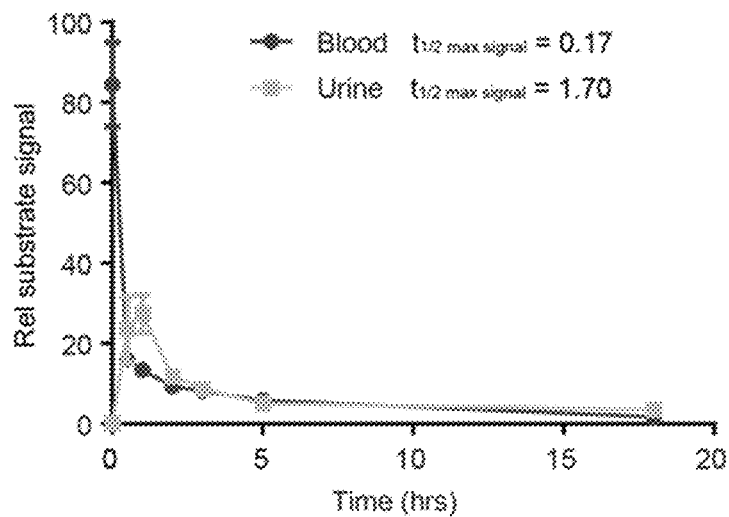
Figure 8A:
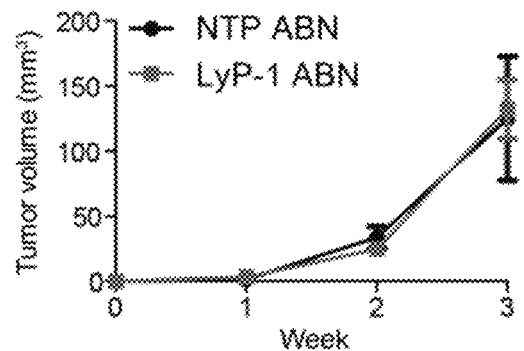
FIGS. 8A-8E show growth characteristics and urine signals of MDA-MB-435 flank xenograft.
Figure 8B:
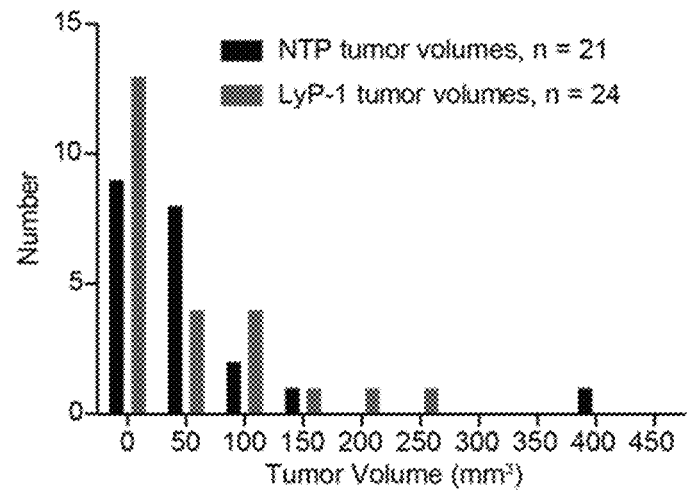
Figure 8C:
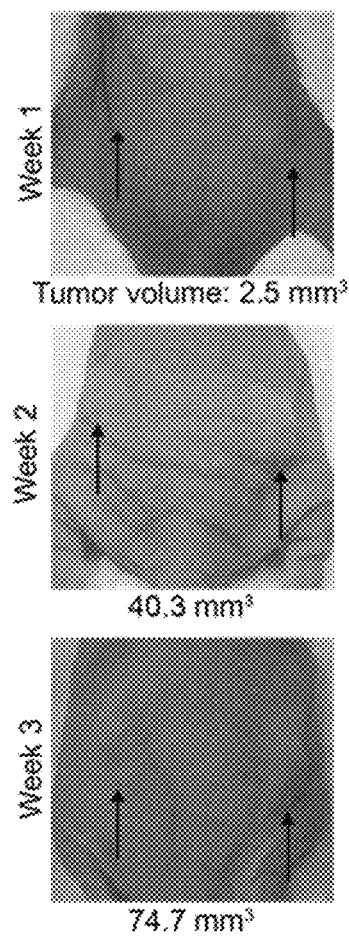
Figure 8D:
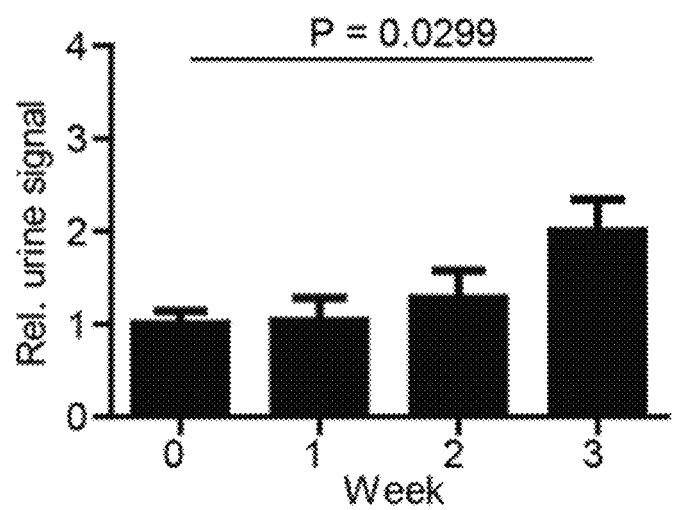
Figure 8E:
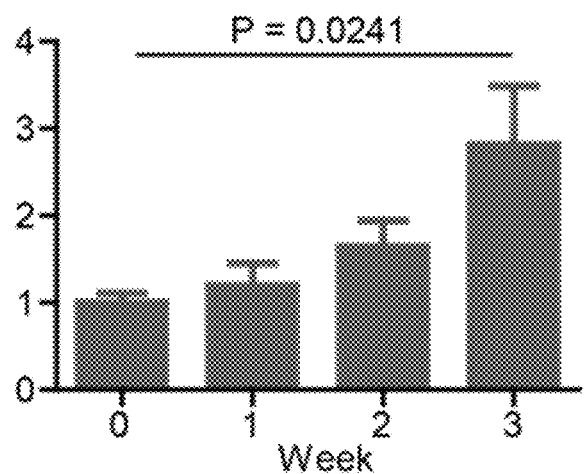

The minimum size of tumors that could be detected using tumor-penetrating ABNs was investigated. A urinary test (e.g., measurement of peptide fragments in the urine 1 h after ABN administration) was performed at 1, 2 and 3 weeks after initial tumorigenesis of MDA-MB-435 to xenografts (FIG. 6A). Measurement of ABN half-life in the blood and the free substrate clearance in the blood and urine indicated that the signal decayed rapidly, with half-lives being far shorter than the seven-day intervals between particle administrations (FIGS. 7A-7B). At the time of each weekly urine test, the total tumor volume per mouse was measured, as determined by caliper measurements (FIGS. 8A-8C). Non-penetrating ABNs with tuned MMP9 substrate presentation discriminated tumors that were ~150 mm³ in volume (FIG. 6B)—these volumes are approximately threefold smaller than those achieved when the substrate was directly presented on the nanoparticle surface. Consistent with the in silico analysis that indicated multi-parameter tuning would have a greater effect at small tumor sizes (FIG. 3J), the addition of tumor-penetrating ligands reduced the detection size limit to between 20 and 50 mm³, corresponding to tumor diameters of 3.4-4.6 mm (FIG. 6C). ROC analysis for tumor volumes of ≥50 mm³ yielded an AUC of 0.83 for non-penetrating ABNs (FIG. 6D) compared with 0.95 for LyP-1 ABNs (FIG. 6E), indicating that LyP-1 increased the diagnostic power of the ABNs. Urine signals were also elevated when tracked over time (FIGS. 8D-8E). The tumor-penetrating ligands markedly improved the urinary detection limit, reducing it from 150 mm³ to 30 mm³, despite their relatively moderate effect (1.2-fold increase) on accumulation. In some embodiments, this unanticipated dramatic enhancement may be explained by biological phenomena such as cell- and tissue-level distribution. Taken together, the combination of tuning of substrate presentation and tumor-penetration improved the size limit for detectable tumors by over an order of magnitude (~14-fold), compared with limits of ~500 mm³ for previous technology without these modifications.

ABNs Outperform a Clinical Test in an Ovarian Cancer Model

Early detection of ovarian cancer could yield substantial improvements in patient prognosis. Due to inadequate detection methods, 80% of current cases are diagnosed after the tumor has spread past the ovary. In addition, 70% of ovarian cancer patients relapse after being treated according to the standard of care, and therefore would greatly benefit from point-of-care longitudinal monitoring for early indications of relapse.

Figure 9A:
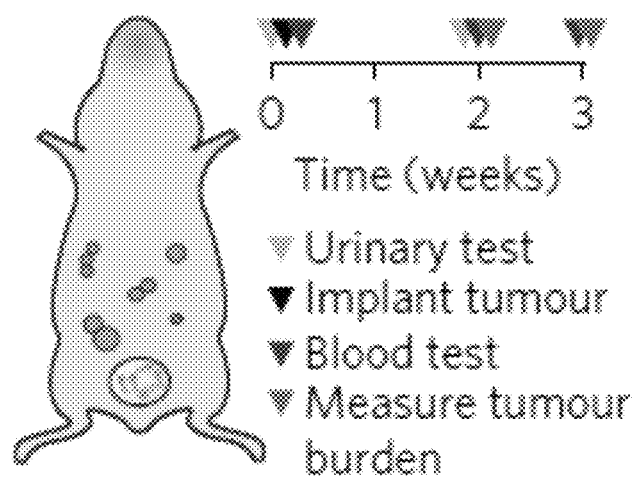
FIGS. 9A-9G show urinary biomarkers outperform blood biomarkers in detecting millimeter-sized lesions in orthotopic xenograft models of ovarian cancer.
Figure 9B:
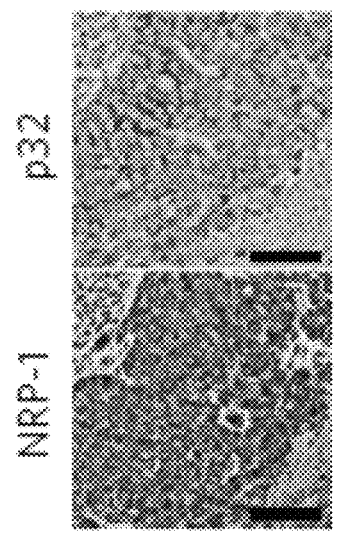
Figure 9C:
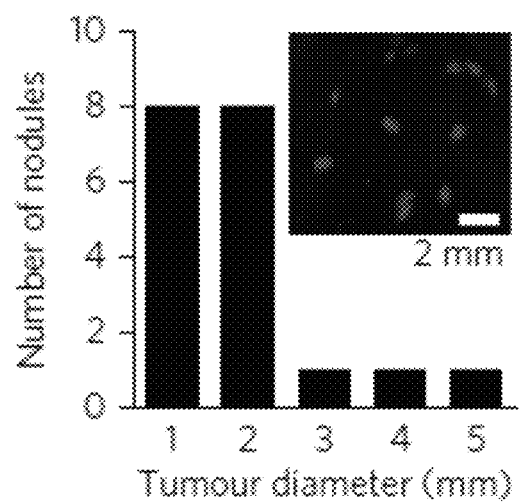
Figure 9D:
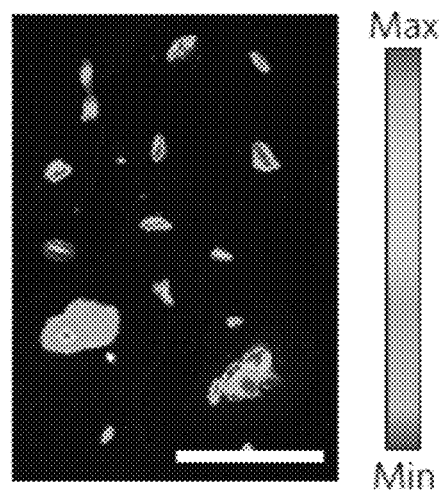
Figure 9E:
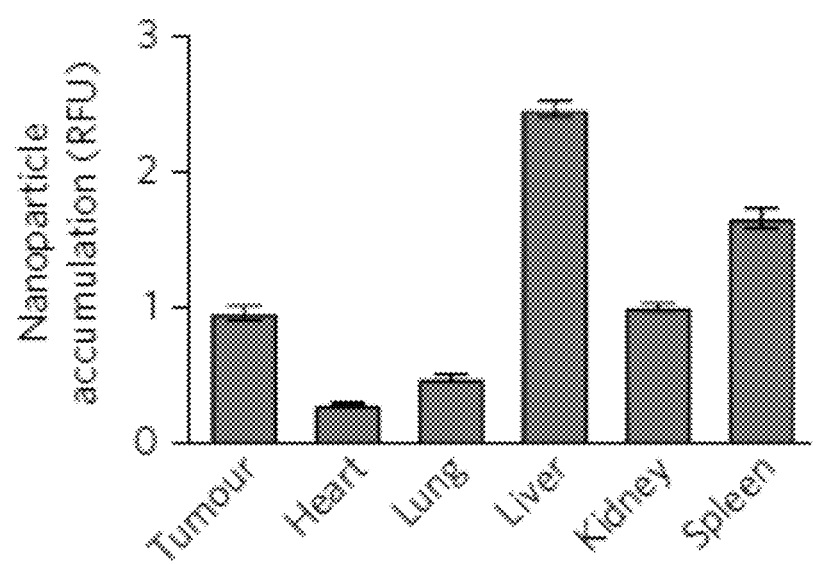
Figure 10A:
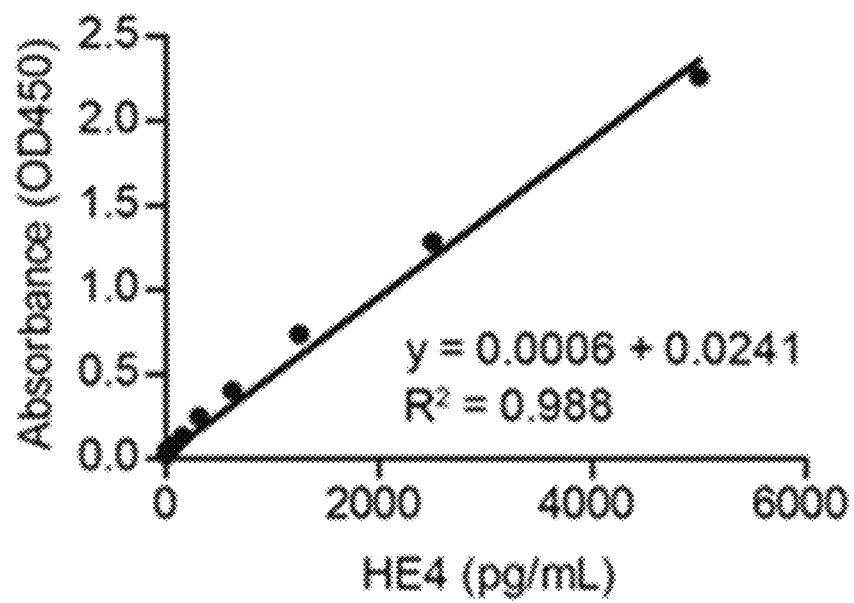
FIGS. 10A-10F show HE4 secretion rates across several ovarian cancer lines.
Figure 10B:
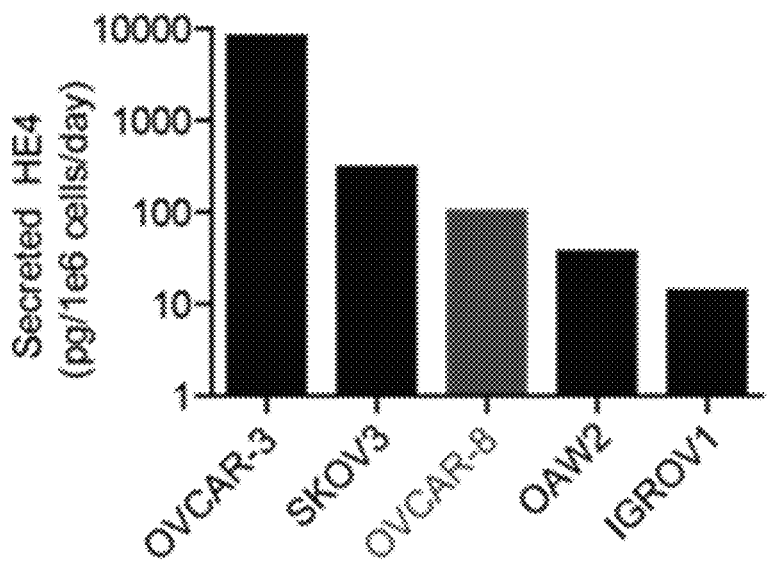
Figure 10C:
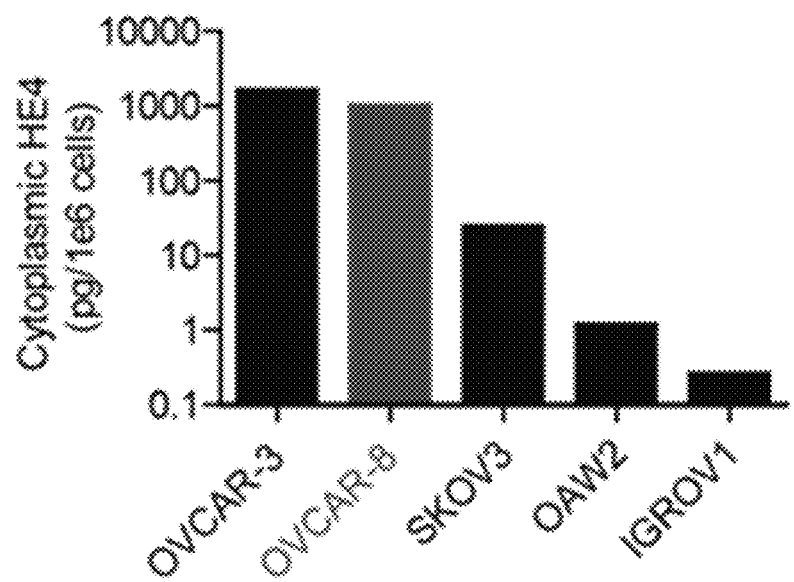
Figure 10D:
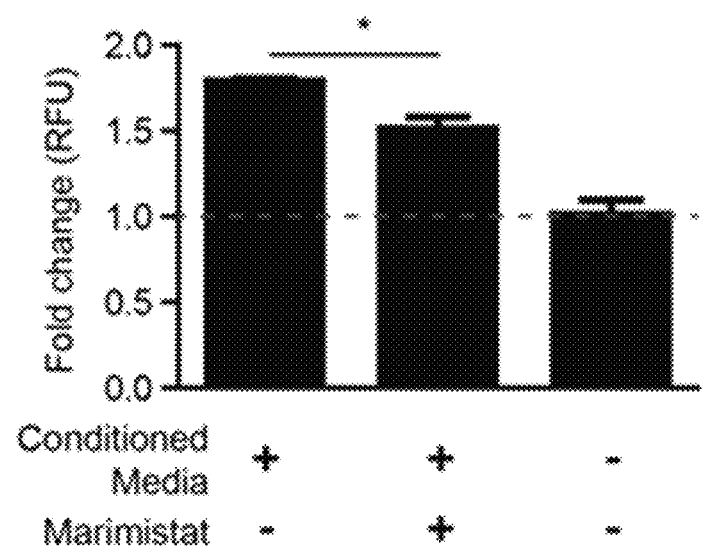
Figure 10E:
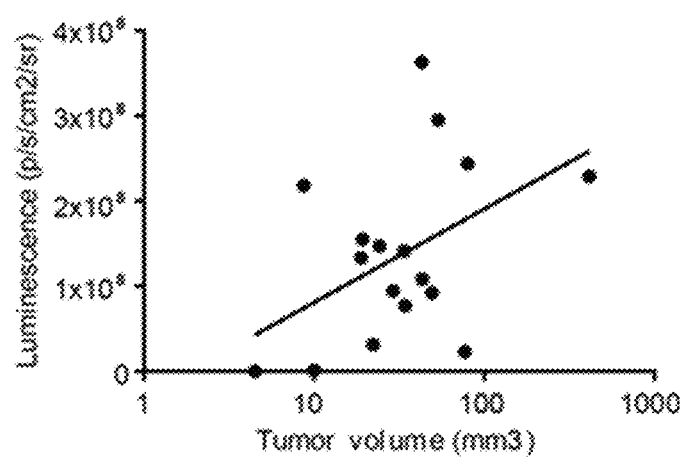
Figure 10F:
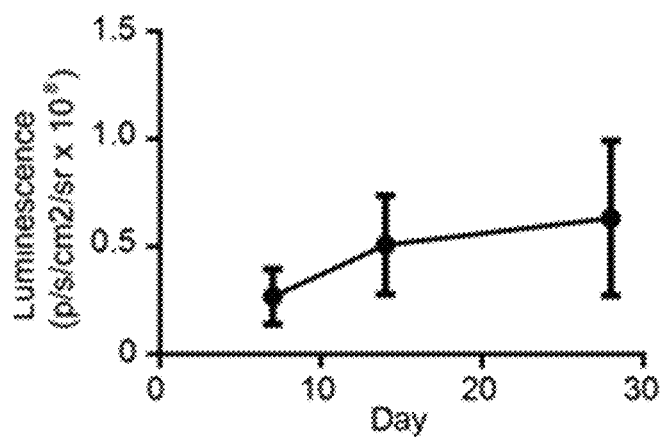
Figure 11A:
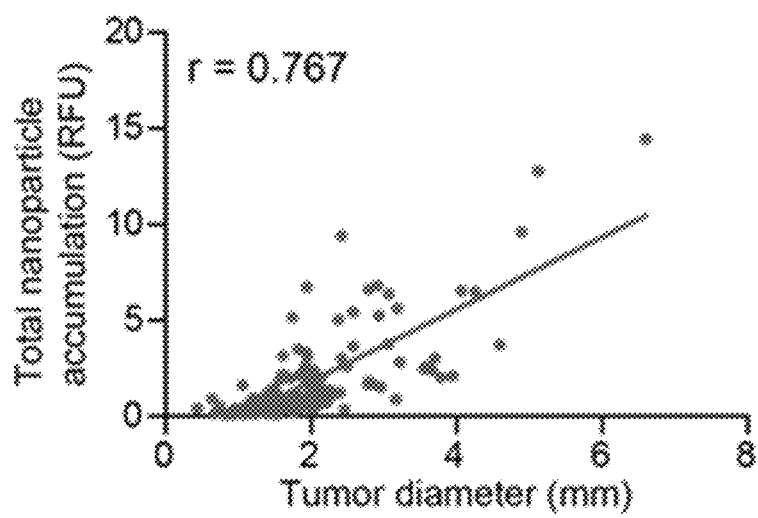
FIGS. 11A-11G show urinary biomarker performance in the ovarian cancer model.

The tumor-penetrating ABN platform was used to detect a low tumor burden in an orthotopic disseminated xenograft model of high-grade serous ovarian cancer. The mouse model was established by intraperitoneal implantation of the human cell line OVCAR-8 (FIG. 9A), which displays surface p3234 and NRP-1 (FIG. 9B), and secretes human epididymis to protein (HE4) (FIGS. 10A-10C) and MMP9. It was observed that OVCAR-8 conditioned media can cleave the MMP9 substrate, and that this activity can be inhibited by the broad-spectrum matrix-metalloprotease inhibitor, marimistat (FIG. 10D). Growth of tumors was monitored by bioluminescence tracking of luciferized cells (FIGS. 10E-10F). When implanted into the peritoneal space of mice, OVCAR-8 cells form disseminated tumor nodules (timescale of weeks) and the mice eventually accumulate ascites (timescale of months)-two disease presentations that also occur in human ovarian cancer patients. Two weeks after initial tumorigenesis, mice showed no overt signs of illness and had an average total tumor burden of 36 mm³ with a median nodule diameter of <2 mm (FIG. 9C and FIG. 11). After intravenous ABN administration, resected tumors showed significant accumulation of nanoparticles (FIG. 9D-9E) and the total tumoral accumulation depended strongly on tumor size (FIG. 11A).

Figure 9F:
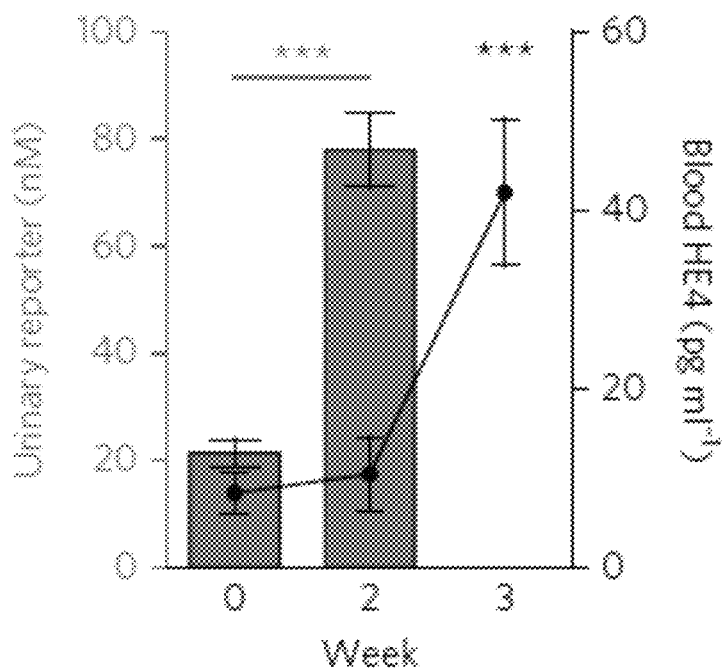
Figure 9G:
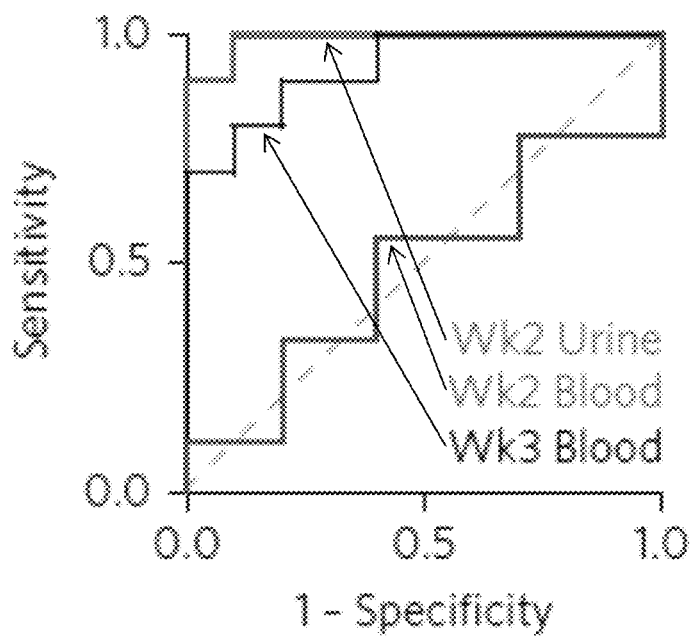
Figure 11B:
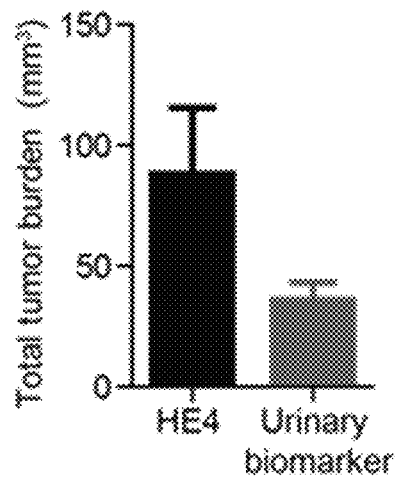
Figure 11C:
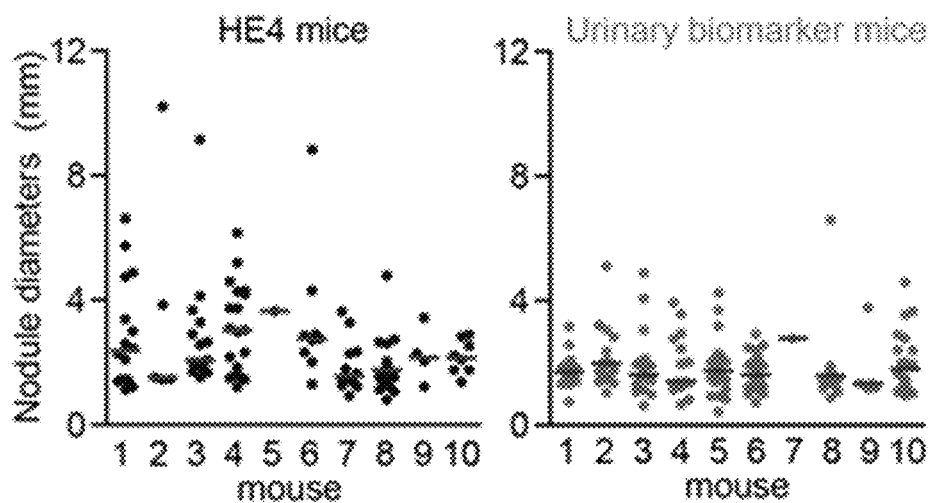
Figure 11D:
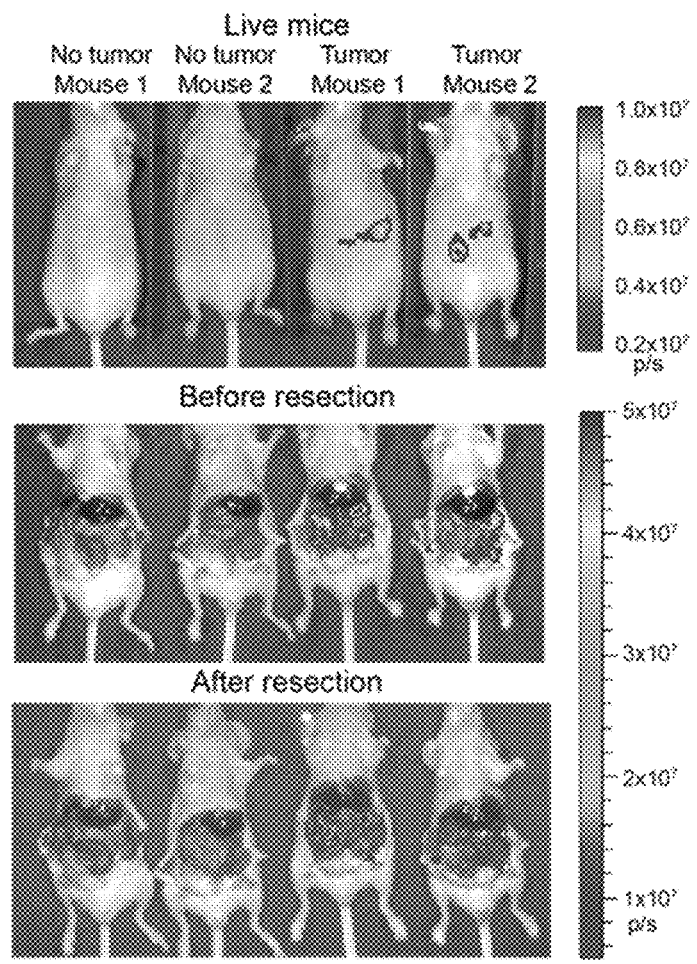
Figure 11E:
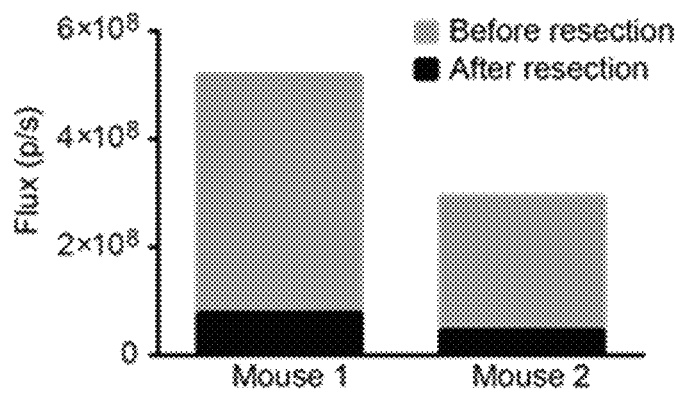
Figure 11F:
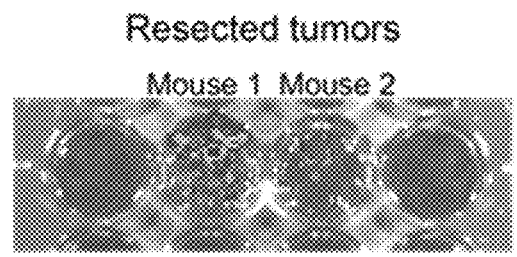
Figure 11G:
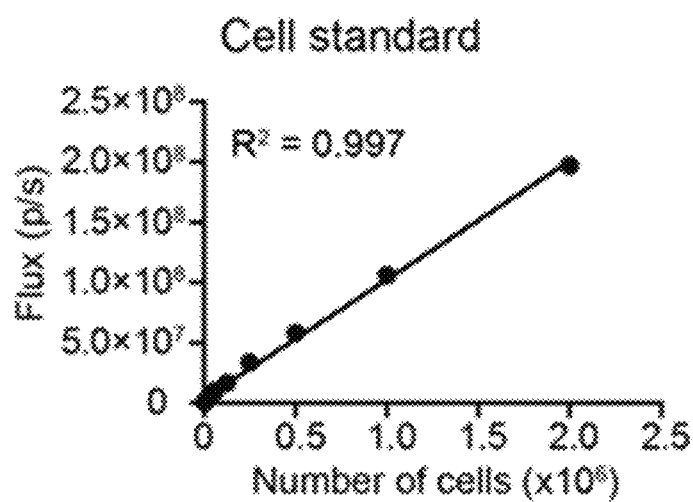

The ability of ABNs to: (1) detect low-burden ovarian cancer and (2) outperform a clinical blood biomarker were tested. Detection by ABNs was compared to the blood biomarker HE4, as OVCAR-8 cells produce relatively high levels of this protein, on a par with four other human ovarian cancer cell lines (FIGS. 10B-10C). At a total tumor burden of 36 mm³, the urinary signal from the ABNs was significantly elevated versus mice with no tumors (FIG. 9F). This threshold of sensitivity is critical, as clinically approved imaging modalities can typically only resolve individual tumor nodules greater than 5 mm in diameter. Additionally, it has been estimated that to decrease serous ovarian cancer mortality by 50% with an annual screen, a test would have to be sensitive to tumors of <5 mm. In contrast, the blood biomarker HE4 was not elevated to detectable levels at this time point and was only significantly elevated three weeks post-tumorigenesis, when the average total burden was 88 mm³ (FIG. 9F and FIGS. 11B-11C). A comparison of the two diagnostic systems' detection powers indicated that ABN performance at two weeks (ROC–AUC=0.99) exceeded that of HE4 at two weeks (ROC–AUC=0.51) and three weeks (ROC–AUC=0.93), with improvements in the true positive and true negative rates (FIG. 9G). It was confirmed that the tumor nodule retrieval methodology described in this example accounted for greater than 80% of the tumor burden by measuring luminescence pre and post-resection (FIGS.

11D-11G). The tumor burden remaining can be attributed to uncollected macroscopic and microscopic lesions.

The difference in the tumor volumes detected via an enzyme-linked immunosorbent assay (ELISA) of serum HE4 and those detected using the tumor-penetrating ABNs was 2.4-fold. Typically, early stage human serous ovarian carcinomas have a doubling time of four months. Extrapolating the benefit seen in detection compared with HE4 and assuming a simple monoexponential growth model of human ovarian cancer ($N_T(t)=N_{T,0}e^{(ln2/[DT])t}$, where $N_T$ is the starting tumor size and DT is the doubling time), diagnosis could occur five months sooner for ABNs versus the blood biomarker. Improving diagnosis time by five months could significantly impact the prognosis of ovarian cancer patients, especially when it is considered that ovarian cancers spend an average of one year at stages III and IV before they become clinically apparent.

Ligand-Receptor Matching Improves ABN Urinary Signal

Figure 12A:
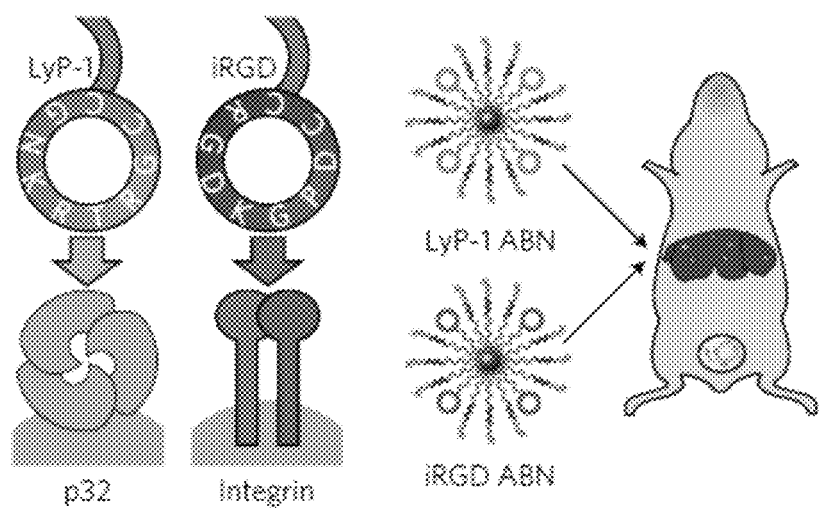
FIGS. 12A-12G show minimally invasive receptor classification of syngeneic liver metastasis via targeted ABNs.
Figure 12B:
Figure 12C:
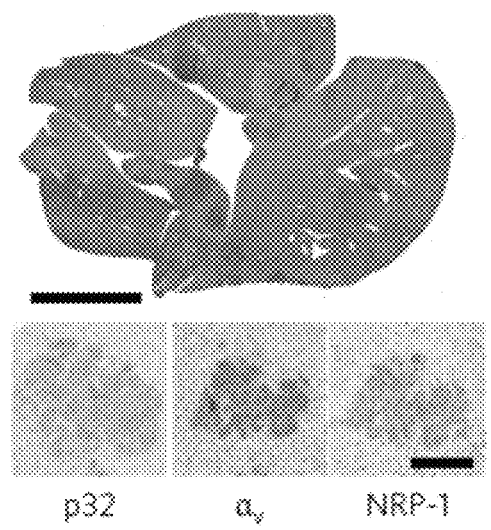
Figure 12D:
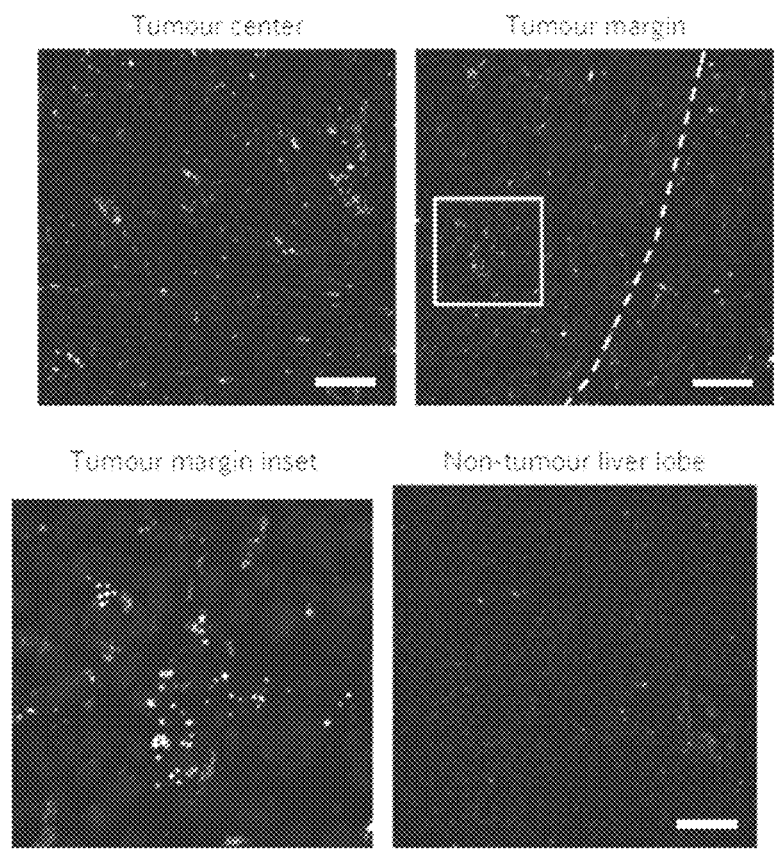
Figure 14A:
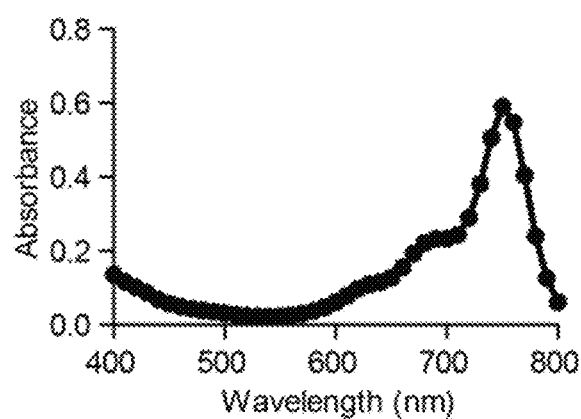
FIGS. 14A-14B show iRGD ABNz characterization.
Figure 14B:
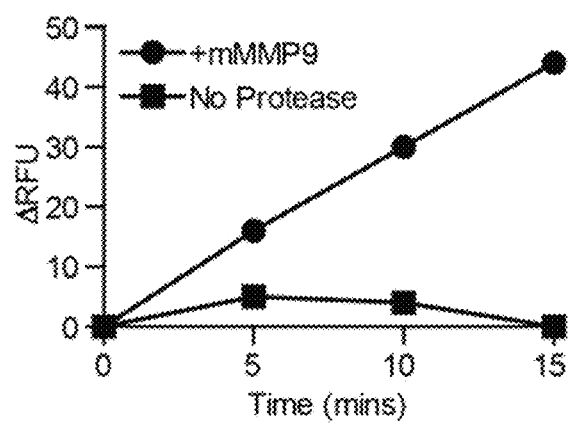
Figure 15A:
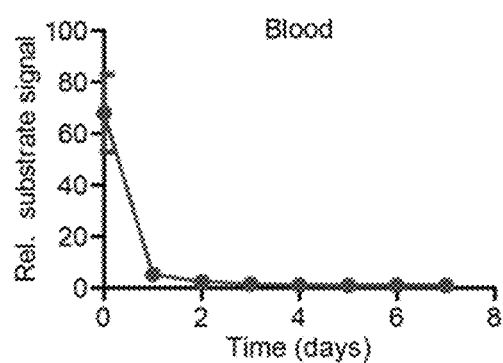
FIGS. 15A-15D show clearance of ABN in vivo. BALB/c mice were injected with iRGD ABN intravenously and fluorescence was measured in (FIG. 15A) blood and (FIG. 15B) urine every 24 hours for 7 days.
Figure 15B:
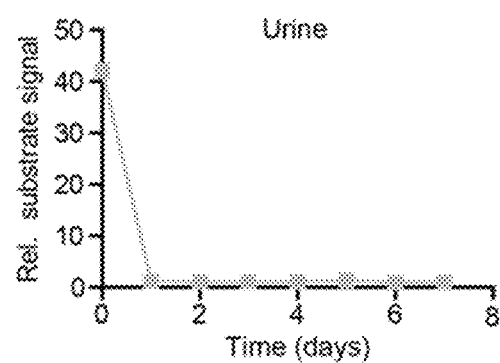
Figure 15C:
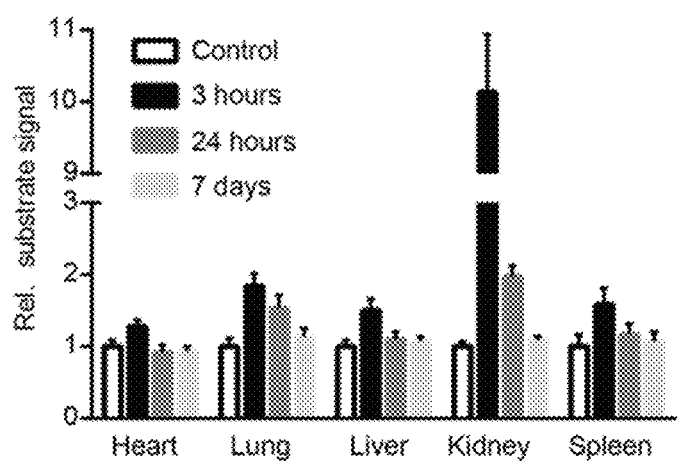
Figure 15D:
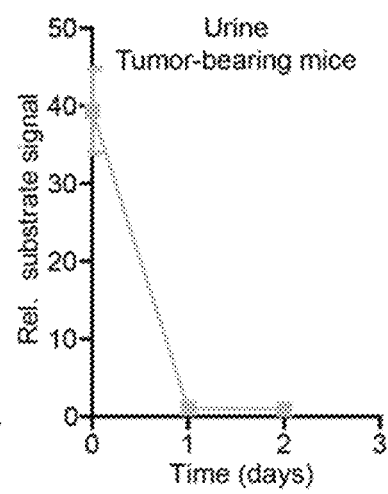
Figure 16:
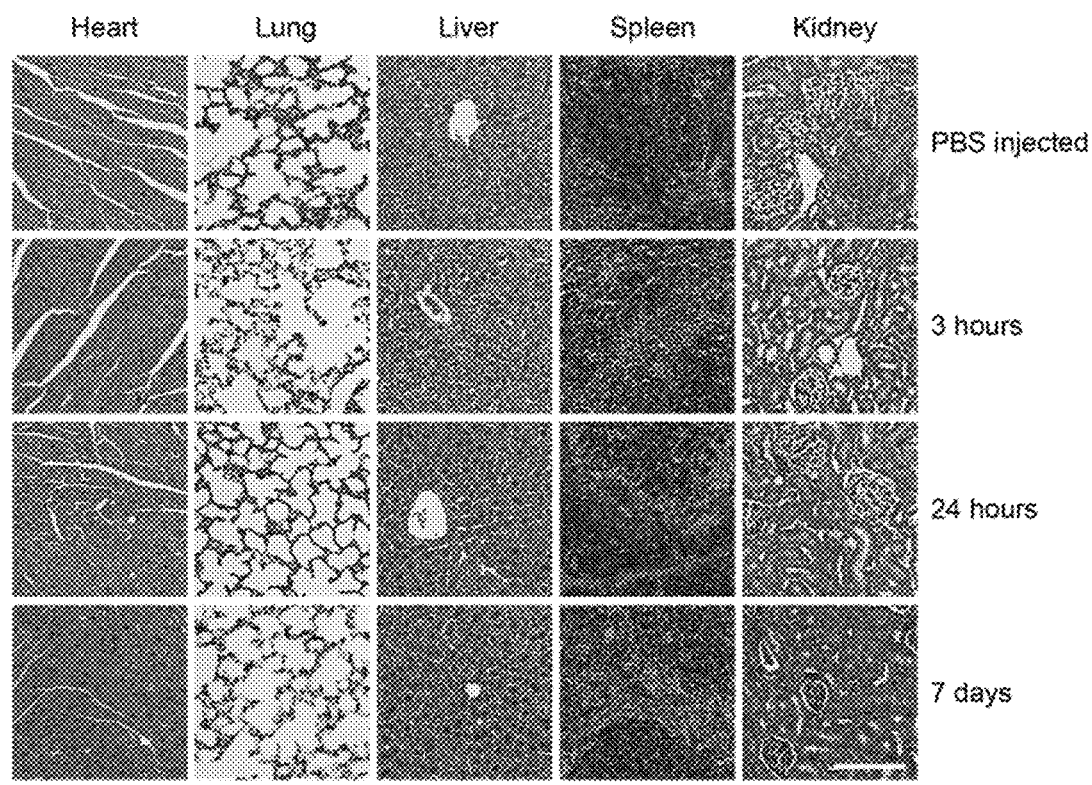
FIG. 16 shows toxicity screening of ABN. Immunocompetent BALB/c mice were injected with iRGD ABN, and organs (heart, lung, liver, spleen, and kidney) were collected at 3 hours, 24 hours, and 7 days after administration. Organs were fixed, embedded in paraffin, and stained with hematoxylin & eosin. Analysis by a veterinary pathologist confirmed that tissue from ABN injected animals appeared similar to PBS injected control. Study was done with n=3 mice and images from a representative animal are shown. Scale bar represents 100 µm.

Receptor expression on tumors varies by tumor type and patient. In this example, another ABN was produced using the tumor-penetrating ligand, iRGD (CRGDKGPDC; SEQ ID NO: 2). This peptide engages the same active-internalization pathway as LyP-1, but binds to $\alpha_v\beta_3$ or $\alpha_v\beta_5$ integrin heterodimers as its primary receptor, which are ectopically overexpressed in a large subset of cancers (FIG. 12A). The tumor-targeting peptides iRGD and LyP-1 were bound to ABNs and administered to an immunocompetent mouse model of colorectal liver metastasis (CLM), induced via an intrasplenic injection of p32-negative, integrin-positive and NRP-1-positive MC-26 cells (FIG. 12B-12C and FIGS. 13A-13C). MC-26 cells are derived from a mouse colorectal cancer line and secrete MMP9, which can be detected in the tumor nodules as well as in the tumor-adjacent liver, but not in non-tumor-bearing liver lobes (FIG. 12D). The stoichiometries for substrate conjugation on iRGD ABNs were similar to those used on the LyP-1 ABNs (FIG. 14A). Mouse and human MMPs exhibit a high degree of homology, and it was confirmed that mouse MMP9 cleaves the ABN MMP9 substrate (SEQ ID NO: XX; FIG. 14B). A study of ABN clearance in immunocompetent BALB/c mice indicated that no signal was detectable after 24 h in the urine, 48 h in the blood and 7 d in the tissues (FIGS. 15A-15C). This was consistent in the model of orthotopic ovarian cancer (FIG. 15D). Furthermore, no signs of toxicity were observed via histopathological assessment of tissues 3 h, 24 h and 7 d after ABN administration, when compared with PBS-injected controls (FIG. 16).

Figure 12E:
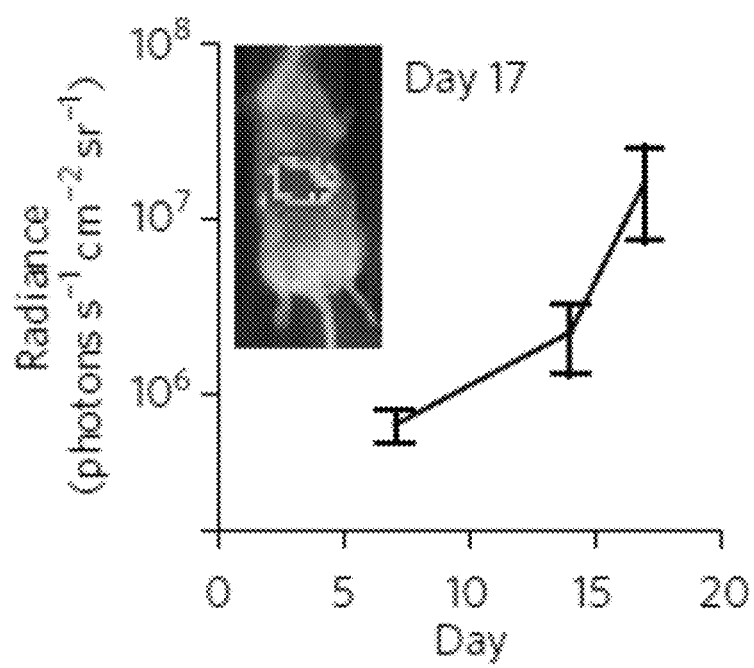
Figure 12F:
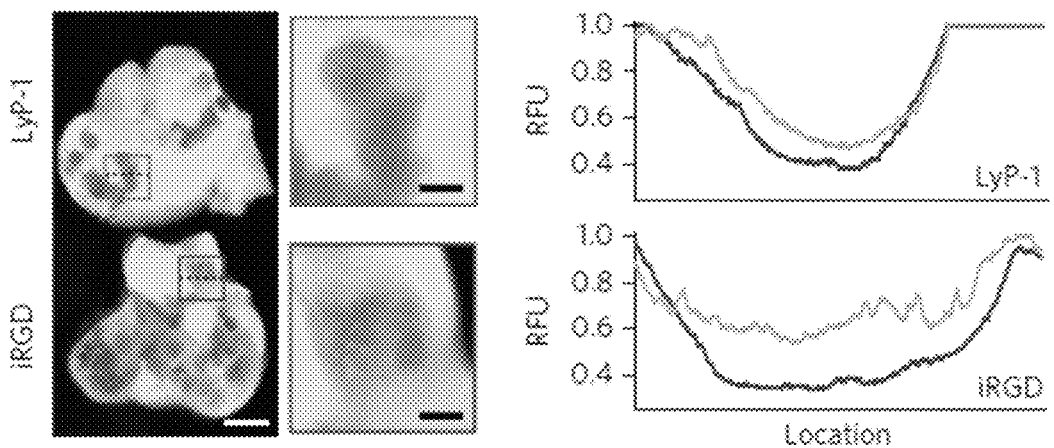
Figure 12G:
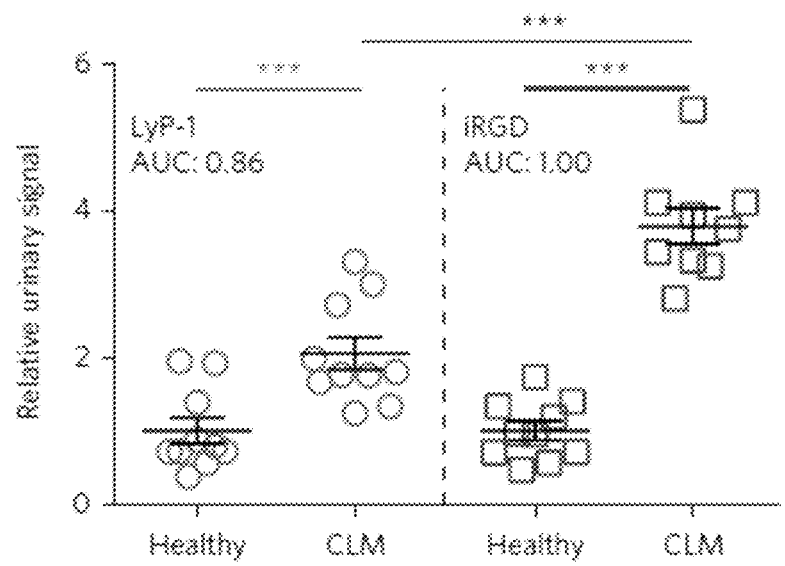
Figures 13A, 13B, 13C:
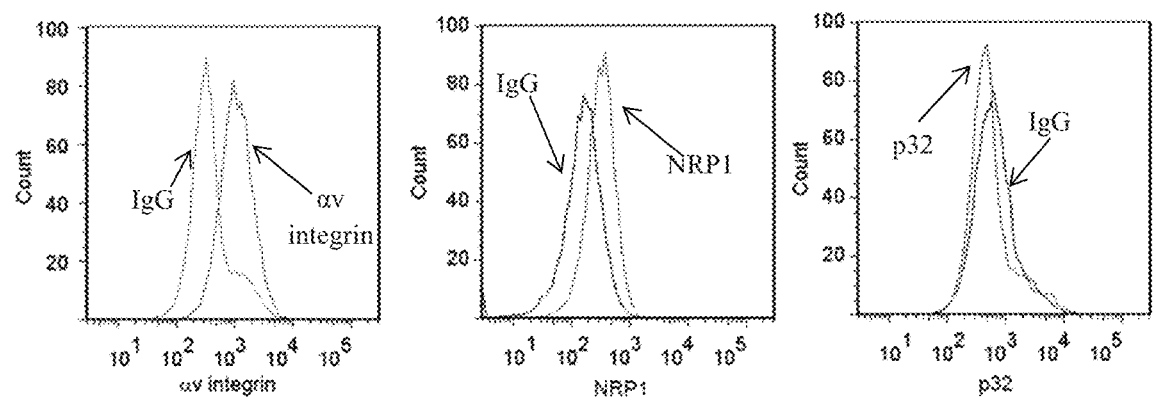
FIGS. 13A-13C show MC26 cell line surface marker analysis by flow cytometry.
Figure 17:
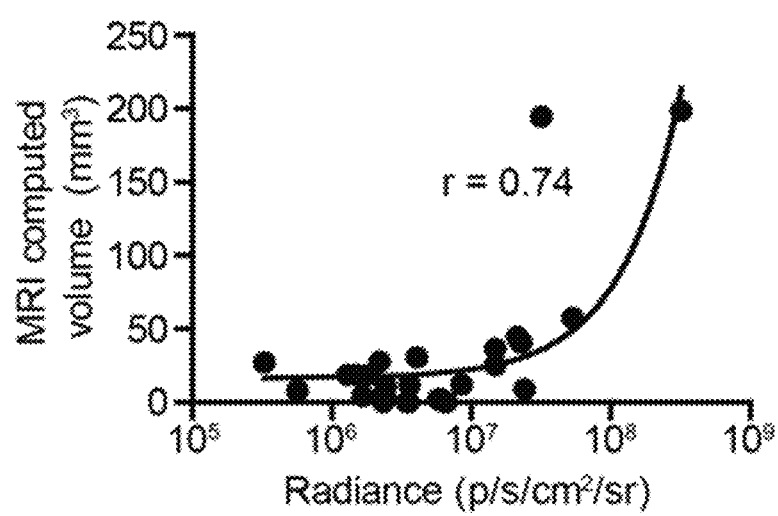
FIG. 17 shows correlation between MRI computed tumor volume and bioluminescence. MRI and bioluminescence measurements were made by two separate, blinded operators (r: Pearson's correlation).
Figure 18A:
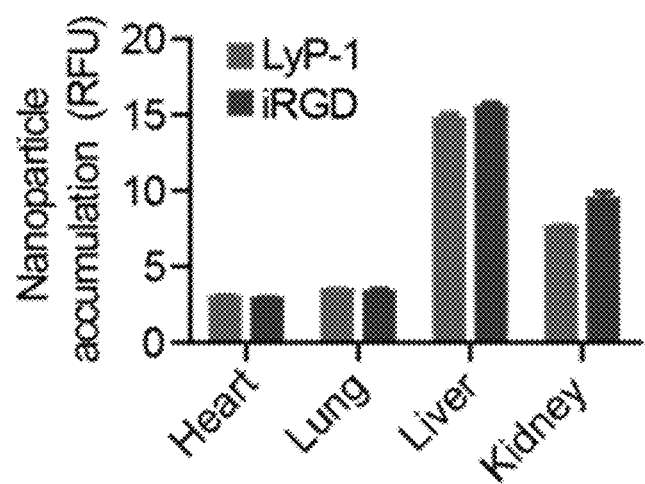
FIGS. 18A-18C show imaging of nanosensor localization.
Figure 18B:
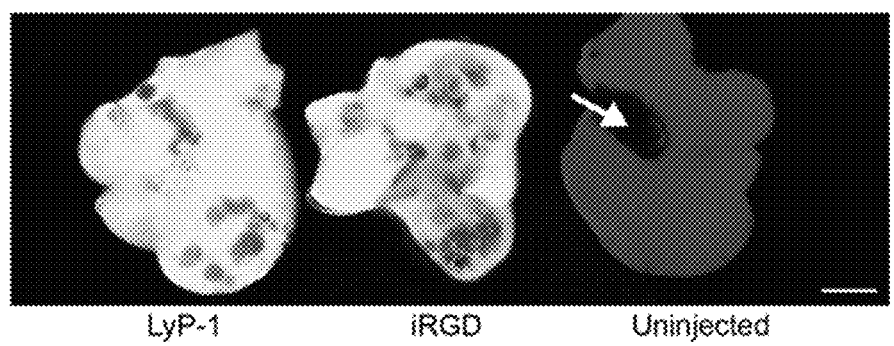
Figure 18C:
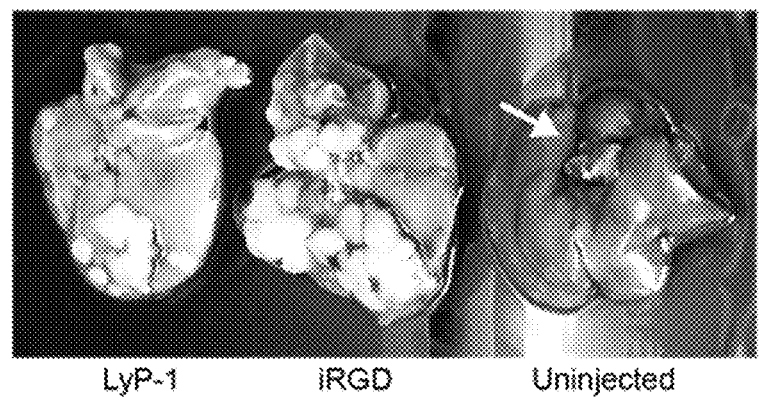

The growth of individual liver metastases was measured by MRI and was well-correlated with the bioluminescence signal of luciferized MC-26 cells, allowing monitoring of total tumor burden via bioluminescence imaging (FIG. 12E and FIG. 17). Nanoparticle (e.g., ABN) localization after intravenous administration of iRGD or LyP-1 ABNs was examined, and no changes in overall peri- and intra-organ accumulation were observed (FIG. 18A), but increased to penetration of iRGD ABNs into the tumor metastases compared with LyP-1 (FIG. 12F and FIGS. 18B-18C). Application of either LyP-1 or iRGD ABNs in the urinary test resulted in distinct increases in signal when applied to mice with CLM compared with healthy mice (FIG. 12G) and those that underwent sham surgeries (FIG. 19). Consistent with low p32 and high integrin surface expression on MC-26 tumors (FIG. 12C), iRGD ABNs exhibited significantly improved diagnostic performance with relative reporter concentration increases that were greater than those for LyP-1 ABNs (AUC=1.00 versus 0.86, respectively). The urine signal was also more positively correlated with overall burden for iRGD versus LyP-1 ABNs (FIG. 19B). Administration of LyP-1 ABNs to CLM mice resulted in relative reporter concentration increases similar to those for non-penetrating ABNs administered in the hind flank model (FIG. 8B), thereby indicating that the presence of the primary receptor enhances the urinary signal.

ABN Zymography Tool Evaluates Substrates in Human Tissues

Figure 20B:
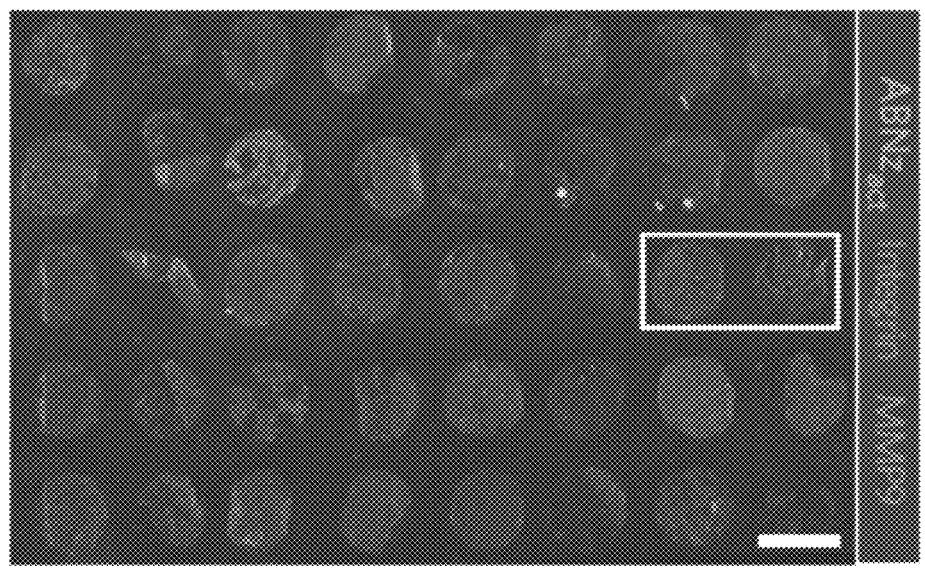
Figure 20C:
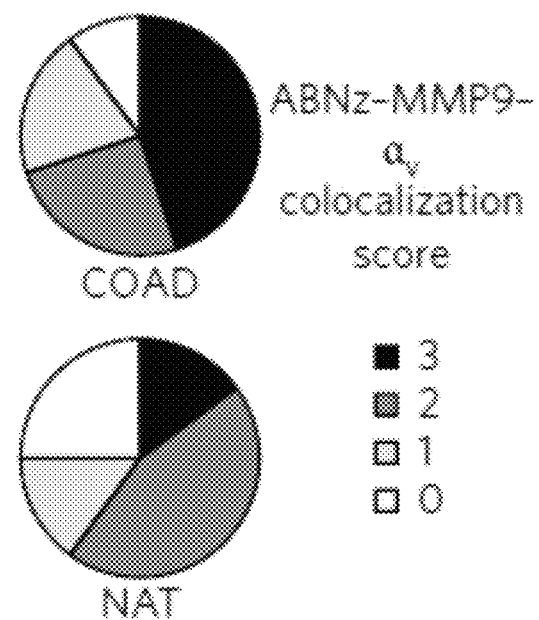
Figure 20D:
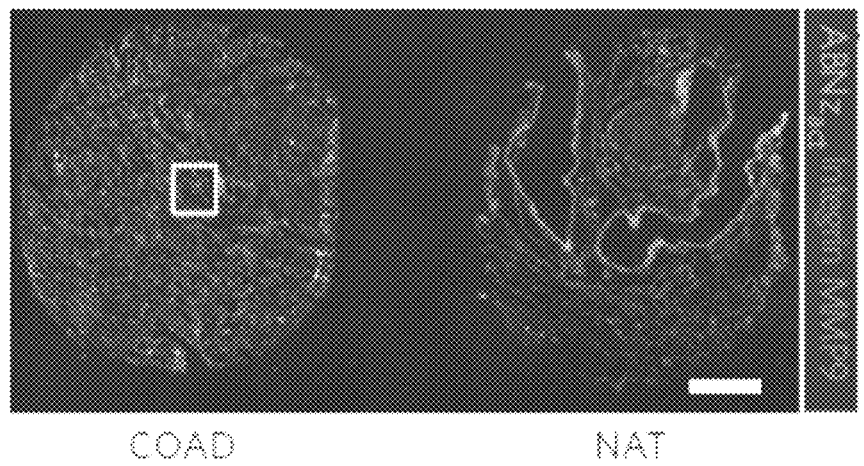
Figure 20E:
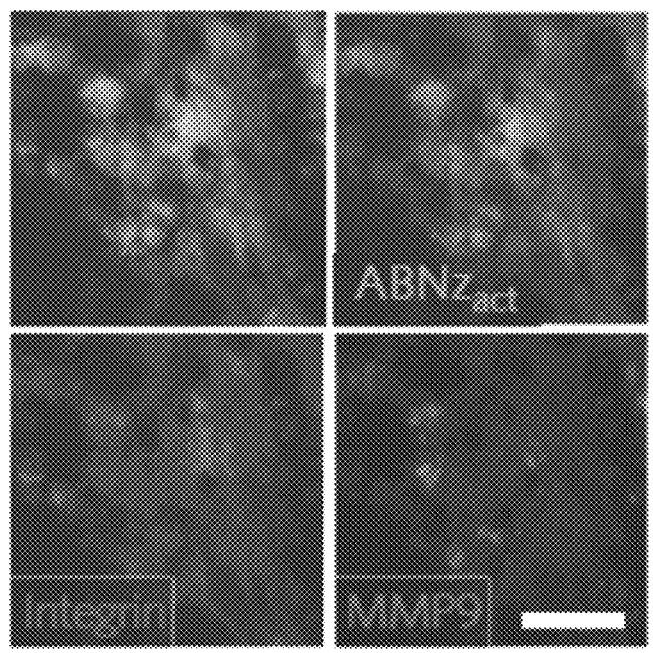

Typically, the evaluation and localization of protease activity on synthetic peptide substrates in excised tissues has been challenging because substrates can diffuse away after proteolysis. To investigate ABN activity in ex vivo tissues, a FRET-pair flanked substrate configured to monitor cleavage with fluorescence imaging was used (FIG. 20A). Combining existing zymography techniques with the ABNs (referred to in this example as ABNz) allowed the mapping of protease activity to tissue localization. In some embodiments, the critical step enabling monitoring involved binding the nanoparticle to the tissue before proteolysis occurred, thereby enabling localization. When iRGD ABNz was applied to frozen liver metastasis sections from CLM mice, the signal was dependent on both MMP activity, which was reduced by pharmacological inhibition, and binding, which was reduced when divalent cations necessary for integrin receptor engagement were omitted (FIG. 20A).

iRGD ABNz were also applied to a frozen human CRC TMA that contained biopsies from tumors and normal adjacent tissue (FIG. 20B). The extent of signal co-localization for activated ABNz, integrin and MMP9 in the cells of each tissue core was blindly scored. The results indicated that ABNz responded differently to tumor tissue compared with normal adjacent tissue, with 9 of 20 tumor cores showing a high signal, compared with only 3 of the 20 normal cores (FIG. 20C). It was observed that the normal adjacent tissues were collected from CRC patients and may have had elevated protease levels compared with tissue from healthy patients. A closer examination of the tissue (FIG. 20D-20E) showed examples of ABNz activation co-localizing with integrin and MMP9 staining. The observation that ABN-based signal generation correlates with MMP9 and integrin expression supports the applicability of this platform to the detection of human cancers. Beyond this application, the ABN technology described by the disclosure could also be used as a tool to profile human tissues for spatial information on protease activity that could support the translation of other protease-sensitive technologies and therapeutics.

Materials and Methods

MMP9 Expression Analysis

MMP9 expression data was queried from Oncomine and TCGA where transcriptomic data were available for both tumor and control samples. The following cancers were analyzed: Head and Neck (Ginos et al., Cancer Res 2004; 13 normal, 41 tumor), Lung (Bhattacharjee et al., PNAS 2001; 17 normal, 132 tumor), Breast (TCGA; 61 normal, 529 tumor), Glioblastoma (TCGA; 5 normal, 82 tumor), Colon (TCGA; 41 normal, 286 tumor), Ovarian (TCGA; 8 normal, 586 tumor), Prostate (Yu et al., J Clin Oncol 2004; 23 normal, 89 tumor), Liver (Roessler et al., Cancer Res 2010; 220 normal, 225 tumor), Melanoma (Riker et al., BMC Med Genomics; 5 normal, 82 tumor) and Pancreatic (Badea et al., Hepatogastroenterology 2008; 39 normal, 39 tumor). Expression in tumors was normalized to controls from each data set.

Tissue Microarray Staining and Scoring

A multiple-organ cancer and normal-tissue microarray was obtained from US Biomax (MC5003b). The microarray was stained with anti-MMP9 antibodies (Abcam; 1:1,000). Blind scoring of cores was performed by a pathologist.

Synthesis of Peptides and Nanoparticles

All peptides were commercially synthesized. For recombinant enzyme studies and ABNz, intramolecularly quenched peptides were used: MMP substrate, 5-FAM-GGPLGVRGKK(CPQ2)-PEG2-C(SEQ ID NO: 17); thrombin substrate, 5-FAM-GGfPRSGGGK(CPQ2)-PEG2-C (SEQ ID NO: 18); where 5-FAM is the 5-carboxyfluorescein fluorophore, CPQ2 is the quencher, PEG2 is the linker polyethylene glycol, and lower case letters indicate the $_D$-stereoisomer of the residue. In vivo protease-sensitive substrates were synthesized to contain a urinary reporter comprised of a protease-resistant $_D$-stereoisomer of glutamate-fibrinopeptide B with a near-infrared dye for urinary detection (biotin-CGPLGVRGKK(Cy7)eGvndneeGffsar; Cy7 is cyanine7; SEQ ID NO: 19). Targeting peptides were synthesized and cyclized: LyP1, C-K(5-FAM)-C6-CGNKRTRGC (SEQ ID NO: 20); iRGD, C-PEG2-CRGDKGPDC (SEQ ID NO: 21); where C6 is the 6-aminohexanoic acid linker, Cys2 and Cys3 bridge.

Iron-oxide nanoparticles were formed by reacting iron (III) chloride hexahydrate and iron(II) chloride tetrahydrate with dextran. These nanoparticles are biocompatible and safe, and were cleared from the animal within five days. Nanoparticles were aminated by reaction with ammonium hydroxide. Size measurements were performed by dynamic light scattering (Malvem Instruments Nano ZS90). For conjugation of peptides to NPs, the NPs were first reacted with NHS-VivoTag 680 (VT680, Perkin Elmer) and MAL-PEG(5k)-SVA (Laysan Bio) to introduce sulfhydryl reactive handles. Cysteine-terminated peptides were then reacted with the NPs and unreacted peptide was filtered using spin filters (molecular weight cut-off, 30 kDa; Millipore). For experiments to identify optimal PEG lengths, PEG of varying lengths was purchased (Thermo Fisher) and reacted in the same manner. Nanoparticles were stored in PBS at 4° C. or at −20° C. Valencies of peptide conjugation and concentrations were quantified by absorbance (Molecular Devices SpectraMax Plus). Typical valencies were ~60 protease-cleavable peptides, ~5 targeting peptides and ~10 VT680s per nanoparticle.

In Vitro Recombinant Protease Assays

Nanoparticles coupled with intramolecularly quenched peptide substrates were reacted with recombinant proteases to identify cleavage velocities. NPs were mixed with 1% (w/v) BSA (Sigma) and incubated with recombinant proteases (MMP-9, Enzo Life Sciences; thrombin, Haematologic Technologies) in a final volume of 50 µl in enzyme-specific buffers (MMP9 buffer: 50 mM Tris, 150 mM NaCl, 5 mM $CaCl_2$), 1 µM $ZnCl_2$, pH 7.5; thrombin: PBS) in a 384-well plate for time-lapse fluorimetry to measure dequenching at 37° C. (SpectroMax Gemini EM microplate reader). Michaelis-Menten constants were determined by assessing initial cleavage velocities at different substrate concentrations (Prism 5.0, GraphPad). The final MMP-9 concentration was 100 nM and the final thrombin concentration was 7 nM.

Cell Culture

The MDA-MB-435 human cancer cell line and MC-26 mouse colon carcinoma cell line were cultured in Dulbecco's modified Eagle medium supplemented with 10% fetal bovine serum and 1% penicillin-streptomycin. The OVCAR-8 human ovarian cancer cell line was cultured in Roswell Park Memorial Institute medium supplemented with 10% fetal bovine serum and 1% penicillin-streptomycin. All cell lines used in these studies were tested for *mycoplasma*.

Antibody Staining and Flow Cytometry

To confirm the expression of targetable integrins on the MC-26 cells, cells were collected with enzyme-free cell-dissociation buffer (Thermo Fisher). Cells were stained for a, integrin (550024, BD Pharmingen; 1:100), NRP-1 (AF566, R&D Biosystems; 1:100), and p32 (AB 2991, Millipore; 1:100) at 4° C. for 1 h and then probed with secondary antibodies conjugated to fluorophores using standard protocols. Cells were analyzed by flow cytometry on a BD LSR 11 flow cytometer.

ELISA for Ovarian Cancer Blood Biomarkers

Secreted and cytoplasmic levels of HE4 were measured by ELISA, according to the manufacturer's protocol (R&D Systems). Cultured supernatant and lysed cells from five cell lines were diluted as needed. All measurements were normalized to the number of cells and the secretion time.

MDA-MB-435 Subcutaneous Xenograft Studies

To generate subcutaneous grafts, three- to four-week-old female NCr nude mice (Taconic) were injected bilaterally with 5×106 MDA-MB-435 cells per flank. Urine measurements were made prior to tumor inoculation by intravenously injecting either 0.5 µM LyP1 or NTP ABNs (by protease cleavable peptide) in 200 µl of PBS at weekly intervals after inoculation. After nanoparticle injection, mice were placed in custom housing with a 96-well plate base for urine collection. After 1 h, their bladders were voided to collect between 100-200 µl of urine. For analysis, urine was diluted between 10- and 25-fold in PBS. Reporter concentration was quantified by measurement of Cy7 fluorescence using a LI-COR Odyssey infrared imaging system (with reference to a ladder). Tumor sizes were measured using digital electronic calipers (Marathon Management) and their volume was calculated as 0.5×length×width$^2$, where length and width are the larger and smaller dimensions, respectively. Total tumor volume was defined as the sum of the tumor volume in each flank. Mice were binned on the basis of tumor sizes and the urine signal was quantified for these bins. ROC curves were generated using Prism.

For NP quantification and determination of the NP distribution in organs and tumors, mice were sacrificed 3 h after the NP injection, and the organs were removed and scanned in the LI-COR Odyssey. Fluorescence from the nanoparticle scaffold (VT680) and the peptide (Cy7) was quantified using the ImageJ software package (National Institutes of Health).

Pharmacokinetic Mathematical Model

A description and derivation of the model is provided in Kwong. G. A. et al., Mathematical framework for activity-based cancer biomarkers. *Proc. Natl. Acad Sci. USA* (2015). The measured properties of ABNs were inputted by modifying the base case values from the previous model. From the data shown in FIG. 3A-3G, MMP9 cleavage was found to increase 4-fold for 6 µM of substrate and thrombin cleavage decreased 1-fold at the same substrate concentration. These numbers were inputted to change the base case values for kcat,tumor and kcat,background by the respective fold changes observed. Here, the change in thrombin cleavage was assumed to be abstracted to background proteolysis for simplicity. From the data shown in FIG. 3G, it can be seen that tumoral accumulation increased 1.2-fold. The permeability term knp_tumor in the ordinary differential equation by the observed difference. The nanoparticle half-life was modified to match that of the tested ABNs. For the 10 mm tumor, the base case model tumor-enzyme concentration of 700 nM was used, and for the 5 mm tumor, a concentration of 7 nM was used, which is in the range observed for tumors of this size.

Ovarian Cancer Orthotopic Model Studies

To generate an orthotopic model of human ovarian cancer, three- to four-week-old female NCr nude mice were injected intraperitoneally with 2×106 OVCAR-8 cells expressing firefly luciferase. Tumor burden was measured via luminescence using an in vivo imaging system (IVIS, PerkinElmer). Each mouse was sacrificed and the tumors were retrieved from all organs in the peritoneal space. Tumors were collected on a glass slide and scanned on a LI-COR Odyssey with 169 µm resolution. Widths and lengths were measured with ImageJ and tumor volume was calculated as described above for subcutaneous tumors. The reported tumor volumes for each group are the average of ten mice. The size distribution of nodules recovered from each mouse is shown in FIG. 11C. Before tumor induction, urine measurements were performed by injecting mice with 0.5 µM LyP1 ABNs. Approximately 200 µl of blood was collected and spiked with EDTA to a final concentration of 5 mM, and the blood cells were pelleted. Plasma was stored at −20° C. prior to HE4 quantification. HE4 levels were measured using the HE4 quantikine ELISA kit.

Liver Metastasis Model Studies

Immunocompetent six- to eight-week-old female BALB/c mice were injected with 5×104 syngeneic MC-26 cells expressing firefly luciferase in the subsplenic capsule to allow cells to seed the liver. After 90 s, the spleen was removed to prevent splenic tumors. Tumor growth was monitored by luminescence and MRI. Before induction of liver metastases, urine measurements were made by injecting 0.5 µM iRGD or LyP-1 ABNs. Post-tumor inoculation urine measurements were performed when tumor luminescence reached an average of 1-1.5×107 photons $s^{-1}cm^{-2}sr^{-1}$.

Toxicity and Clearance Studies

All studies were completed in immunocompetent six- to eight-week-old female BALB/c mice. After administration of ABNs or free reporter, 10 µl of blood and urine were collected at the indicated time points for fluorescence measurements. For tissue clearance and histopathological examination, animals were sacrificed at the indicated time points and their organs were fixed in formalin. Organs were imaged for ABNs with the LI-COR Odyssey as described above, before being embedded in paraffin and then sectioned.

Histology

Immediately after necropsy, organs were fixed in formalin for 24 h and stored at 4° C., before being embedded in paraffin, sectioned and stained. OVCAR-8 tumor sections were stained with p32 (Genscript custom antibody; 1:100) and NRP-1 (AF3870, R&D Biosystems; 1:100). MC-26 tumor sections were stained with $\alpha_v$ integrin (AB1930, Millipore; 1:100), p32 (AB2991, Millipore; 1:100) and NRP-1 (AF566, R&D Biosystems; 1:100).

Application of ABNz

Livers from CLM mice were extracted and immediately embedded and frozen in optimal-cutting-temperature compound. Before application of ABNz, liver sections were air dried and fixed in cold acetone. Protease substrates were designed in a similar manner to the intramolecularly quenched probes used in the in vitro cleavage experiments, except that the fluorophore and quencher positions were reversed. A fresh frozen acetone-fixed human CRC TMA was purchased. After hydration in PBS and blocking in 2% BSA solution for 1 h at 4° C., ABNz was applied and the microarray was incubated for 3 h at 4° C. with, and without, divalent cations in the buffer to allow for binding but no cleavage. The slide was washed and the buffer was exchanged with MMP9 cleavage buffer and incubated at 37° C. overnight in a humidified box. For inhibited controls, 50 µM marimastat was added to the binding and cleavage buffers. Slides were stained with $\alpha_v$ integrin (327902, BioLegend; 1:100) and MMP9 (137867, Abcam ab; 1:500) followed by application of the appropriate secondary antibodies (Jackson Immunolabs). Slides were scanned on a Pannoramic 250 Optimum (PerkinElmer) and co-localization was scored blindly by an independent researcher.

Statistical Analyses

All statistical analyses were performed using GraphPad Prism 5.0 or MATLAB R2013b. Each set of data shown is representative of studies repeated in at least two independent experiments. The sample sizes used for animal experiments (n=7-10) were estimated using a power test with an expected effect size of 50-100% and a variance of 30-50%. No animals were excluded from the analyses. The investigators were not blinded to the groups and treatments during the experiments. For each animal experiment, groups were established before tumorigenesis and therefore no randomization was used in the allocation of groups.

What is claimed is:

1. A method for detecting a tumor in a subject, the method comprising:
   (i) administering to a subject a pro-diagnostic reagent, wherein the pro-diagnostic reagent comprises:
      (a) a carrier domain linked to a signature producing domain, wherein the signature producing domain comprises an enzyme susceptible domain linked to a signature molecule, wherein the enzyme susceptible domain is susceptible to cleavage by a protease that is upregulated in cancer and wherein cleavage of the enzyme susceptible domain releases the signature molecule, and
      (b) one or more tumor-penetrating peptides that bind to a receptor expressed by a cancer cell that mediates an active transport pathway, wherein each tumor-penetrating peptide is linked to the carrier domain; and
   (ii) subjecting a biological sample obtained from the subject to an analysis method in order to detect the presence of the released signature molecule, wherein the analysis method comprises mass spectrometry, PCR analysis, a DNA microarray, fluorescence analysis, or an ELISA, and wherein an increase in the amount of released signature molecule in the biological sample relative to the amount of released signature molecule in a biological sample obtained from a healthy subject who has been administered the pro-diagnostic reagent is indicative of the subject having a tumor.

2. The method of claim 1, wherein the tumor is less than 1 cm in diameter.

3. The method of claim 1, wherein the biological sample is a urine sample or a blood sample.

4. The method of claim 1, wherein the protease that is upregulated in cancer is a serine protease, matrix metalloprotease (MMP), thrombin, kallikrein, matriptase, hepsin, cathepsin, plasminogen activator, or A Disintegrin and Metalloprotease (ADAM).

5. The method of claim 1, wherein the signature molecule is a peptide, nucleic acid, fluorophore, carbohydrate, nanoparticle, microparticle, radiolabel, MRI-active compound, ligand encoded reporter, or isotope coded reporter molecule (iCORE).

6. The method of claim 1, wherein each of the one or more tumor-penetrating peptides specifically binds to a p32 receptor, neuropilin-1 (NRP1) receptor, $\alpha_v\beta_3$ integrin receptor, $\alpha_v\beta_5$ integrin receptor, folate receptor, transferrin receptor, Her2 receptor, or epidermal growth factor receptor (EGFR).

7. The method of claim 1, wherein the one or more tumor-penetrating peptides is selected from the group consisting of: LyP-1 (CGNKRTRGC; SEQ ID NO: 1); iRGD (CRGDKGPDC; SEQ ID NO: 2); tumor-penetrating TT1; and tumor-penetrating peptide iNGR.

8. The method of claim 5, wherein the signature molecule is a fluorophore.

9. The method of claim 5, wherein the signature molecule is a fluorescence resonance energy transfer (FRET) pair.

10. The method of claim 1, wherein the subject is a mammal.

11. The method of claim 10, wherein the mammal is a human.

12. The method of claim 1, wherein the administration is systemic administration.

13. The method of claim 12, wherein the systemic administration is intravenous injection.

14. The method of claim 1, wherein the carrier domain is greater than 5 nm in size.

15. The method of claim 1, wherein the carrier domain is smaller than 5 nm in size.

16. The method of claim 1, wherein the carrier domain is a nanoparticle, RGD peptide, protein, polymer, aptamer, or antibody.

17. The method of claim 1, wherein the carrier domain is an iron-oxide nanoparticle.

18. The method of claim 1, wherein the carrier domain is linked to the signature producing domain by a linker molecule.

19. The method of claim 18, wherein the linker molecule comprises one or more poly(ethylene glycol) (PEG) molecules.

20. The method of claim 1, wherein the pro-diagnostic reagent reduces a tumor detection size limit to between 20 and 50 $mm^3$.

21. The method of claim 1, wherein the pro-diagnostic reagent reduces a urinary detection limit from 150 $mm^3$ to 30 $mm^3$.

* * * * *

UNITED STATES PATENT AND TRADEMARK OFFICE
CERTIFICATE OF CORRECTION

| | | |
|---|---|---|
| PATENT NO. | : 11,519,905 B2 | Page 1 of 1 |
| APPLICATION NO. | : 15/947644 | |
| DATED | : December 6, 2022 | |
| INVENTOR(S) | : Sangeeta N. Bhatia et al. | |

It is certified that error appears in the above-identified patent and that said Letters Patent is hereby corrected as shown below:

In the Claims

In Claim 7, at Column 48, Line 7:
"tumor-penetrating TT1;"
Should read:
--tumor-penetrating peptide TT1;--

Signed and Sealed this
Fourteenth Day of February, 2023

Katherine Kelly Vidal
*Director of the United States Patent and Trademark Office*